(12) United States Patent
Jacobsen et al.

(10) Patent No.: US 6,316,494 B1
(45) Date of Patent: *Nov. 13, 2001

(54) CIS3, 4-CHROMAN DERIVATIVES USEFUL IN THE PREVENTION OR TREATMENT OF ESTROGEN RELATED DISEASES OR SYNDROMES

(75) Inventors: Poul Jacobsen, Slangerup; Svend Treppendahl, Virum; Paul Stanley Bury, København; Anders Kanstrup, Espergærde; Lise Brown Christiansen, Lyngby, all of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/958,684

(22) Filed: Oct. 27, 1997

Related U.S. Application Data

(60) Provisional application No. 60/030,502, filed on Nov. 12, 1996.

(30) Foreign Application Priority Data

Oct. 28, 1996 (DK) .................................................. 1197/96

(51) Int. Cl.[7] .......................... A61K 31/35; A61K 31/55; A61K 31/535; A61K 31/42

(52) U.S. Cl. ...................... 514/456; 514/212; 514/233.7; 514/337; 514/375; 514/422; 514/841; 549/406; 548/237; 548/525; 546/196; 544/151; 540/484

(58) Field of Search ............................ 549/406; 544/151; 546/196; 540/484; 548/237, 525; 514/212, 233.7, 337, 375, 422, 456, 841

(56) References Cited

U.S. PATENT DOCUMENTS

| | | | |
|---|---|---|---|
| 3,340,276 | 9/1967 | Carney et al. | 260/345.2 |
| 3,535,344 | 10/1970 | Irmscher et al. | 260/345.2 |

FOREIGN PATENT DOCUMENTS

| | | |
|---|---|---|
| WO 94/20098 | 9/1994 | (WO) . |
| WO 96/21444 | 7/1996 | (WO) . |

OTHER PUBLICATIONS

Salman et al., J. Med. Chem., vol. 26, pp. 592–595 (1993).
Irmscher et al., Liebigs Ann. Chem., vol. 744, pp. 164–177 (1971).

*Primary Examiner*—Amelia Owens
(74) *Attorney, Agent, or Firm*—Reza Green, Esq.; Valeta A. Gregg, Esq.

(57) ABSTRACT

The present invention relates to therapeutically active compounds of formula I

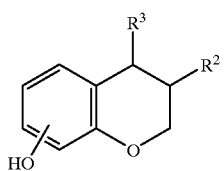

(I)

a method of preparing the same and to pharmaceutical compositions comprising the compounds. The novel compounds are useful in the prevention or treatment of estrogen related diseases or syndromes.

27 Claims, No Drawings

CIS3, 4-CHROMAN DERIVATIVES USEFUL IN THE PREVENTION OR TREATMENT OF ESTROGEN RELATED DISEASES OR SYNDROMES

CROSS-REFERENCE TO RELATED APPLICATIONS

This application claims priority under 35 U.S.C. 119 of Danish application Serial No. 1197/96 filed Oct. 28, 1996 and U.S. provisional application Serial No. 60/030,502 filed Nov. 12, 1996, the contents of which are fully incorporated herein by reference.

FIELD OF THE INVENTION

The present invention relates to new cis-3,4-chroman derivatives and the use of such compounds in the prevention or treatment of estrogen related diseases or syndromes, preferably diseases or syndromes caused by an estrogen-deficient state in a mammal, in particular bone loss, osteoporosis, cardiovascular diseases, cognitive disorders, senile dementia-Alzheimer's type, menopausal symptoms, including flushing and urogenital atrophy, dysmenorrhea, threatened or habitual abortion, dysfunctional uterine bleeding, acne, hirsutism, prostatic carcinoma, post-partum lactation, and the use of such compounds in a contraceptive method or as an aid in ovarian development.

BACKGROUND OF THE INVENTION

The osteopenia that accompanies the menopause continues to represent a major public health problem. Left unchecked, the cumulative loss of bone can potentially compromise the skeleton's structural integrity, resulting in painful and debilitating fractures of the wrist, spine and femur. Efforts to reduce the risk and incidence of fractures have focused on the development of therapies that conserve skeletal mass by inhibiting bone resorption. Among various treatment modalities, estrogen replacement therapy remains the preferred means to prevent the development of post menopausal osteoporosis (Lindsey R, Hart D M, MacClean A 1978, "The role of estrogen/progestogen in the management of the menopause", Cooke I D, ed, Proceedings of University of Sheffield symposium on the role of estrogen and progestogen in the management of the menopause, Lancaster, U K: MTP Press Ltd. pp. 9–25; Marshall D H, Horsmann A, Nordin BEC 1977, "The prevention and management of post-menopausal osteoporosis", Acta Obstet Gynecol Scand (Suppl) 65:49–56; Recker R R, Saville P D, Heaney R P 1977, "Effect of estrogen and calcium carbonate on bone loss in post-menopausal women", Ann Intern Med. 87:649–655; Nachtigall L E, Nachtigall R H, Nachtigall R D, Beckman E M 1979, "Estrogen replacement therapy", Obstet Gynecol. 53:277–281) and it is now accepted that estrogens significantly decrease fracture incidence and risk (Krieger N, Kelsey J L, Holford T R, O'Connor T 1982, "An epidemiological study of hip fracture in postmenopausal women", Am J Epidemiol. 116:141–148; Hutchinson T A, Polansky S M, Feinstein A R 1979, "Post-menopausal estrogens protect against fractures of hip and distal radius: A case-control study", Lancet 2:705–709; Paginini-Hill A, Ross R K, Gerkins V R, Henderson B E, Arthur M, Mack T M 1981, "Menopausal oestrogen therapy and hip fractures", Ann Intern Med. 95:28–31; Weiss N S, Ure C L, Ballard J H, Williams A R, Daling J R 1980, "Decreased risk of fractures on the hip and lower forearm with post-menopausal use of estrogen", N Eng J Med. 303:1195–1198).

While the beneficial actions of estrogen replacement therapy on the skeleton are clearly significant, there is also considerable evidence for a positive effect of estrogen on the cardiovascular system. Previous studies have attributed these actions to estrogen's effects on serum lipids, but recent data has now shown that in addition to the effects on the lipid profile, estrogen can also directly influence vessel wall compliance, reduce peripheral resistance and prevent atherosclerosis (Lobo RA 1990, "Cardiovascular implication of estrogen replacement therapy", Obstetrics and Gynaecology, 75:18S–24S; Mendelson M E, Karas R H 1994, "Estrogen and the blood vessel wall", Current Opinion in Cardiology, 1994(9):619–626). Based on available epidemiological data, the overall impact of these physiological and pharmacological actions of estrogen is an age independent reduction in cardiovascular mortality and morbidity in women (Kannel W H, Hjortland M, McNamara P M 1976 "Menopause and risk of cardiovascular disease: The Framingham Study", Ann Int Med, 85:447–552). Furthermore, a more recent analysis has concluded that post-menopausal estrogen replacement therapy reduces the risk of cardiovascular disease by approximately 50 percent (Stampfer M J, Colditz G A 1991, "Estrogen replacement therapy and coronary heart disease: a quantitative assessment of the epidemiological evidence", Preventive Medicine, 20:47–63.).

In addition to the positive effects of estrogen on bone and cardiovascular system, there are now data which indicate that the central nervous system can benefit from estrogen replacement therapy. Short term studies in human subjects have shown that increased levels of estrogen are associated with higher memory scores in post menopausal women (Kampen D L, Sherwin B B 1994, "Estrogen use and verbal memory in healthy postmenopausal women", Obstetrics and Gynecology, 83(6):979–983). Furthermore, the administration of exogenous estrogen to surgically post menopausal women specifically enhances short-term memory. Moreover, the effects of estrogen on cognition do not appear confined to short-term effects as epidemiological findings indicate that estrogen treatment significantly decreases the risk of senile dementia-Alzheimer's type in women (Paganini-Hill A, Henderson V W, 1994, "Estrogen deficiency and risk of Alzheimer's disease in women", Am J Epidemiol, 140:256–261; Ohkura T, Isse K, Akazawa K, Hamamoto M, Yoshimasa Y, Hagino N, 1995, "Long-term estrogen replacement therapy in female patients with dementia of the Alzheimer Type: 7 case reports", Dementia, 6:99–107). While the mechanism whereby estrogens enhance cognitive function is unknown, it is possible to speculate that the direct effects of estrogen on cerebral blood flow (Goldman H, Skelley Eb, Sandman C A, Kastin A J, Murphy S, 1976, "Hormones and regional brain blood flow", Pharmacol Biochem Rev. 5(suppl 1):165–169; Ohkura T, Teshima Y, Isse K, Matsuda H, Inoue T, Sakai Y, Iwasaki N, Yaoi Y, 1995, "Estrogen increases cerebral and cerebellar blood flows in postmenopausal women", Menopause: J North Am Menopause Soc. 2(1):13–18) and neuronal cell activities (Singh M, Meyer E M, Simpkins J W, 1995, "The effect of ovariectomy and estradiol replacement on brain-derived neurotrophic factor messenger ribonucleic acid expression in cortical and hippocampal brain regions of female Sprague-Dawley rats", Endocrinology, 136:2320–2324; McMillan P J, Singer C A, Dorsa D M, 1996, "The effects of ovariectomy and estrogen replacement on trka and choline acetyltransferase mRNA expression in the basal forebrain of the adult female Sprague-Dawley rat", J Neurosci., 16(5):1860–1865) are potential effectors for these beneficial actions.

The therapeutic applications of naturally occurring estrogens and synthetic compositions demonstrating estrogenic activity alone or in combination are not limited to the chronic conditions described above. Indeed, the more traditional applications of estrogen therapies would include the following: relief of menopausal symptoms (i.e. flushing and urogenital atrophy); oral contraception; prevention of threatened or habitual abortion, relief of dysmenorrhea; relief of dysfunctional uterine bleeding; an aid in ovarian development; treatment of acne; diminution of excessive growth of body hair in women (hirsutism); treatment of prostatic carcinoma: and suppression of postpartum lactation [Goodman and Gilman, The Pharmacological Basis of Therapeutics (Seventh Edition) Macmillan Publishing Company, 1985, pages 1421–1423].

Even though the beneficial effects of estrogen replacement on a wide variety of organ systems and tissues appear indisputable, the dose and duration of estrogen therapy is also associated with an increased risk of endometrial hyperplasia and carcinoma. The use of concomitant cyclic progestins does reduce the risk of endometrial pathology, but this is achieved at the expense of the return of regular uterine bleeding, a result that is objectionable to many patients. In addition to estrogen's stimulatory effect on the endometrium, there remains considerable controversy regarding reports of an association between longterm estrogen replacement and an increased risk of breast cancer (Bergkvist L, Adami H O, Persson I, Hoover R, Schairer C, 1989, "The risk of breast cancer after estrogen and estrogen-progestin replacement", N Eng J Med, 321:293–297; Colditz G A, Hankinson S E, Hunter D J, Willett W C, Manson J E, Stampfer M J, Hennekens C, Rosner B, Speizer F E, 1995, "The use of estrogens and progestins and the risk of breast cancer in postmenopausal women", N Eng J Med, 332(24):1589–1593). Furthermore, there are other side effects of estrogen replacement which, while they may not be life threatening, contraindicate estrogen's use and reduce patient compliance.

From the foregoing discussion it would appear that the availability of therapies which could mimic the beneficial actions of estrogen on the bone, cardiovascular system, and central nervous system without the undesirable side effects on uterus and breast, would essentially provide a "safe estrogen" which could dramatically influence the number of patients that would be able to benefit from estrogen replacement therapy. Therefore, in recognition of estrogen's beneficial effects on a number of body systems and disease conditions, there is a continuing need for the development of potent estrogen agonists which can selectively target different body tissues.

DESCRIPTION OF THE INVENTION

The present invention provides compounds of the formula I in which substituents $R^2$ and $R^3$ are arranged in cis-configuration:

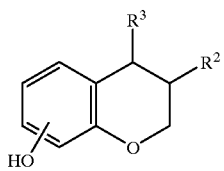

(I)

wherein:

$R^2$ is phenyl optionally substituted with 1 to 5 substituents independently selected from the group consisting of OH, halogen, nitro, cyano, SH, $SR^4$, trihalo-$C_1$–$C_6$-alkyl, $C_1$–$C_6$-alkyl, $C_1$–$C_6$-alkoxy and phenyl;

$R^3$ is:

(a) phenyl substituted with —X—$(CH_2)_n$—Y, wherein:
X is a valency bond, O or S,
n is an integer in the range of 1 to 12,
Y is H, halogen, OH, $OR^4$, $NHCOR^4$, $NHSO_2R^4$, $CONHR^4$, $CONR_2^4$, COOH, $COOR^4$, $SO_2R^4$, $SOR^4$, $SONHR^4$, $SONR_2^4$, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy;

(b) —$(CH_2)_n$—V, wherein n is as defined above and V is H, OH, $OR^4$, $NHR^4$, $NR_2^4$, $NHCOR^4$, $NHSO_2R^4$, $CONHR^4$, $CONR_2^4$, COOH, $COOR^4$, $SO_2R^4$, $SOR^4$, $SONHR^4$, $SONR_2^4$, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy; or (c) phenyl fused to a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy; and $R^4$ is $C_1$–$C_6$-alkyl;

and optical and geometrical isomers, pharmaceutically acceptable esters, ethers and salts thereof.

The general chemical terms used in the above formula have their usual meanings.

For example the term $C_1$–$C_6$-alkyl includes straight-chained as well as branched alkyl groups such as methyl, ethyl, propyl, isopropyl, butyl, s-butyl and isobutyl.

The term halogen means chloro, bromo, iodo and fluoro.

The term $C_3$–$C_7$-heterocyclic ring include groups such as pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl and thiazolyl.

The compounds of this invention are new estrogen agonists and are useful for prevention and treatment of bone loss, prevention and treatment of osteoporosis; the prevention and treatment of cardiovascular disease; treatment and prevention of physiological disorders associated with an excess of neuropeptide Y (e.g. obesity, depression, etc.); and for regulation of glucose metabolism in e.g. non-insulin dependent diabetes melitus; and the prevention and treatment of senile dementia-Alzheimer's type in women. In addition, these estrogen agonists are useful for oral contraception; relief of menopausal symptoms (e.g. hot flushes, urogenital atrophy, depression, mania, schizophrenia, etc.); incontinence; prevention of threatened or habitual abortion; relief of dysmenorrhea; relief of dysfunctional uterine bleeding; an aid in ovarian development; treatment of acne; diminution of excessive growth of body hair is women (hirsutism); treatment of prostatic carcinoma; and the suppression of postpartum lactation. These agents also lower serum cholesterol and have a beneficial effect on plasma lipid profiles.

While the compounds of this invention are estrogen agonists in bone and cardiovascular tissues, they are also capable of acting as antiestrogens in other estrogen target organs. For example, these compounds can act as antiestrogens in breast tissue and the colon and therefore would be useful for the prevention and treatment of estrogen-dependent cancers such as breast cancers and colon cancers.

The hydroxy substituent on the phenyl ring in formula I is preferably attached to the phenyl ring at the 6- or 7-position. Accordingly, compounds of the invention having one of the following formulae Ia or Ib are preferred:

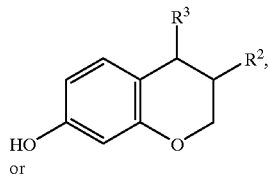
(Ia)

or

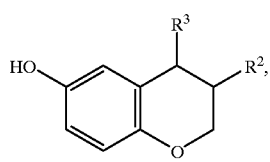
(Ib)

wherein $R^1$, $R^2$ and $R^3$ are as defined above.

In a preferred embodiment, the present invention is concerned with cis-forms of the compounds of the following formula:

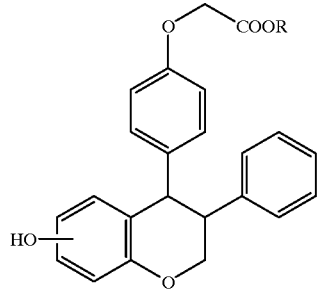

wherein R is H or $C_1$–$C_6$ alkyl.

In another preferred embodiment, the present invention is concerned with cis-forms of the compounds of the following formula:

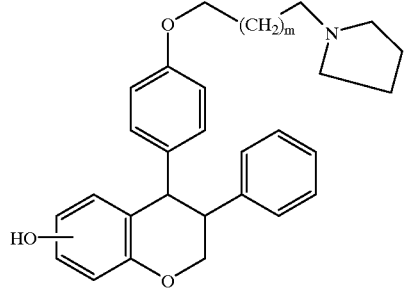

wherein m is an integer from 0 to 10.

In another preferred embodiment, the present invention is concerned with cis-forms of the compounds of the following formula:

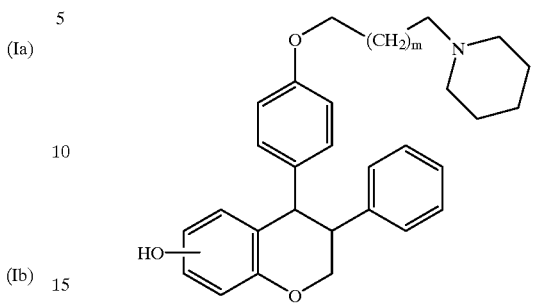

wherein m is as defined above.

In another preferred embodiment, the present invention is concerned with cisforms of the compounds of the following formula:

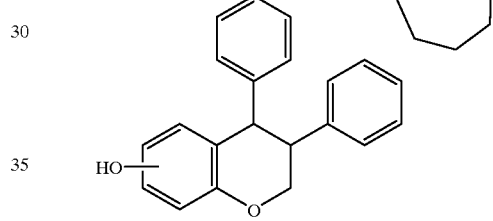

wherein m is as defined above.

In another preferred embodiment, the present invention is concerned with cis-forms of the compounds of the following formula:

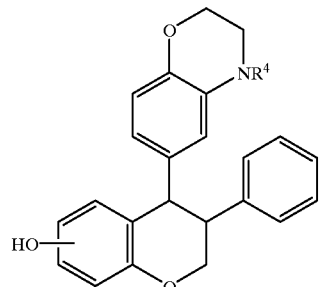

wherein $R^4$ is as defined above.

In another preferred embodiment, the present invention is concerned with cis-forms of the compounds of the following formula:

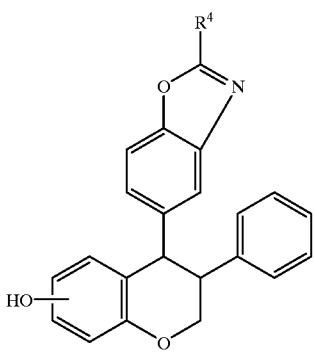

wherein R⁴ is as defined above.

In another preferred embodiment, the present invention is concerned with cis-forms of the compounds of the following formula:

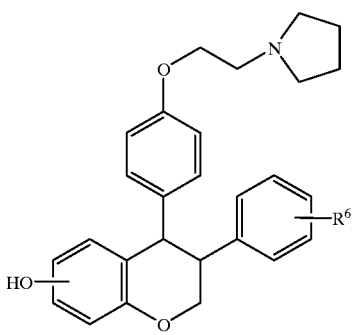

wherein R⁶ represents one or more of the following substituents: methoxy, hydroxy, trifluormethyl, fluoro and chloro.

The most preferred compounds are the following:
(−)-cis-4-(4-(Carboxymethoxy)phenyl)-7-hydroxy-3-phenylchromane,
(−)-cis-7-Hydroxy-4-(4-(methoxycarbonylmethoxy)phenyl)-3-phenylchromane,
(−)-cis-4-(4-(Ethoxycarbonylmethoxy)phenyl)-7-hydroxy-3-phenylchromane,
(−)-cis-4-(4-(Benzyloxycarbonylmethoxy)phenyl)-7-hydroxy-3-phenylchromane,
(−)-cis-7-Hydroxy-3-phenyl-4-(4-(2-pyrrolidinoethoxy)phenyl)chromane,
(−)-cis-7-Hydroxy-3-phenyl-4-(4-(3-pyrrolidinopropoxy)phenyl)chromane,
(−)-cis-7-Hydroxy-3-phenyl-4-(4-(4-pyrrolidinobutoxy)phenyl)chromane,
(−)-cis-7-Hydroxy-3-phenyl-4-(4-(5-pyrrolidinopentoxy)phenyl)chromane,
(−)-cis-7-Hydroxy-3-phenyl-4-(4-(6-pyrrolidinohexyloxy)phenyl)chromane,
(−)-cis-7-Hydroxy-3-phenyl-4-(4-(7-pyrrolidinoheptyloxy)phenyl)chromane,
(−)-cis-7-Hydroxy-3-phenyl-4-(4-(8-pyrrolidinooctyloxy)phenyl)chromane,
(−)-cis-7-Hydroxy-3-phenyl-4-(4-(9-pyrrolidinononyloxy)phenyl)chromane,
(−)-cis-7-Hydroxy-3-phenyl-4-(4-(10-pyrrolidinodecyloxy)phenyl)chromane,
(−)-cis-7-Hydroxy-3-phenyl-4-(4-(11-pyrrolidinoundecyloxy)phenyl)chromane,
(−)-cis-7-Hydroxy-3-phenyl-4-(4-(12-pyrrolidinododecyloxy)phenyl)chromane,
(−)-cis-7-Hydroxy-3-phenyl-4-(4-(2-piperidinoethoxy)phenyl)chromane,
(−)-cis-7-Hydroxy-3-phenyl-4-(4-(3-piperidinopropoxy)phenyl)chromane,
(−)-cis-7-Hydroxy-3-phenyl-4-(4-(4-piperidinobutoxy)phenyl)chromane,
(−)-cis-7-Hydroxy-4-(4-(2-perhydroazepinoethoxy)phenyl)-3-phenylchromane,
(−)-cis-7-Hydroxy-4-(4-(3-perhydroazepinopropoxy)phenyl)-3-phenylchromane,
(−)-cis-7-Hydroxy-4-(4-(4-perhydroazepinobutoxy)phenyl)-3-phenylchromane,
(−)-cis-4-(2,3-Dihydro-1,4-benzoxazin-6-yl)-7-hydroxy-3-phenylchromane,
(−)-cis-7-Hydroxy-4-(4-methyl-2,3-dihydro-1,4-benzoxazin-6-yl)-3-phenylchromane,
(−)-cis-4-(4-Ethyl-2,3-dihydro-1,4-benzoxazin-6-yl)-7-hydroxy-3-phenylchromane,
(−)-cis-7-Hydroxy-3-(4-hydroxyphenyl)-4-(4-(2-pyrrolidinoethoxy)phenyl)chromane,
(−)-cis-7-Hydroxy-3-(4-trifluoromethylphenyl)-4-(4-(2-pyrrolidinoethoxy)phenyl)chromane,
(−)-cis-7-Hydroxy-3-(4-fluorophenyl)-4-(4-(2-pyrrolidinoethoxy)phenyl)chromane,
(−)-cis-3-(4-Chlorophenyl)-7-hydroxy-4-(4-(2-pyrrolidinoethoxy)phenyl)chromane,
(−)-cis-3-(3,4-Dimethoxyphenyl)-7-hydroxy-4-(4-(2-pyrrolidinoethoxy)phenyl)chromane,
(−)-cis-7-Hydroxy-3-(pentafluorophenyl)-4-(4-(2-pyrrolidinoethoxy)phenyl)chromane,
(−)-cis-4-(4-(Carboxymethoxy)phenyl)-6-hydroxy-3-phenylchromane,
(−)-cis-6-Hydroxy-4-(4-(methoxycarbonylmethoxy)phenyl)-3-phenylchromane,
(−)-cis-4-(4-(Ethoxycarbonylmethoxy)phenyl)-6-hydroxy-3-phenylchromane,
(−)-cis-4-(4-(Benzyloxycarbonylmethoxy)phenyl)-6-hydroxy-3-phenylchromane,
(−)-cis-6-Hydroxy-3-phenyl-4-(4-(2-pyrrolidinoethoxy)phenyl)chromane,
(−)-cis-6-Hydroxy-3-phenyl-4-(4-(3-pyrrolidinopropoxy)phenyl)chromane,
(−)-cis-6-Hydroxy-3-phenyl-4-(4-(4-pyrrolidinobutoxy)phenyl)chromane,
(−)-cis-6-Hydroxy-3-phenyl-4-(4-(5-pyrrolidinopentoxy)phenyl)chromane,
(−)-cis-6-Hydroxy-3-phenyl-4-(4-(6-pyrrolidinohexyloxy)phenyl)chromane,
(−)-cis-6-Hydroxy-3-phenyl-4-(4-(7-pyrrolidinoheptyloxy)phenyl)chromane,
(−)-cis-6-Hydroxy-3-phenyl-4-(4-(8-pyrrolidinooctyloxy)phenyl)chromane,
(−)-cis-6-Hydroxy-3-phenyl-4-(4-(9-pyrrolidinononyloxy)phenyl)chromane,
(−)-cis-6-Hydroxy-3-phenyl-4-(4-(10-pyrrolidinodecyloxy)phenyl)chromane,
(−)-cis-6-Hydroxy-3-phenyl-4-(4-(11-pyrrolidinoundecyloxy)phenyl)chromane,
(−)-cis-6-Hydroxy-3-phenyl-4-(4-(12-pyrrolidinododecyloxy)phenyl)chromane,
(−)-cis-6-Hydroxy-3-phenyl-4-(4-(2-piperidinoethoxy)phenyl)chromane,
(−)-cis-6-Hydroxy-3-phenyl-4-(4-(3-piperidinopropoxy)phenyl)chromane,
(−)-cis-6-Hydroxy-3-phenyl-4-(4-(4-piperidinobutoxy)phenyl)chromane,
(−)-cis-6-Hydroxy-4-(4-(2-perhydroazepinoethoxy)phenyl)-3-phenylchromane, (−)-cis-6-Hydroxy-4-(4-(3-perhydroazepinopropoxy) phenyl)-3-phenylchromane,
(−)-cis-6-Hydroxy-4-(4-(4-perhydroazepinobutoxy) phenyl)-3-phenylchromane,
(−)-cis-4-(2,3-Dihydro-1,4-benzoxazin-6-yl)-6-hydroxy-3-phenylchromane,
(−)-cis-6-Hydroxy-4-(4-methyl-2,3-dihydro-1,4-benzoxazin-6-yl)-3-phenylchromane,
(−)-cis-4-(4-Ethyl-2,3-dihydro-1,4-benzoxazin-6-yl)-6-hydroxy-3-phenylchromane,
(−)-cis-6-Hydroxy-3-(4-hydroxyphenyl)-4-(4-(2-pyrrolidinoethoxy)phenyl)chromane,
(−)-cis-6-Hydroxy-3-(4-trifluoromethylphenyl)-4-(4-(2-pyrrolidinoethoxy)phenyl)chromane,
(−)-cis-6-Hydroxy-3-(4-fluorophenyl)-4-(4-(2-pyrrolidinoethoxy)phenyl)chromane,
(−)-cis-3-(4-Chlorophenyl)-6-hydroxy-4-(4-(2-pyrrolidinoethoxy)phenyl)chromane,
(−)-cis-3-(3,4-Dimethoxyphenyl)-6-hydroxy-4-(4-(2-pyrrolidinoethoxy)phenyl)chromane,
(−)-cis-6-Hydroxy-3-(pentafluorophenyl)-4-(4-(2-pyrrolidinoethoxy)phenyl)chromane,
(+)-cis-4-(4-(Carboxymethoxy)phenyl)-7-hydroxy-3-phenylchromane,
(+)-cis-7-Hydroxy-4-(4-(methoxycarbonylmethoxy) phenyl)-3-phenylchromane,
(+)-cis-4-(4-(Ethoxycarbonylmethoxy)phenyl)-7-hydroxy-3-phenylchromane,
(+)-cis-4-(4-(Benzyloxycarbonylmethoxy)phenyl)-7-hydroxy-3-phenylchromane,
(+)-cis-7-Hydroxy-3-phenyl-4-(4-(2-pyrrolidinoethoxy) phenyl)chromane,
(+)-cis-7-Hydroxy-3-phenyl-4-(4-(3-pyrrolidinopropoxy) phenyl)chromane,
(+)-cis-7-Hydroxy-3-phenyl-4-(4-(4-pyrrolidinobutoxy) phenyl)chromane,
(+)-cis-7-Hydroxy-3-phenyl-4-(4-(5-pyrrolidinopentoxy) phenyl)chromane,
(+)-cis-7-Hydroxy-3-phenyl-4-(4-(6-pyrrolidinohexyloxy) phenyl)chromane,
(+)-cis-7-Hydroxy-3-phenyl-4-(4-(7-pyrrolidinoheptyloxy) phenyl)chromane ,
(+)-cis-7-Hydroxy-3-phenyl-4-(4-(8-pyrrolidinooctyloxy) phenyl)chromane,
(+)-cis-7-Hydroxy-3-phenyl-4-(4-(9-pyrrolidinononyloxy) phenyl)chromane,
(+)-cis-7-Hydroxy-3-phenyl-4-(4-(10-pyrrolidinodecyloxy) phenyl)chromane,
(+)-cis-7-Hydroxy-3-phenyl-4-(4-(11-pyrrolidinoundecyloxy)phenyl)chromane,
(+)-cis-7-Hydroxy-3-phenyl-4-(4-(12-pyrrolidinododecyloxy)phenyl)chromane,
(+)-cis-7-Hydroxy-3-phenyl-4-(4-(2-piperidinoethoxy) phenyl)chromane,
(+)-cis-7-Hydroxy-3-phenyl-4-(4-(3-piperidinopropoxy) phenyl)chromane,
(+)-cis-7-Hydroxy-3-phenyl-4-(4-(4-piperidinobutoxy) phenyl)chromane,
(+)-cis-7-Hydroxy-4-(4-(2-perhydroazepinoethoxy) phenyl)-3-phenylchromane,
(+)-cis-7-Hydroxy-4-(4-(3-perhydroazepinopropoxy) phenyl)-3-phenylchromane,
(+)-cis-7-Hydroxy-4-(4-(4-perhydroazepinobutoxy) phenyl)-3-phenylchromane,
(+)-cis-4-(2,3-Dihydro-1,4-benzoxazin-6-yl)-7-hydroxy-3-phenylchromane,
(+)-cis-7-Hydroxy-4-(4-methyl-2,3-dihydro-1,4-benzoxazin-6-yl)-3-phenylchromane,
(+)-cis-4-(4-Ethyl-2,3-dihydro-1,4-benzoxazin-6-yl)-7-hydroxy-3-phenylchromane,
(+)-cis-7- Hydroxy-3-(4-hydroxyphenyl)-4-(4-(2-pyrrolidinoethoxy)phenyl)chromane,
(+)-cis-7-Hydroxy-3-(4-trifluoromethylphenyl)-4-(4-(2-pyrrolidinoethoxy)phenyl)chromane,
(+)-cis-7-Hydroxy-3-(4-fluorophenyl)4-(4-(2-pyrrolidinoethoxy)phenyl)chromane,
(+)-cis-3-(4-Chlorophenyl)-7-hydroxy-4-(4-(2-pyrrolidinoethoxy)phenyl)chromane,
(+)-cis-3-(3,4-Dimethoxyphenyl)-7-hydroxy-4-(4-(2-pyrrolidinoethoxy)phenyl)chromane,
(+)-cis-7-Hydroxy-3-(pentafluorophenyl)-4-(4-(2-pyrrolidinoethoxy)phenyl)chromane,
(+)-cis-4-(4-(Carboxymethoxy)phenyl)-6-hydroxy-3-phenylchromane,
(+)-cis-6-Hydroxy4-(4-(methoxycarbonylmethoxy)phenyl)-3-phenylchromane,
(+)-cis-4-(4-(Ethoxycarbonylmethoxy)phenyl)-6-hydroxy-3-phenylchromane,
(+)-cis-4-(4-(Benzyloxycarbonylmethoxy)phenyl)-6-hydroxy-3-phenylchromane,
(+)-cis-6-Hydroxy-3-phenyl-4-(4-(2-pyrrolidinoethoxy) phenyl)chromane,
(+)-cis-6-Hydroxy-3-phenyl-4-(4-(3-pyrrolidinopropoxy) phenyl)chromane,
(+)-cis-6-Hydroxy-3-phenyl-4-(4-(4-pyrrolidinobutoxy) phenyl)chromane,
(+)-cis-6-Hydroxy-3-phenyl-4-(4-(5-pyrrolidinopentoxy) phenyl)chromane,
(+)-cis-6-Hydroxy-3-phenyl-4-(4-(6-pyrrolidinohexyloxy) phenyl)chromane,
(+)-cis-6-Hydroxy-3-phenyl-4-(4-(7-pyrrolidinoheptyloxy )phenyl) chromane,
(+)-cis-6-Hydroxy-3-phenyl-4-(4-(8-pyrrolidinooctyloxy) phenyl)chromane,
(+)-cis-6-Hydroxy-3-phenyl-4-(4-(9-pyrrolidinononyloxy) phenyl)chromane,
(+)-cis-6-Hydroxy-3-phenyl-4-(4-(10-pyrrolidinodecyloxy) phenyl)chromane,
(+)-cis-6-Hydroxy-3-phenyl-4-(4-(11-pyrrolidinodododecyloxy)phenyl)chromane ,
(+)-cis-6-Hydroxy-3-phenyl-4-(4-(12-pyrrolidinodecytoxy) phenyl)chromane,
(+)-cis-6-Hydroxy-3-phenyl-4-(4-(2-piperidinopreooxy) phenyl)chromane,
(+)-cis-6-Hydroxy-3-phenyl-4-(4-(3-piperidinobutoxy) phenyl) chromane,
(+)-cis-6-Hydroxy-3-phenyl-4-(4-(4-piperidinobutoxy) phenyl)chromane,
(+)-cis-6-Hydroxy-4-(4-(2-perhydroazepinoethoxy) phenyl)-3-phenylchromane,
(+)-cis-6-Hydroxy-4-(4-(3-perhydroazepinopropoxy) phenyl)-3-phenylchromane,
(+)-cis-6-Hydroxy-4-(4-(4-perhydroazepinobutoxy) phenyl)-3-phenylchromane,
(+)-cis-4-(2,3-Dihydro- 1,4-benzoxazin-6-yl)-6-hydroxy-3-phenylchromane,
(+)-cis-6-Hydroxy-4-(4-methyl-2,3-dihydro-1,4-benzoxazin-6-yl)-3-phenylchromane,
(+)-cis-4-(4-Ethyl-2,3-dihydro-1,4-benzoxazin-6-yl)-6-hydroxy-3-phenylchromane,
(+)-cis-6-Hydroxy-3-(4-hydroxyphenyl)-4-(4-(2-pyrrolidinoethoxy)phenyl)chromane,
(+)-cis-6-Hydroxy-3-(4-trifluoromethylphenyl)-4-(4-(2-pyrrolidinoethoxy)phenyl)chromane,
(+)-cis-6-Hydroxy-3-(4-fluorophenyl)-4-(4-(2-pyrrolidinoethoxy)phenyl)chromane, (+)-cis-3-(4-Chlorophenyl)-6-hydroxy-4-(4-(2-pyrrolidinoethoxy)phenyl)chromane,
(+)-cis-3-(3,4-Dimethoxyphenyl)-6-hydroxy4-(4-(2-pyrrolidinoethoxy)phenyl)chromane,
(+)-cis-6-Hydroxy-3-(pentafluorophenyl)-4-(4-(2-pyrrolidinoethoxy)phenyl)chromane,
(+)-cis-7-Hydroxy-3-phenyl-4-{4-{2-(pyrrolidin-1-yl)ethoxy}phenyl}chromane,
(−)-cis-7-Hydroxy-3-phenyl-4-{4-[2-(pyrrolidin-1-yl)ethoxy]phenyl}chromane,
(+)-cis-7-Hydroxy-4-(4-(2-pyrrolidinoethoxy)phenyl)-3-(4-(trifluoromethyl)phenyl)-chromane,
(+)-cis-7-Hydroxy-3-(4-methylphenyl)-4-(4-(2-pyrrolidinoethoxy)phenyl)chromane,
(+)-cis-7-Hydroxy-3-(3-hydroxyphenyl)-4-(4-(2-pyrrolidinoethoxy)phenyl)chromane,
(−)-cis-7-Hydroxy-4-(4-(2-pyrrolidinoethoxy)phenyl)-3-(4-(trifluoromethyl)phenyl)-chromane,
(−)-cis-7-Hydroxy-3-(4-methylphenyl)-4-(4-(2-pyrrolidinoethoxy)phenyl)chromane,
(−)-cis-7-Hydroxy-3-(3-hydroxyphenyl)-4-(4-(2-pyrrolidinoethoxy)phenyl)chromane,
and mixtures thereof including racemic mixtures.

The following compounds also form part of the disclosure of the present invention:
(±)-cis-7-Hydroxy-3-phenyl-4-{4-{2-(pyrrolidin-1-yl)ethoxy}phenyl}chromane,
(±)-cis-7-Hydroxy-3-(4-fluorophenyl)-4-(4-(2-pyrrolidinoethoxy)phenyl)chromane,
(±)-cis-7-Hydroxy-3-(4-fluorophenyl)-4-(4-(2-piperidinoethoxy)phenyl)-chromane,
(±)-cis-7-Hydroxy-3-(4-fluorophenyl)-4-(4-(3-piperidinopropoxy)phenyl)chromane,
(±)-cis-7-Hydroxy-3-phenyl-4-(4-(2-piperidinoethoxy)phenyl)chromane,
(±)-cis-7-Hydroxy-3-phenyl-4-(4-(2-piperidinoethoxy)phenyl)chromane,
(±)-cis-7-Hydroxy-3-(4-hydroxyphenyl)-4-(4-(2-pyrrolidinoethoxy)phenyl)chromane,
(±)-cis-7-Hydroxy-3-(4-phenyl-phenyl)-4-(4-(2-pyrrolidinoethoxy)phenyl)chromane,
(±)-cis-7-Hydroxy-3-(4-methylphenyl)-4-(4-(2-pyrrolidinoethoxy)phenyl)chromane,
(±)-cis-7-Hydroxy-3-(4-methylphenyl)-4-(4-(2-piperidinoethoxy)phenyl)chromane,
(±)-cis-7-Hydroxy-4-(4-(2-piperidinoethoxy)phenyl)-3-(4-(trifluoromethylphenyl)-chromane,
(±)-cis-7-Hydroxy-4-(4-(2-pyrrolidinoethoxy)phenyl)-3-(4-(trifluoromethyl)phenyl)-chromane,
(±)-cis-7-Hydroxy-3-(3-methylphenyl)-4-(4-(2-pyrrolidinoethoxy)phenyl)chromane,
(±)-cis-3-(3-Fluorophenyl)-7-hydroxy-4-(4-(2-pyrrolidinoethoxy)phenyl)chromane,
(±)-cis-7-Hydroxy-3-(3-hydroxyphenyl)-4-(4-(2-pyrrolidinoethoxy)phenyl)chromane,
(±)-cis-7-Hydroxy-3-(3-hydroxyphenyl)-4-(4-(2-piperidinoethoxy)phenyl)chromane,
(±)-cis-7-Hydroxy-3-(3-hydroxyphenyl)-4-(4-(3-piperidinopropoxy)phenyl)chromane,
(±)-cis-7-Hydroxy-4-(4-(2-pyrrolidinoethoxy)phenyl)-3-(3-(trifluoromethyl)phenyl)chromane,
(±)-cis-7-Hydroxy-4-(4-(2-piperidinoethoxy)phenyl)-3-(3-(trifluoromethyl)phenyl)chromane,
(±)-cis-3-(2-Fluorophenyl)-7-hydroxy-4-(4-(2-pyrrolidinoethoxy)phenyl)chromane,
(±)-cis-7-Hydroxy-3-(2,3,4,5,6-pentafluorophenyl)-4-(4-(2-pyrrolidinoethoxy)phenyl)-chromane,
(±)-cis-7-Hydroxy-3-(2,3,4,5,6-pentafluorophenyl)-4-(4-(2-piperidinoethoxy)phenyl)-chromane,
(±)-cis-6-Hydroxy-3-phenyl-4-(4-(2-pyrrolidinoethoxy)phenyl)-chromane,
(±)-cis-6-Hydroxy-3-(3-hydroxyphenyl)-4-(4-(2-pyrrolidinoethoxy)phenyl)chromane,
(±)-cis-4-(4-Hexylphenyl)-7-hydroxy-3-phenylchromane,
(+,−) cis [4-(7-Hydroxy-3-phenyl-chroman-4-yl)-phenoxy]-acetic acid,
(+,−) cis 4-[4-(7-Hydroxy-3-phenyl-chroman-4-yl)-phenoxy]-butyric acid,
(+,−) cis 7-hydroxy-4-[4-(6-morpholinohexyloxy)-phenyl]-3-phenyl-chroman,
(+,−) cis 7-Hydroxy 4-[4-(morpholinoethyloxy)-phenyl]-3-phenyl-chroman,
(+,−) cis 7-Hydroxy 4-[4-(N-methylpiperazinoethyloxy)-phenyl]-3-phenyl-chroman,
(+,−) cis 7-Hydroxy 4-[4-(morpholinobutyloxy)-phenyl]-3-phenyl-chroman,
(+,−) cis 7-Hydroxy 4-[4-(morpholinobutyloxy)-phenyl]-3-phenyl-chroman,
(+,−) cis 7-Hydroxy-4-[4-(morpholinodecyloxy)-phenyl]-3-phenylchroman including the pure enantiomers thereof.

The compounds of the invention may be prepared by resorting to the chroman chemistry which is well-known in the art, for example in P. K. Arora, P. L. Kole and S. Ray, Indian J. Chem. 20 B, 41–5, 1981; S. Ray, P. K. Grover and N. Anand, Indian J. Chem. 9, 727–8, 1971; S. Ray, P. K. Grover, V. P. Kamboj, S. B. Betty, A. B. Kar and N. Anand, J. Med. Chem. 19, 276–9, 1976; Md. Salman, S. Ray, A. K. Agarwal, S. Durani, B. S. Betty, V. P. Kamboj and N. Anand, J. Med. Chem. 26, 592–5,1983; Teo, C., Sim, K., Bull. Singapore Natl. Inst. Chem. 22, 69–74, 1994.

However, the invention is furthermore concerned with a general method for the preparation of compounds of formula (I) comprising the steps of:

a) reacting a compound of the formula (II)

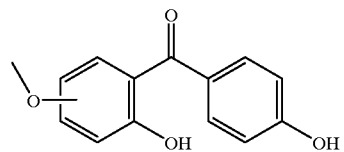

(II)

with a compound of the formula (III)

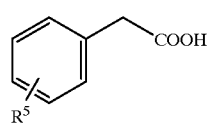

(III)

wherein $R^5$ represents 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy, and $R^4$ is as defined above, in the presence of triethylamine and acetic anhydride to form a compound of the formula (IV)

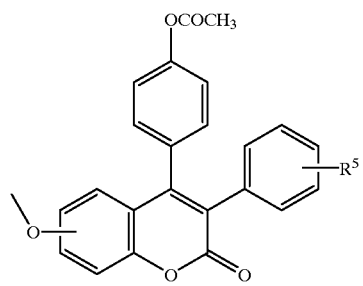

(IV)

wherein R⁵ is as defined above, b) reducing a compound of the formula (IV) with a suitable hydride reducing agent to form a compound of formula (V)

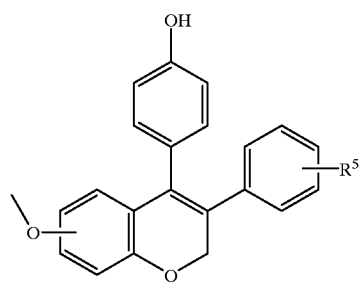

(V)

wherein R⁵ is as defined above, c) hydrogenating a compound of the formula (V) in the presence of a suitable catalyst to form a compound of the formula (VI) with a 3,4-cis configuration

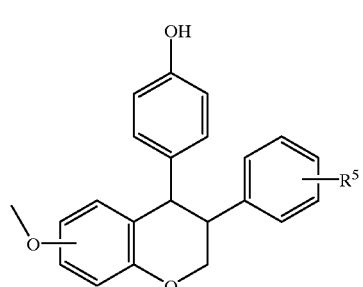

(VI)

wherein R⁵ is as defined above, d) alkylating a compound of the formula (VI) with an appropriate electrophile to form a compound of the formula (VII)

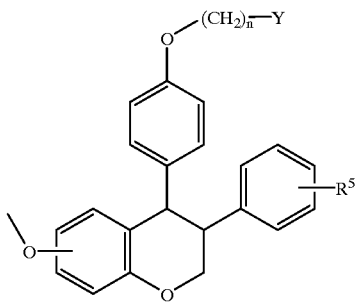

(VII)

wherein n, R⁵ and Y are as defined above, e) deprotecting a compound of formula (VII) with a suitable deprotection agent, preferably by pyridine hydrochloride fusion, to form a compound of the formula (I); or f) nitrating a compound of the formula (VI) with a suitable nitration agent to form a compound of the formula (VIII)

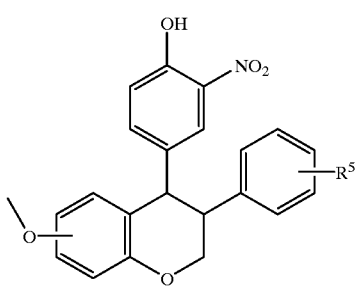

(VIII)

wherein R⁵ is as defined above, g) reducing a compound of the formula (VIII) with a suitable reducing agent, preferably by catalytic hydrogenation, to form a compound of the formula (IX)

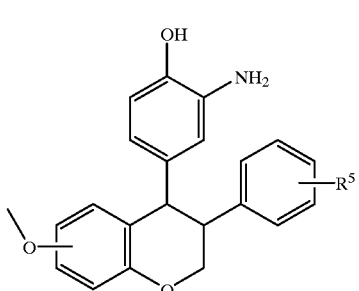

(IX)

wherein R⁵ is as defined above, h) cyclizing a compound of formula (IX) with an appropriate agent to form a compound of the formula (X) or (XI)

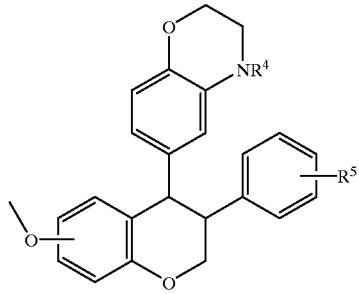

or

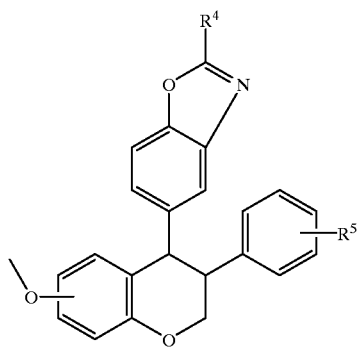

wherein R⁴ and R⁵ are as defined above, i) deprotecting a compound of the formula (X) or (XI) with a suitable deprotection agent, preferably by pyridine hydrochloride fusion, to form a compound of the formula (I); or j) reacting a compound of formula (VI) with trifluoromethane sulphonic acid anhydride to form a compound of the formula (XII)

(XII)

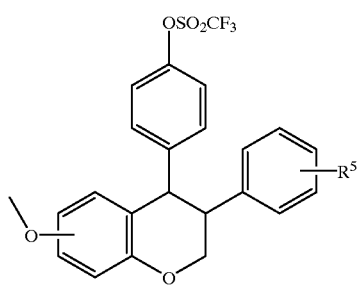

wherein R⁵ is as defined above, k) cross-coupling a compound of the formula (XII) with the appropriate cross-coupling partner to form a compound of the formula (XIII)

(XIII)

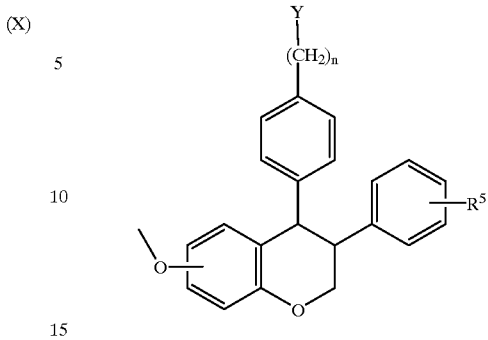

wherein n, R⁵ and Y are as defined above, l) deprotecting a compound of the formula (XIII) with a suitable deprotection agent, preferably by pyridine hydrochloride fusion, to form a compound of the formula (I); or m) cyclizing a compound of the formula (XIV)

(XIV)

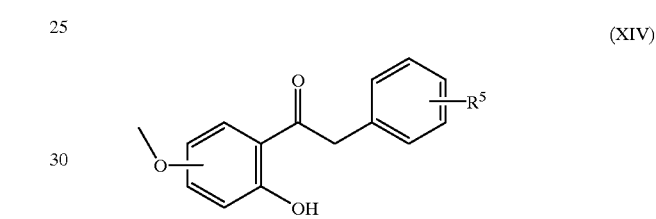

wherein R⁵ is as defined above, with paraformaldehyde in the presence of dimethylamine to form a compound of the formula (XV)

(XV)

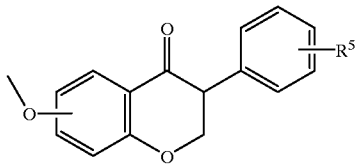

wherein R⁵ is as defined above, n) reacting a compound of the formula (XV) with the appropriate Grignard reagent to form a compound of the formula (XVI)

(XVI)

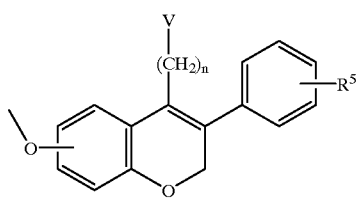

wherein n, R⁵ and V are as defined above, o) hydrogenating a compound of the formula (XVI) in the presence of a suitable catalyst to form a compound of the formula (XVII) with a 3,4-cis configuration (XVII)

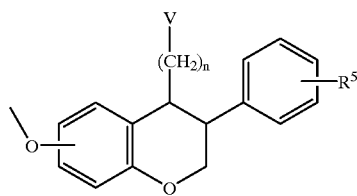

wherein n, $R^5$ and V are as defined above, p) deprotecting a compound of formula (XVII) with a suitable deprotection agent, preferably by pyridine hydrochloride fusion, to form a compound of the general formula (I), q) reacting a compound of the formula (VI) with methanesulfonylchloride to form a compound of the formula (XVIII)

(XVIII)

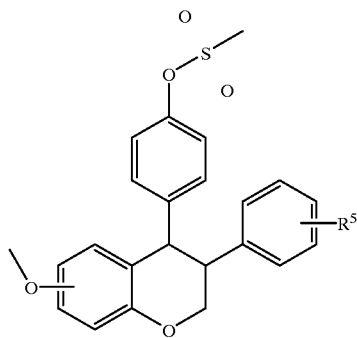

wherein $R^5$ is defined as above, r) deprotecting a compound of the formula (XVIII) with a suitable deprotection agent, such as pyridine hydrochloride fusion or boron tribromide, to form a compound of the formula (XIX)

(XIX)

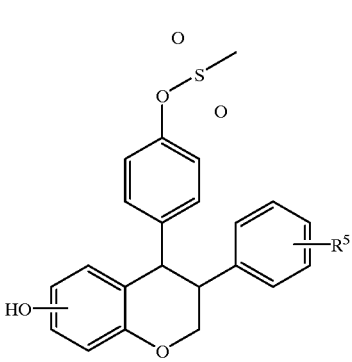

wherein $R^5$ is defined as above, s) reacting a compound of the formula (XIX) with a suitable protection agent, such as benzyl bromide or 4-methoxybenzyl bromide, to form a compound of formula (XX)

(XX)

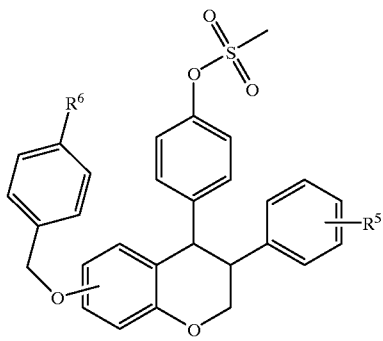

wherein $R^5$ is defined as above, and $R^6$ is H or methoxy, t) deprotecting a compound of the formula (XX) with a suitable deprotection agent, such as sodium or potassium hydroxide in alcohol, to form a compound of formula (XXI)

(XXI)

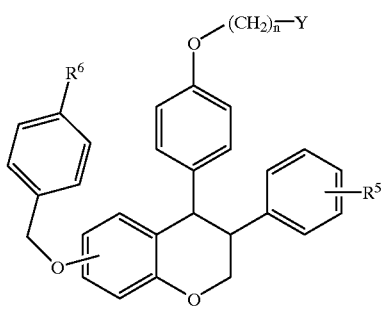

wherein $R^5$ is defined as above, and $R^6$ is H or methoxy, u) alkylating a compound of the formula (XXI) with an appropriate electrophile to form a compound of the formula (XXII)

(XXII)

wherein n, $R^5$ and Y is defined as above, and $R^6$ is H or methoxy, v) deprotecting a compound of the formula (XXII) with a suitable deprotection agent, preferably catalytic hydrogenation for $R^6$ equals H or a strong acid for $R^6$ equals methoxy, to form a compound of the formula (XXIII)

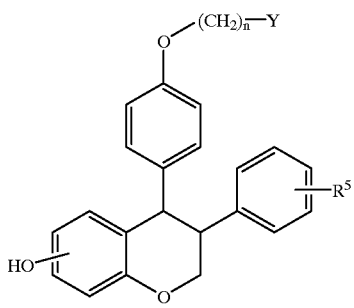

(XXIII)

wherein n, $R^5$ and Y is defined as above, w) Alkylating a compound of the formula (XXI) with an appropriate dihalogenated alkane such as 1,2-dibromoethane, 1-bromo-2-chloroethane, 1,4-dibromobutane, 1,6-dibromohexane, 1,8-dibromooctane, 1,10-dibromodecane, preferably catalysed by potassium iodide, to form a compound of the formula (XXIV)

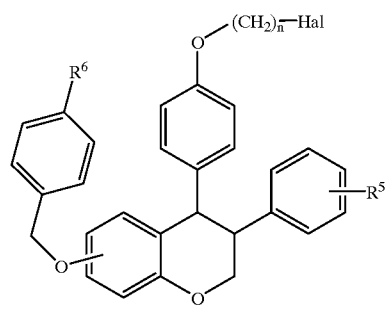

(XXIV)

wherein n and $R^5$ is defined as above, $R^6$ is H or methoxy, and Hal is chloro, bromo, or iodo, x) reacting a compound of the formula (XXIV) with an appropriate nucleophile, preferably an amine, to form a compound of the formula (XXV)

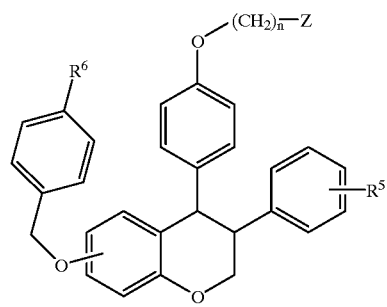

(XXV)

wherein n and $R^5$ is defined as above, $R^6$ is H or methoxy, and Z is a $C_3$–$C_7$ heterocyclic amine optionally containing oxygen or nitrogen, optionally being substituted with 1 to 3 substituents independently selected from the group consisting of H, OH, halogen, nitro, cyano, trihalo-$C_1$–$C_6$-alkyl, $C_1$–$C_6$-alkyl and $C_1$–$C_6$-alkoxy, y) deprotecting a compound of the formula (XXV) with a suitable deprotection agent, preferably catalytic hydrogenation for $R^6$ equals H or a strong acid for $R^6$ equals methoxy, to form a compound of the formula (XXVI)

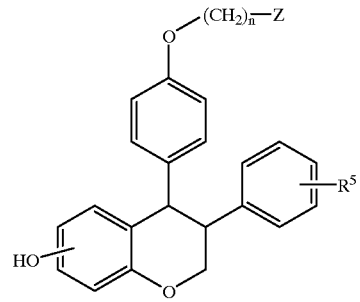

(XXVI)

wherein n and $R^5$ is defined as above, $R^6$ is H or methoxy, and Z a $C_3$–$C_7$ heterocyclic amine optionally containing oxygen or nitrogen, optionally being substituted with 1 to 3 substituents independently selected from the group consisting of H, OH, halogen, nitro, cyano, trihalo-$C_1$–$C_6$-alkyl, $C_1$–$C_6$-alkyl and $C_1$–$C_6$-alkoxy.

The starting benzophenones of the formula (II) are easily prepared via Friedel-Craft acylation of the appropriate dimethyl ether with p-hydroxybenzoic acid followed by selective monodemethylation with hydrobromic acid in acetic acid.

The starting deoxybenzoins of the formula (XIV) are easily prepared via the Hoesch reaction of the appropriate dimethyl ether and the appropriate substituted phenyl acetic acid derivative followed by selective monodemethylation by hydrobromic acid in acetic acid.

Optical pure compounds of formula (I) can be obtained by introducing in the above method a resolution step. The resolution can be carried out after any step of the process which results in a racemic mixture of enantiomers. Any resolution technique may be used to separate a (−)-enantiomer and/or a (+)-enantiomer from a racemic mixture, including diastereomeric salt formation and chiral HPLC.

The expression "appropriate electrophile" typically means an alkylhalogenide of the formula Y—$(CH_2)$n-Hlg, wherein Y is as defined above and Hlg is Cl, Br or I.

The cyclization step of the above method can be performed with for example a suitable activated carboxylic acid derivative followed by dehydration.

The expression "appropriate cross-coupling partner" typically means an organometallic reagent together with a transition metal catalyst, for example a Grignard reagent with a Ni(0) catalyst.

The expression "appropriate Grignard reagent" typically means an organometallic compound of the formula M—$(CH_2)$—Y, wherein M is MgHlg, Hlg is Cl, Br or I and Y is as defined above.

The present invention also relates to pharmaceutical compositions comprising an effective amount of a compound according to the invention and a pharmaceutical carrier or diluent. Such compositions are preferably in the form of an oral dosage unit or parenteral dosage unit.

Furthermore, the invention is concerned with a method of treating or preventing estrogen related diseases or syndromes, preferably diseases or syndromes caused by an estrogen-deficient state in a mammal, comprising administering to a subject in need thereof an effective amount of a compound according to the invention.

The compounds of this invention are new estrogen agonists and are useful for prevention and treatment of bone loss, prevention and treatment of osteoporosis; the prevention and treatment of cardiovascular disease; treatment and prevention of physiological disorders associated with an excess of neuropeptide Y (e.g. obesity, depression, etc.); and for regulation of glucose metabolism in e.g. non-insulin dependent diabetes melitus; and the prevention and treatment of senile dementia-Alzheimer's type in women. In addition, these estrogen agonists are useful for oral contraception; relief of menopausal symptoms (e.g. hot flushes, urogenital atrophy, depression, mania, schizophrenia, etc.); incontinence; prevention of threatened or habitual abortion; relief of dysmenorrhea; relief of dysfunctional uterine bleeding; an aid in ovarian development; treatment of acne; diminution of excessive growth of body hair is women (hirsutism); treatment of prostatic carcinoma; and the suppression of post-partum lactation. These agents also lower serum cholesterol and have a beneficial effect on plasma lipid profiles.

While the compounds of this invention are estrogen agonists in bone and cardiovascular tissues, they are also capable of acting as antiestrogens in other estrogen target organs. For example, these compounds can act as antiestrogens in breast tissue and the colon and therefore would be useful for the prevention and treatment of estrogen-dependent cancers such as breast cancers and colon cancers.

In vitro Estrogen Receptor Binding Assay

An in vitro receptor binding assay was used to determine the estrogen receptor binding affinity of the compounds of this invention. This assay measures the ability of the compounds of this invention to displace $^3$H-17$\beta$-estradiol (17$\beta$-E2), from estrogen receptor (ER) obtained from rabbit uterus. Experimentally, the ER rich cytosol from rabbit uterine tissue is diluted with ER poor cytosol isolated from rabbit muscle to achieve approximately 20–25% maximal binding of 0.5 nM $^3$H-17$\beta$-E2. For each assay, fresh aliquots of cytosol are thawed on the day of analysis and diluted with assay buffer to ca. 3 mg cytosol protein/ml. The assay buffer (PB) is as follows: 10 mM $K_2HPO_4$/$KH_2PO_4$, 1.5 mM $K_2EDTA$, 10 mM monothioglycerol, 10 mM $Na_2MoO_4 \cdot 2H_2O_1$ 10% glycerol (v/v); pH 7.5. Radio-inert 17$\beta$-E2 is obtained from Sigma.

Test solutions are prepared in appropriate solvents (ethanol or DMSO) at a concentration of 8×10-3M and serial dilutions prepared with PB or DMSO. Aliquots of 10 $\mu$l are incubated in duplicate for each concentration tested in microtitre plates to which have been added 20 $\mu$l $^3$H-17$\beta$-E2 (assay concentration equals 0.4 nM) and 50 $\mu$l cytosol. For control samples as well as maximal binding sample, 10 $\mu$l PB is added in lieu of test compound.

Following an 18–20 hr incubation at 4° C. the reaction is terminated with 100 $\mu$l DCC slurry [0.5% activated charcoal (Sigma) and 0.005% Dextran T70 (Pharmacia) in PB] added to each sample and incubated with continuous shaking for 15 min at 4° C. DCC background counts are assessed using 50 $\mu$l of 0.3% BSA in PB in lieu of cytosol.

To separate bound and free $^3$H-17$\beta$-E2, Titertek plates are centrifuged for 10 min (800×g) at 4° C. and aliquots of 100 $\mu$l are removed from each sample for scintillation counting using Optiflour scintillation liquid. Standard and control samples are incubated in quadruplicate, while test compounds are incubated in duplicate. The mean counts per minute (cpm) in each sample is calculated, background (DCC) is subtracted, and the percent of maximal 3H-17$\beta$-E2 binding is determined. Individual cpm's are plotted against their respective concentrations of test compound (logarithmic scale), and the IC50 expressed as the compound concentration required to displace 50% of the maximal binding.

Bone Mineral Density

Bone mineral density (BMD) as a measure of bone mineral content (BMC) accounts for greater than 80% of a bone's strength. The loss of BMD with ageing and the accelerated loss following the menopause reduce the strength of the skeleton and render specific sites more susceptible to fracture; i.e. most notably the spine, wrist and hip. True bone density can be measured gravimetrically using Archimede's Principle (an invasive technique). The BMD can also be measured non-invasively using dual energy x-ray absorptiometry (DEXA). In our laboratory, we have utilized a gravimetric method to evaluate changes in BMD due to estrogen deficiency in ovariectomized rodents. Following ovariectomy (the surgical removal of the ovaries), the animals are treated with vehicle, 17$\beta$-E2 as a positive control, and/or other estrogen agonists. The objective of these investigations is to evaluate the ability of the compounds of this invention to prevent bone loss in rodent models of human disease.

Female Sprague-Dawley rats (ca. 3 to 5 months old), or female Swiss-Webster mice (ca. 3 to 5 months old) underwent bilateral ovariectomy or sham surgery. Following recovery from anesthesia the animals are randomized to the following groups, minimum of 8 animals per group:

sham animals treated with vehicle;

ovariectomized animals treated with vehicle;

ovariectomized animals treated with 25 $\mu$g estradiol/kg; and ovariectomized animals treated with 200 $\mu$g/kg of test compound.

All compounds are weighed and dissolved in vehicle solvent in sterile saline and the animals are treated daily via subcutaneous injections for 35 days. At the conclusion of the 35 day protocol, the animals are sacrificed and the femora are excised and cleaned of adherent soft tissue. In rats, the distal 1 cm of the defleshed femora are removed with a diamond wheel cut-off saw and fixed in 70% ethyl alcohol (in mice the distal 0.5 cm are removed and fixed). Following fixation in 70% ethyl alcohol (EtOH) an automated tissue processor was used to dehydrate the bone specimens in an ascending series of alcohol to 100%. The dehydration program was followed by defatting in chloroform and rehydration in distilled water. All automated tissue processing occurred under vacuum. The hydrated bones were weighed in air and weighed while suspended in water on a Mettler balance equipped with a density measurement kit. The weight of each sample in air is divided by the difference between the air weight and the weight in water to determine total bone density; i.e. organic matrix plus mineral per unit volume of tissue. After the determination of total bone density the samples are ashed overnight in a muffle furnace at 600° C. The mineral density can then be determined by dividing the ash weight of each sample by the tissue volume (i.e. air weight-weight suspended in water). The mean bone densities (total and mineral bone densities) are calculated for each group and statistical differences from the vehicle-treated and estrogen-treated controls are determined using computerized statistical programs.

Cholesterol Lowering Activity

The effects of the compounds of the present invention on the serum levels of total cholesterol were measured either in blood samples taken from the animals in the bone density studies described above or from ovariectomized female rats or mice that had been treated with compound for a period of not less than 28 days. In each type of experiment, blood from treated animals was collected via cardiac puncture and placed in a tube containing 30 $\mu$l of 5% EDTA/1 ml of blood. Following centrifugation at 2500 rpm for 10 minutes at 20° C. the plasma was removed and stored at −20° C. until assayed. Cholesterol was measured using a standard enzymatic determination kit purchased from Sigma Diagnostics (Kit No. 352).

Pharmaceutical Preparations

The compounds of the invention, together with a conventional adjuvant, carrier or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of a compound of the invention commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparation, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 10–100 mg/day, when administered to patients, e.g. humans, as a drug.

A typical tablet which may be prepared by conventional tabletting techniques contains:

| | |
|---|---|
| Active compound | 5.0 mg |
| Lactosum | 67.0 mg Ph. Eur. |
| Avicel ™ | 31.4 mg |
| Amberlite ™ IRP 88 | 1.0 mg |
| Magnesii stearas | 0.25 mg Ph. Eur. |

The compounds of the invention may be administered to a subject, e.g., a living animal body, including a human, in need of a compound of the invention, and if desired in the form of a pharmaceutically acceptable acid addition salt thereof (such as the hydrobromide, hydrochloride, or sulphate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an amount which is effective for the treatment of the disease. Suitable dosage ranges are 1–200 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The invention is explained more in detail in the below examples, which illustrates the invention. It is not to be considered as limiting the scope of the invention being defined by the appended claims.

EXAMPLE 1 cis-7-Hydroxy-3-phenyl-4-{4-{2-(pyrrolidin-1-yl)ethoxy}phenyl}chromane

Step 1

4-(4-Hydroxyphenyl)-7-methoxy-3-phenyl-3-chromene 4-(4-Acetoxyphenyl)-7-methoxy-3-phenyl-coumarin (180 g) was dissolved in toluene (2.1 l) at 70° C. and added to a suspension of lithium aluminium hydride (35.4 g) in tetrahydrofuran (2.1 l). The reaction mixture was kept below 60° C. during the addition. The reaction mixture was cooled down to room temperature. Water (45 ml) was carefully added and then 5 M hydrochloric acid (1.2 l). The mixture was heated to 60–65° C. and stirred at for 3 hours. The organic phase was separated. The aqueous phase was extracted with toluene (250 ml). The combined organic phase was washed with water (250 ml) and evaporated to an oil. The oil was dissolved in boiling ethanol (600 ml). The solution was cooled and water was slowly added (400 ml) and the mixture was seeded. The crystals were filtered off, washed with water/ethanol; 25/75 (200 ml) and dried.

Yield 126 g (81%) of 4-(4-Hydroxyphenyl)-7-methoxy-3-phenyl-3-chromene. M.p. 156–157° C. The product was identified by $^1$H-NMR and elemental analysis.

Step 2 cis-4-(4-Hydroxyphenyl)-7-methoxy-3-phenylchromane 4-(4-Hydroxyphenyl)-7-methoxy-3-phenyl-3-chromene (77.7 g) was dissolved in ethanol (1500 ml) at 50° C. Palladium on carbon, 10%, 50% wet (6 g) was added to the solution and the mixture was hydrogenated at 55° C. and 1 atmosphere for 8 hours.

The catalyst was filtered off, while the suspension was warm, and the filtrate evaporated to an oil which solidified during the evaporation.

Yield 74.3 g (95%), m.p. 188–190° C. The product was identified by $^1$H-NMR and elemental analysis.

Step 3 cis-7-Methoxy-3-phenyl-4-{4-[2-(pyrrolidin-1-yl)ethoxy]phenyl}chromane cis-4-(4-Hydroxyphenyl)-7-methoxy-3-phenylchromane (74.3 g) was dissolved in a mixture of toluene (700 ml), water (12 ml) and sodium hydroxide (24.3 g) by heating the mixture to 75° C. 2-Chloroethylpyrrolidin hydrochloride (46.2 g) was added in six portions at 75° C. with half an hour between each portion. After the last addition the mixture was heated at 75° C. for 4 hours. Water (1000 ml) was added and the mixture stirred until all salt was dissolved. The aqueous phase was separated and extracted with another portion of toluene (300 ml). The combined organic phases was dried over potassium carbonate and evaporated to an oil. The oil was dissolved in refluxing methanol (1000 ml) and the product crystallised by cooling in an ice bath.

Yield 79.6 g (83%), m.p. 113–114° C. The product was identified by $^1$H-NMR and elemental analysis.

Step 4 cis-7-Hydroxy-3-phenyl-4-{4-[2-(pyrrolidin-1-yl)ethoxy]phenyl}chromane hydrochloride cis-7-Methoxy-3-phenyl-4-{4-[2-(pyrrolidin-1-yl)ethoxy]phenyl}chromane (4 g) was dissolved in melted pyridinium chloride, prepared from a mixture of pyridine (20 ml) and conc. hydrochloric acid (21 ml) where the water was removed by distillation at 140° C. The mixture was heated at 140° C. for 3 hours and then at 150° C. for 6 hours. The mixture was cooled down to 100° C. Water was added (30 ml) and the mixture was cooled down to 30° C. Toluene (30 ml) and sodium hydroxide (32,5%) to pH 12 was added. The mixture emulsified and was again made pH 3 with conc. hydrochloric acid. The hydrochloride of cis-7-hydroxy-3-phenyl-4-{4-[2-(pyrrolidin-1-yl)ethoxy]phenyl}chromane precipitated as a sticky product. It was dissolved in ethanol (200 ml) and water (10 ml), treated with active carbon, filtered and evaporated. Redissolved in ethanol (50 ml) and water until dissolved at 79° C. The product crystallised when the solution was cooled down to room temperature.

Yield 1.2 g (28%), m.p. 243–245° C. under slight decomposition. The product was identified by $^1$H-NMR and elemental analysis.

EXAMPLE 2

(+)-cis-7-Hydroxy-3-phenyl-4-{4-{2-(pyrrolidin-1-yl)ethoxy}phenyl}chromane

Step 1

(+)-cis-7-Methoxy-3-phenyl-4-{4-[2-(pyrrolidin-1-yl)ethoxy]phenyl}chromane-(+)-O,O'-ditoluoyltartrate cis-7-Methoxy-3-phenyl-4-{4-[2-(pyrrolidin-1-yl)ethoxy]phenyl}chromane (21.5 g) was dissolved in 2-propanol (300 ml with (+)-O,O'ditoluoyltartaric acid (19.3 g). The mixture was stirred at ambient temperature overnight. The precipitate was filtered off. The crystals were recrystallised 5 times from 2-propanol (300 to 150 ml). The enantiomeric purity was determined by Chiral HPLC to be better than 96.7%. Chiral HPLC system: Column: ChiraDex 5μ, 250×4 mm (Merck). Eluent: 70% methanol/buffer (0.25% triethylammonium acetate, pH=5.2). Flow: 0,5 ml/min. Detector: UV 220 nm.

Yield 2.7 g (13%), m.p. 93–96° C.

The product was identified by $^1$H-NMR and elemental analysis. The compound crystallised with half a mole of crystal bound 2-propanol.

Step 2

(+)-cis-7-Hydroxy-3-phenyl-4-{4-[2-(pyrrolidin-1-yl)ethoxy]phenyl}chromane

The base was liberated from (+)-cis-7-methoxy-3-phenyl-4-{4-[2-(pyrrolidin-1-yl)ethoxy]-phenyl}chromane (+)-O,O'-ditoluoyltartrate (2,5 g) by dissolving in a mixture of toluene (30 ml) and water (30 ml) made alkaline (pH=9–10) with sodium hydroxide (2 ml, 32.5%). The aqueous phase was extracted with another portion of toluene (20 ml). The combined organic phase was dried over potassium carbonate and evaporated. The oil was dissolved in pyridine (20 ml). Concentrated hydrochloric acid (24 ml) was added and the water removed from the mixture by distillation until the bottom temperature in the reaction vessel reached 150° C. The heating was maintained for 5 hours. The mixture was cooled down to room temperature, water (30 ml) and toluene (30 ml) was added and the mixture made alkaline (pH=10) with sodium hydroxide (32.5%). The organic phase was separated and the aqueous phase was extracted with another portion of toluene (30 ml). The combined organic phases was dried over potassium carbonate and evaporated. The oil was dissolved in ethanol (100 ml), made pH=2 with conc. hydrochloric acid. The solution was neutralised with sodium hydroxide to pH=7. The precipitate was filtered off and washed with ethanol and washed thoroughly with water.

Yield 0.4 g (31%), m.p. 219–221° C., $[\alpha]_D^{20}=+331°$ (c=0.989% in ethanol/3M HCl, 80/20). The enantiomeric purity of the product was verified by Chiral HPLC to be better than 98%. Chiral HPLC system: Column: ChiraDex 5μ, 250×4 mm (Merck); Eluent: 70% methanol/buffer (0.25% triethylammonium acetate, pH=5.2). Flow: 0.5 ml/min. Detector: UV 220 nm.

The product was identified by $^1$H-NMR and elemental analysis.

EXAMPLE 3

(−)-cis-7-Hydroxy-3-phenyl4-{4-[2-(pyrrolidin-1-yl)ethoxy]phenyl}chromane

Step 1

(−)-cis-7-Methoxy-3-phenyl-4-{4-[2-(pyrrolidin-1-yl)ethoxy]phenyl}chromane-(−)-O,O'-ditoluoyltartrate.

The mother liqueur from the crystallisation of (+)-cis-7-methoxy-3-phenyl-4-{4-[2-(pyrrolidin-1-yl)ethoxy]phenyl}chromane-(+)-O,O'-ditoluoyltartrate was evaporated to an oil. The base was liberated from the (+)-O,O'-ditoluoyltartaric acid by dissolving in toluene (300 ml), water (200 ml) and sodium hydroxide (50 ml, 4 M). The organic phase was washed with water (100 ml), dried over potassium carbonate and evaporated to an oil. The oil was dissolved in 2-propanol (1 l) with (−)-O,O'-ditoluoyltartaric acid (19.8 g). The mixture was stirred overnight and the precipitate was filtered off. The crystals were recrystallised twice from 2-propanol (300 ml).

Yield 6.5 g (31%), m.p. 92–96° C. The enantiomeric purity was determined by Chiral HPLC to be higher than 96.7%. Chiral HPLC system: Column: ChiraDex 5μ, 250×4 mm (Merck). Eluent: 70% methanol/buffer (0.25% triethylammonium acetate, pH=5.2). Flow: 0.5 ml/min. Detector: UV 220 nm.

The product was identified by $^1$H-NMR and elemental analysis. The compound crystallised with a content of half a mole of crystal bound 2-propanol.

Step 2

(−)-cis-7-Hydroxy-3-phenyl-4-{4-[2-(pyrrolidin-1-yl)ethoxy]phenyl}chromane

The base was liberated from (−)-cis-7-methoxy-3-phenyl-4-{4-[2-(pyrrolidin-1-yl)ethoxy]-phenyl}chromane (−)-O,O'-ditoluoyltartrate (6.5 g) by dissolving in a mixture of toluene (30 ml) and water (30 ml) made alkaline (pH=9–10) with sodium hydroxide (32.5%). The aqueous phase was extracted with another portion of toluene (20 ml). The combined organic phase was dried over potassium carbonate and evaporated. The oil was dissolved in pyridine (20 ml). Concentrated hydrochloric acid (24 ml) was added and the water removed from the solution by destillation until the bottom temperature in the reaction vessel reached 147° C. The heating was maintained for 5 hours. The mixture was cooled down to room temperature, water (30 ml) and toluene (30 ml) was added and the mixture made alkaline (pH=10) with sodium hydroxide (32.5%). The organic phase was separated and the aqueous phase was extracted with another portion of toluene (30 ml). The combined organic phase was dried over potassium carbonate and evaporated. The oil was dissolved in toluene (30 ml) at 80° C. cooled an filtered off. The crystals were dissolved in ethanol (200 ml) and water (20 ml) and adjusted until pH=2 with conc. hydrochloric acid. The solution was treated with active carbon, evaporated and redissolved in ethanol (20 ml). A product precipitated, was filtered off and discarded. The filtrate was diluted with ethanol (100 ml) and made pH=7 with sodium hydroxide. The precipitate was filtered off and washed thoroughly with water.

Yield 0.9 g (27%), m.p. 221–223° C., $[\alpha]^{20}_D = -283°$ (c=1.004% in ethanol/3M HCl, 80/20). The enantiomeric purity of the product was verified by Chiral HPLC to be higher than 99%. Chiral HPLC system: Column: ChiraDex 5μ, 250×4 mm (Merck). Eluent: 70% methanol/buffer (0.25% triethylammonium acetate, pH=5.2). Flow: 0.5 ml/min. Detector: UV 220 nm. The product was identified by $^1$H-NMR and elemental analysis.

EXAMPLE 4

(+)-cis-7-Hydroxy-4-(4-(2-pyrrolidinoethoxy) phenyl)-3-(4-(trifluoromethyl)phenyl)-chromane Step 1

4-(4-Acetoxyphenyl)-7-methoxy-3-(4-(trifluoromethyl) phenyl)coumarin

A mixture of (2-hydroxy-4-methoxyphenyl)-(4-hydroxyphenyl)-methanone (7.33 g, 30.0 mmol), acetic anhydride (15 ml), triethylamine (5.5 ml, 39.5 mmol), and 4-(trifluoromethyl)phenyl acetic acid (4.63 g, 30.0 mmol) was stirred at 135° C. for 18 h, and the resulting orange coloured solution poured into water (120 ml) and stirred for 3 h. The resulting mixture of aqueous solution plus sticky solid was diluted with ethyl acetate (300 ml) to dissolve the solid, and the organic layer separated. The aqueous phase was further extracted with ethyl acetate (2×100 ml). The combined organic extracts were washed with water, saturated sodium chloride solution, dried over sodium sulfate and evaporated to give a yellow/orange solid, which was recrystallised from 6:1 ethanol/water (350 ml) to give the product as a colourless solid, which was vacuum dried.

Yield 9.56 g (70%) of 4-(4-acetoxyphenyl)-7-methoxy-3-(4-(trifluoromethyl)phenyl)-coumarin. M.p. 198–201° C. (aqueous ethanol). $^1$H-NMR (CDCl$_3$, 300 MHz) δ: 2.31 (s, 3H), 3.90 (s, 3H), 6.79 (dd, 1H), 6.93 (d, 1H), 7.05–7.15 (m, 4H), 7.17 (d, 1H), 7.21–7.27 (m, 2H), 7.42–7.49 (m, 2H). LRMS (EI) 454 (M$^+$), 412, 384, 369, 43. Elemental analysis: calculated for $C_{25}H_{17}F_3O_5$; C, 66.08; H, 3.77%; found C, 66.04; H, 3.77%.

Step 2

4-(4-Hydroxyphenyl)-7-methoxy-3-(4-(trifluoromethyl) phenyl)chrom-3-ene

Lithium aluminium hydride (0.76 g, 20.03 mmol) was added in small portions to a stirred tetrahydrofuran (200 ml) solution of 4-(4-acetoxyphenyl)-7-methoxy-3-(4-(trifluoromethyl)phenyl)-coumarin (4.54 g, 9.99 mmol). After complete addition, the mixture was stirred at room temperature for 30 min., then treated dropwise with 6M hydrochloric acid (30 ml). The resulting mixture was heated to 60–65° C. for 3 h, cooled and diluted with water (100 ml) and ethyl acetate (50 ml). The aqueous layer was separated and further extracted with ethyl acetate (3×100 ml). The combined organic solutions were washed with saturated aqueous sodium chloride, dried over sodium sulfate and evaporated to give an orange solid. This was recrystallised from ethanol/water (65 ml, 10:3) to give the first crop of solid product as colourless needles. The mother liquors were evaporated to give an orange gum, which was subjected to a second aqueous ethanol recrystallisation to give a second crop of colourless needles. The solids were combined and vacuum dried.

Yield 3.59 g (91%) of 4-(4-hydroxyphenyl)-7-methoxy-3-(4-(trifluoromethyl)phenyl)-chrom-3-ene. M.p. 169–171° C. $^1$H-NMR (CDCl$_3$, 300 MHz) δ: 3.80 (s, 3H), 4.85 (bs, 1H) 5.05 (s, 2H), 6.42 (dd, 1H), 6.52 (d, 1H), 6.72–6.82 (m, 3H), 6.96 (dm, 2H), 7.07 (dm, 2H), 7.40 (dm, 2H). LRMS (EI) 398 (M$^+$), 305 (M—PhOH), 253 (M—PhCF$_3$). Elemental analysis: calculated for $C_{23}H_{17}F_3O_3$; C, 69.34; H, 4.30%; found C, 69.00; H, 4.27%.

Step 3

(+)-cis-4-(4-Hydroxyphenyl)-7-methoxy-3-(4-(trifluoromethyl)phenyl)chromane

Palladium on carbon (10%, 0.40 g, 0.4 mmol) was added to a stirred solution of 4-(4-hydroxyphenyl)-7-methoxy-3-(4-(trifluoromethyl)phenyl)chrom-3-ene (2.99 g, 7.51 mmol) in ethanol, (100 ml) and the mixture hydrogenated at room temperature for 24 h. The catalyst was removed by filtration, and the solvent evaporated to give an off-white solid which was purified by recrystallisation from 50 ml ethanol. This gave the first crop of product as colourless needles. The mother liquors were evaporated and the recrystallisation repeated from aqueous ethanol, to give a second crop of colourless needles. The solids were combined and vacuum dried.

Yield 2.52 g (82%) of (±)-cis-4-(4-hydroxyphenyl)-7-methoxy-3-(4-(trifluoromethyl)phenyl)chromane. M.p. 211–213° C. $^1$H-NMR (CDCl$_3$, 300 MHz) δ: 3.63 (ddd, 1H), 3.81 (s, 3H), 4.20–4.28 (m, 2H), 4.44 (dd, 1H), 4.60 (bs, 1H), 6.43–6.58 (m, 6H), 6.79 (dm, 2H), 6.84 (d, 1H), 7.41 (dm, 2H). LRMS (EI) 400 (M$^+$), 227, 211. Elemental analysis: calculated for $C_{23}H_{19}F_3O_3$: C, 68.99; H, 4.78%; found C, 69.06; H, 4.78%.

Step 4

(±)-cis-7-methoxy-4-(4-(2-pyrrolidinoethoxy)phenyl)-3-(4-(trifluoromethyl)-phenyl)chromane A mixture of (±)-cis-4-(4-hydroxyphenyl)-7-methoxy-3-(4-(trifluoromethyl)phenyl)chroman (0.801 g, 2.00 mmol), potassium carbonate (2.76 g, 19.97 mmol), sodium iodide (0.01 g, 0.07 mmol), 1-(2-chloroethyl)pyrrolidine hydrochloride, (0.38 g, 2.23 mmol) and acetone, (100 ml) was stirred at 60° C., under reflux, for 24 h. The resulting mixture was filtered and the solvent evaporated to give a colourless gum, which solidified on cooling. The crude solid was recrystallised from 20 ml ethanol to give the product as colourless needles, which contained 0.5 equivalents of ethanol of crystallisation after vacuum drying.

Yield 0.926 g (88%) of (±)-cis-7-methoxy-4-(4-(2-pyrrolidinoethoxy)phenyl)-3-(4-(trifluoromethyl)phenyl) chromane. M.p. 119–120° C. $^1$H-NMR (CDCl$_3$, 300 MHz) δ: 1.75–1.85 (m, 4H), 2.55–2.65 (m, 4H), 2.85 (t, 2H), 3.62 (ddd, 1H), 3.81 (s, 3H), 4.01 (t, 2H), 4.19–4.28 (m, 2H), 4.44 (dd, 1H), 6.44–6.54 (m, 4H), 6.64 (dm, 2H), 6.78 (d, 1H), 7.40 (dm, 2H). LRMS (EI) 497 (M$^+$), 84 ($C_5H_{10}N$).

Step 5

(±)-cis-7-Hydroxy-4-(4-(2-pyrrolidinoethoxy)phenyl)-3-(4-(trifluoromethyl)-phenyl)chromane A mixture of (±)-cis-7-methoxy-4-(4-(2-pyrrolidinoethoxy)phenyl)-3-(4-(trifluoromethyl)-phenyl) chromane (0.30 g, 0.60 mmol) and anhydrous pyridine hydrochloride (3.50 g, 30.3 mmol) was heated to 150–155° C. as a melt for 18 hours. The mixture was cooled to room temperature, and the resulting orange coloured wax dissolved in a mixture of water (50 ml), hot ethanol (20 ml) and dichloromethane (100 ml). The aqueous layer was basified to pH 14 by adding 10M sodium hydroxide, then 1M hydrochloric acid was added until pH 8–9. The organic layer was collected and the aqueous layer further extracted with dichloromethane (2×75 ml). The combined organics were washed with saturated sodium chloride, dried over magnesium sulfate and evaporated to a dark coloured gum, which was purified by column chromatography on silica gel, with 6% methanol in dichloromethane as eluent, giving the product as a colourless solid.

Yield 0.20 g (68%) of (±)-cis-7-hydroxy-4-(4-(2-pyrrolidinoethoxy)phenyl)-3-(4-(trifluoromethyl)phenyl) chromane. M.p. 100° C. (dec). $^1$H-NMR (CDCl$_3$, 300 MHz) δ: 1.80–1.95 (m, 4H), 2.65–2.82 (m, 4H), 2.82–2.94 (m, 1H), 3.0–3.12 (m, 1H), 3.62 (ddd, 1H), 3.77–4.08 (m, 2H), 4.16 (dd, 1H), 4.21 (d, 1H), 4.38 (dd, 1H), 6.36 (dd, 1H), 6.41 (d, 1H), 6.41–6.45 (m, 4H), 6.72–6.79 (m, 3H), 7.37–7.44 (m, 2H), phenol OH not observed. LRMS (EI) 483 (M$^+$), 84 ($C_5H_{10}N$, 100%). Analytical chiral HPLC: {Chiradex 5 μm, 250×4 mm column; 70% methanol, 30% buffer (0.25% w/w triethylammonium acetate, pH 5.20); 0.5 ml/min flow rate; 220 nm UV detection} enantiomer signals at Rt=22.7 and 38.6 min.

Step 6

(+)-cis-7-hydroxy-4-(4-(2-pyrrolidinoethoxy)phenyl)-3-(4-(trifluoromethyl)phenyl)-chromane The title compound was separated from the racemic mixture, (±)-cis-7-hydroxy4-(4-(2-pyrrolidinoethoxy)phenyl)-3-(4-(trifluoromethyl)phenyl)chromane, by means of preparative chiral HPLC on a Chiradex 5 μm, 250×25 mm column. The title compound was the more rapidly eluted enantiomer.

Yield 25.9 mg of (+)-cis-7-hydroxy-4-(4-(2-pyrrolidinoethoxy)phenyl)-3-(4-(trifluoromethyl)phenyl)chromane. Analytical chiral HPLC: {Chiradex 5 μm, 250×4 mm column; 70% methanol, 30% (0.25% w/w triethylammonium acetate, pH 5.20) eluent; 0.5 ml/min flow; 220 nm UV detection}. Rt=22.7 min, >99% ee. $^1$H-NMR (CDCl$_3$, 300 MHz) δ: 1.80–1.95 (m, 4H), 2.65–2.82 (m, 4H), 2.82–2.94 (m, 1H), 3.0–3.12 (m, 1H), 3.62 (ddd, 1H), 4.01 (t, 2H), 4.16 (dd, 1H), 4.21 (d, 1H), 4.38 (dd, 1H), 6.36 (dd, 1H), 6.41 (d, 1H), 6.41–6.45 (m, 4H), 6.72–6.79 (m, 3H), 7.37–7.44 (m, 2H), phenol OH not observed. $[α]_D^{20}$=+246.2° (c=1.0% in methanol).

EXAMPLE 5

(+)-cis-7-Hydroxy-3-(4-methylphenyl)-4-(4-(2-pyrrolidinoethoxy)phenyl)chromane

The title compound was prepared in a manner exactly analogous to that described for Example 4, with substitution of 4-methylphenyl acetic acid for the 4-(trifluoromethyl)phenyl acetic acid used in Step 1.

Thus (±)-cis-7-methoxy-3-(4-methylphenyl)-4-(4-(2-pyrrolidinoethoxyl)-chromane was de-methylated by heating with pyridine hydrochloride to give the racemic mixture, (±)-cis-7-hydroxy-3-(4-methylphenyl)-4-(4-(2-pyrrolidinoethoxyl)-phenyl)chromane. The title compound was then separated from this racemic mixture by means of preparative chiral HPLC {Chiradex 5 μm, 250×25 mm column; flow=20 ml/min; 50% methanol, 50% buffer (0.2% aqueous triethylammonium acetate, pH 3.5) eluent, 220 nm UV detection}. The title compound was the more rapidly eluted enantiomer, Rt=10–18 min.

Yield 14.7 mg of (+)-cis-7-hydroxy-3-(4-methylphenyl)-4-(4-(2-pyrrolidinoethoxy)-phenyl)chromane. Analytical chiral HPLC: {Chiradex 5 μm, 250×4 mm column; 40% methanol, 60% (0. 1% w/w triethylammonium acetate, pH 4.20) eluent; 0.8 ml/min flow; 220 nm UV detection}. Rt=13.8 min, >99% ee. $^1$H-NMR (MeOH-d$_4$, 300 MHz) δ: 1.78–1.93 (m, 4H), 2.25 (s, 3H), 2.67–2.84 (m, 4H), 2.94 (t, 2H), 3.47 (ddd, 1H), 4.03 (t, 2H), 4.13 (dd, 1H), 4.19 (d, 1H), 4.37 (dd, 1H), 6.30 (dd, 1H), 6.34 (d, 1H), 6.51 (dm, 2H), 6.58 (dm, 2H), 6.62 (dm, 2H), 6.67 (d, 1H), 6.93 (dm, 2H), phenol OH not observed. $[α]_D^{20}$=+303.4° (c=0.62% in methanol).

EXAMPLE 6

(+)-cis-7-Hydroxy-3-(3-hydroxyphenyl)-4-(4-(2-pyrrolidinoethoxy)phenyl)chromane

The title compound was prepared in a manner exactly analogous to that described for Example 4, with substitution of 3-methoxyphenyl acetic acid for the 4-(trifluoromethyl)phenyl acetic acid used in Step 1.

Thus (±)-cis-7-methoxy-3-(3-methoxyphenyl)-4-(4-(2-pyrrolidinoethoxy)phenyl)-chromane was de-methylated by heating with pyridine hydrochloride to give the racemic mixture, (±)-cis-7-hydroxy-3-(3-hydroxyphenyl)-4-(4-(2-pyrrolidinoethoxy)-phenyl)chromane. The title compound was then separated from this racemic mixture by means of preparative chiral HPLC {Chiradex 5 μm, 250×25 mm column; flow =20 ml/min; 40% methanol, 60% buffer (0.2% aqueous triethylammonium acetate, pH 3.5) eluent, 220 nm UV detection}. The title compound was the more rapidly eluted enantiomer, Rt=22–34 min.

Yield 20.9 mg of (+)-cis-7-hydroxy-3-(3-hydroxyphenyl)-4-(4-(2-pyrrolidinoethoxy)-phenyl)chromane. Analytical chiral HPLC: {Chiradex 5 μm, 250×4 mm column; 40% methanol, 60% (0.1% w/w triethylammonium acetate, pH 4.20) eluent; flow=0.8 ml/min; 220 nm UV detection}. Rt=11.4 min, 95.2% ee. $^1$H-NMR (MeOH-d$_4$, 300 MHz) δ: 1.80–1.95 (m, 4H), 2.72–2.90 (m, 4H), 3.00 (t, 2H), 3.44 (ddd, 1H), 4.05 (t, 2H), 4.15 (dd, 1H), 4.21 (d, 1H), 4.34 (dd, 1H), 6.14 (m, 1H), 6.23 (dm, 1H), 6.31 (dd, 1H), 6.34 (d, 1H), 6.50 –6.59 (m, 3H), 6.60–6.71 (m, 3H), 6.93 (dd, 1H), phenol OH signals not observed. $[α]_D^{20}$=+278.0° (c=0.87% in methanol).

EXAMPLE 7

(−)-cis-7-Hydroxy-4-(4-(2-pyrrolidinoethoxy)phenyl)-3-(4-(trifluoromethyl)phenyl)-chromane Step 1

4-(4-Acetoxyphenyl)-7-methoxy-3-(4-(trifluoromethyl)phenyl)coumarin

A mixture of (2-hydroxy-4-methoxyphenyl)-(4-hydroxyphenyl)-methanone (7.33 g, 30.0 mmol), acetic anhydride (15 ml), triethylamine (5.5 ml, 39.5 mmol), and 4-(trifluoromethyl)phenyl acetic acid (4.63 g, 30.0 mmol) was stirred at 135° C. for 18 h, and the resulting orange coloured solution poured into water (120 ml) and stirred for 3 h. The resulting mixture of aqueous solution plus sticky solid was diluted with ethyl acetate (300 ml) to dissolve the solid, and the organic layer separated. The aqueous phase was further extracted with ethyl acetate (2×100 ml). The combined organic extracts were washed with water, saturated sodium chloride solution, dried over sodium sulfate and evaporated to give a yellow/orange solid, which was recrystallised from 6:1 ethanol/water (350 ml) to give the product as a colourless solid, which was vacuum dried.

Yield 9.56 g (70%) of 4-(4-acetoxyphenyl)-7-methoxy-3-(4-(trifluoromethyl)phenyl)-coumarin. M.p. 198–201° C. (aqueous ethanol). $^1$H-NMR (CDCl$_3$, 300MHz)δ: 2.31 (s, 3H), 3.90 (s, 3H), 6.79 (dd, 1H), 6.93 (d, 1H), 7.05–7.15 (m, 4H), 7.17 (d, 1H), 7.21–7.27 (m, 2H), 7.42–7.49 (m, 2H). LRMS (EI) 454 (M$^+$), 412, 384, 369, 43. Elemental analysis: calculated for $C_{25}H_{17}F_3O_5$; C, 66.08; H, 3.77%; found C, 66.04; H, 3.77%.

Step 2

4-(4-Hydroxyphenyl)-7-methoxy-3-(4-(trifluoromethyl)phenyl)chrom-3-ene

Lithium aluminium hydride (0.76 g, 20.03 mmol) was added in small portions to a stirred tetrahydrofuran (200 ml) solution of 4-(4-acetoxyphenyl)-7-methoxy-3-(4-(trifluoromethyl)phenyl)-coumarin (4.54 g, 9.99 mmol). After complete addition, the mixture was stirred at room temperature for 30 min., then treated dropwise with 6M hydrochloric acid (30 ml). The resulting mixture was heated to 60–65° C. for 3 h, cooled and diluted with water (100 ml) and ethyl acetate (50 ml). The aqueous layer was separated and further extracted with ethyl acetate (3×100 ml). The combined organic solutions were washed with saturated aqueous sodium chloride, dried over sodium sulfate and evaporated to give an orange solid. This was recrystallised from ethanol/water (65 ml, 10:3) to give the first crop of solid product as colourless needles. The mother liquors were evaporated to give an orange gum, which was subjected to a second aqueous ethanol recrystallisation to give a second crop of colourless needles. The solids were combined and vacuum dried.

Yield 3.59 g (91%) of 4-(4-hydroxyphenyl)-7-methoxy-3-(4-(trifluoromethyl)phenyl)-chrom-3-ene. M.p. 169–171°C. $^1$H -NMR (CDCl$_3$, 300 MHz) δ: 3.80 (s, 3H), 4.85 (bs, 1H), 5.05 (s, 2H), 6.42 (dd, 1H), 6.52 (d, 1H), 6.72–6.82 (m, 3H), 6.96 (dm, 2H), 7.07 (dm, 2H), 7.40 (dm, 2H). LRMS (EI) 398 (M$^+$), 305 (M—PhOH), 253 (M—PhCF$_3$).$^{31}$ Elemental analysis: calculated for C$_{23}$H$_{17}$F$_3$O$_3$; C, 69.34; H, 4.30%; found C, 69.00; H, 4.27%.

Step 3

(±)-cis-4-(4-Hydroxyphenyl)-7-methoxy-3-(4-(trifluoromethyl)phenyl)chromane

Palladium on carbon (10%, 0.40 g, 0.4 mmol) was added to a stirred solution of 4-(4-hydroxyphenyl)-7-methoxy-3-(4-(trifluoromethyl)phenyl)chrom-3-ene (2.99 g, 7.51 mmol) in ethanol, (100 ml) and the mixture hydrogenated at room temperature for 24 h. The catalyst was removed by filtration, and the solvent evaporated to give an off-white solid which was purified by recrystallisation from 50 ml ethanol. This gave the first crop of product as colourless needles. The mother liquors were evaporated and the recrystallisation repeated from aqueous ethanol, to give a second crop of colourless needles. The solids were combined and vacuum dried.

Yield 2.52 g (82%) of (±)-cis-4-(4-hydroxyphenyl)-7-methoxy-3-(4-(trifluoromethyl)phenyl)chromane. M.p. 211–213° C. $^1$H-NMR (CDCl$_3$, 300 MHz)δ: 3.63 (ddd, 1H), 3.81 (s, 3H), 4.20–4.28 (m, 2H), 4.44 (dd, 1H), 4.60 (bs, 1H), 6.43–6.58 (m 6H), 6.79 (dm, 2H), 6.84 (d, 1H), 7.41 (dm, 2H). LRMS (EI) 400 (M$^{30}$), 227, 211. Elemental analysis: calculated for C$_{23}$H$_{19}$F$_3$O$_3$: C, 68.99; H, 4.78%; found C, 69.06; H, 4.78%.

Step 4

(±)-cis-7-methoxy-4-(4-(2-pyrrolidinoethoxy)phenyl)-3-(4-(trifuoromethyl)-phenyl)chromane A mixture of (±)-cis-4-(4-hydroxyphenyl)-7-methoxy-3-(4-(trifluoromethyl)phenyl)-chromane (0.801 g, 2.00 mmol), potassium carbonate (2.76 g, 19.97 mmol), sodium iodide (0.01 g, 0.07 mmol), 1-(2-chloroethyl)pyrrolidine hydrochloride, (0.38 g, 2.23 mmol) and acetone, (100 ml) was stirred at 60° C., under reflux, for 24 h. The resulting mixture was filtered and the solvent evaporated to give a colourless gum, which solidified on cooling. The crude solid was recrystallised from 20 ml ethanol to give the product as colourless needles, which contained 0.5 equivalents of ethanol of crystallisation after vacuum drying.

Yield 0.926 g (88%) of (±)-cis-7-methoxy-4-(4-(2-pyrrolidinoethoxy)phenyl)-3-(4-(trifluoromethyl)phenyl) chromane. M.p. 119–120° C. $^1$H-NMR (CDCl$_3$, 300 MHz)δ: 1.75–1.85 (m, 4H), 2.55–2.65 (m, 4H), 2.85 (t, 2H), 3.62 (ddd, 1H), 3.81 (s, 3H), 4.01 (t, 2H), 4.19–4.28 (m, 2H), 4.44 (dd, 1H), 6.44–6.54 (m, 4H), 6.64 (dm, 2H), 6.78 (dm, 2H) 6.84 (d, 1H), 7.40 (dm, 2H). LRMS (EI) 497 (M$^+$), 84 (C$_5$H$_{10}$N).

Step 5

(±)-cis- 7-Hydroxy-4-(4-(2-pyrrolidinoethoxy)phenyl)-3-(4-(trifluoromethyl)-phenyl)chromane A mixture of (±)-cis-7-methoxy-4-(4-(2-pyrrolidinoethoxy)phenyl)-3-(4-(trifluoromethyl)phenyl) chromane (0.30 g, 0.60 mmol) and anhydrous pyridine hydrochloride (3.50 g, 30.3 mmol) was heated to 150–155° C. as a melt for 18 hours. The mixture was cooled to room temperature, and the resulting orange coloured wax dissolved in a mixture of water (50 ml), hot ethanol (20 ml) and dichloromethane (100 ml). The aqueous layer was basified to pH 14 by adding 10M sodium hydroxide, then 1M hydrochloric acid was added until pH 8–9. The organic layer was collected and the aqueous layer further extracted with dichloromethane (2×75 ml). The combined organics were washed with saturated sodium chloride, dried over magnesium sulfate and evaporated to a dark coloured gum, which was purified by column chromatography on silica gel, with 6% methanol in dichloromethane as eluent, giving the product as a colourless solid.

Yield 0.20 g (68%) of (±)-cis-7-hydroxy-4-(4-(2-pyrrolidinoethoxy)phenyl)-3-(4-(trifluoromethyl)phenyl) chromane. M.p. 100° C. (dec). $^1$H-NMR (CDCl$_3$, 300 MHz) δ: 1.80–1.95 (m, 4H), 2.65–2.82 (m, 4H), 2.82–2.94 (m, 1H), 3.0–3.12 (m, 1H), 3.62 (ddd, 1H), 3.77–4.08 (m, 2H), 4.16 (dd, 1H), 4.21 (d, 1H), 4.38 (dd, 1H), 6.36 (dd, 1H), 6.41 (d, 1H), 6.41–6.45 (m, 4H), 6.72–6.79 (m, 3H), 7.37–7.44 (m, 2H), phenol OH not observed. LRMS (EI) 483 (M$^+$), 84 (C$_5$H$_{10}$N, 100%). Analytical chiral HPLC: {Chiradex 5 μm, 250×4 mm column; 70% methanol, 30% buffer (0.25% w/w triethylammonium acetate, pH 5.20); 0.5 ml/min flow rate; 220 nm UV detection} enantiomer signals at Rt=22.7 and 38.6 min.

Step 6

(−)-cis- 7-hydroxy-4-(4-(2-pyrrolidinoethoxy)phenyl)-3-(4-(trifluoromethyl)phenyl)-chromane The title compound was separated from the racemic mixture, (±)-cis-7-hydroxy-4-(4-(2-pyrrolidinoethoxy) phenyl)-3-(4-(trifluoromethyl)phenyl)chromane, by means of preparative chiral HPLC on a Chiradex 5 μm, 250×25 mm column. The title compound was the more slowly eluted enantiomer.

Yield 26.5 mg of (−)-cis-7-hydroxy-4-(4-(2-pyrrolidinoethoxy)phenyl)-3-(4-(trifluoromethyl)phenyl) chromane. Analytical chiral HPLC: {Chiradex 5 μm, 250×4 mm column; 70% methanol, 30% (0.25% w/w triethylammonium acetate, pH 5.20) eluent; 0.5 ml/min flow; 220 nm UV detection}. Rt=38.6 min, >99% ee. $^1$H-NMR (CDCl$_3$, 300 MHz) δ: 1.80–1.95 (m, 4H), 2.65–2.82 (m, 4H), 2.82–2.94 (m, 1H), 3.0–3.12 (m, 1H) 3.62 (ddd, 1H), 4.01 (t, 2H), 4.16 (dd, 1H), 4.21 (d, 1H), 4.38 (dd, 1H), 6.36 (dd, 1H), 6.41 (d, 1H), 6.41–6.45 (m, 4H), 6.72–6.79 (m, 3H), 7.37–7.44 (m, 2H), phenol OH not observed. [α]$_D^{20}$=−234.8° (c=1.0% in methanol).

EXAMPLE 8

(−)-cis-7-Hydroxy-3-(4-methylphenyl)-4-(4-(2-pyrrolidinoethoxy)phenyl)chromane

The title compound was prepared in a manner exactly analogous to that described for Example 7, with substitution of 4-methylphenyl acetic acid for the 4-(trifluoromethyl) phenyl acetic acid used in Step 1.

Thus (±)-cis-7-methoxy-3-(4-methylphenyl)-4-(4-(2-pyrrolidinoethoxy)phenyl)-chromane was de-methylated by heating with pyridine hydrochloride to give the racemic mixture, (±)-cis-7-hydroxy-4-(4-methylphenyl)-4-(4-(2-pyrrolidinoethoxy)-phenyl)chromane. The title compound was then separated from this racemic mixture by means of preparative chiral HPLC {Chiradex 5 μm, 250×25 mm column; flow=20 ml/min; 50% methanol, 50% buffer (0.2% aqueous triethylammonium acetate, pH 3.5) eluent, 220 nm UV detection}. The title compound was the more slowly eluted enantiomer, Rt=20–30 min.

Yield 14.7 mg of (−)-cis-7-hydroxy-3-(4-methylphenyl)-4-(4-(2-pyrrolidinoethoxy) -phenyl)chromane. Analytical chiral HPLC: {Chiradex 5 μm, 250×4 mm column; 40% methanol, 60% (0.1% w/w triethylammonium acetate, pH 4.20) eluent; 0.8 ml/min flow; 220 nm UV detection}. Rt=25.9 min, >83.8% ee. $^1$H-NMR (MeOH-d$_4$, 300 MHz)δ: 1.78–1.93 (m, 4H), 2.25 (s, 3H), 2.67–2.84 (m, 4H), 2.94 (t, 2H), 3.47 (ddd, 1H), 4.03 (t, 2H), 4.13 (dd, 1H), 4.19 (d, 1H), 4.37 (dd, 1H), 6.30 (dd, 1H), 6.34 (d, 1H), 6.51 (dm, 2H), 6.58 (dm, 2H), 6.62 (dm, 2H), 6.67 (d, 1H), 6.93 (dm, 2H), phenol OH not observed. [α]$_D^{20}$=−235.6° (c=0.26% in methanol).

EXAMPLE 9

(−)-cis-7-Hydroxy-3-(3-hydroxyphenyl)-4-(4-(2-pyrrolidinoethoxy)phenyl)chromane

The title compound was prepared in a manner exactly analogous to that described for Example 7, with substitution of 3-methoxyphenyl acetic acid for the 4-(trifluoromethyl) phenyl acetic acid used in Step 1.

Thus (±)-cis-7-methoxy-3-(3-methoxyphenyl)-4-(4-(2-pyrrolidinoethoxy)phenyl)-chromane was de-methylated by heating with pyridine hydrochloride to give the racemic mixture, (±)-cis-7-hydroxy-3-(3-hydroxyphenyl)-4-(4-(2-pyrrolidinoethoxy)-phenyl)chromane. The title compound was then separated from this racemic mixture by means of preparative chiral HPLC {Chiradex 5 μm, 250×25 mm column; flow=20 ml/min; 40% methanol, 60% buffer (0.2% aqueous triethylammonium acetate, pH 3.5) eluent, 220 nm UV detection}. The title compound was the more slowly eluted enantiomer, Rt=46–64 min.

Yield 18.5 mg of (−)-cis-7-hydroxy-3-(3-hydroxyphenyl)-4-(4-(2-pyrrolidinoethoxy) -phenyl) chromane. Analytical chiral HPLC: {Chiradex 5 μm, 250×4 mm column; 40% methanol, 60% (0.1% w/w triethylammonium acetate, pH 4.20) eluent; flow=0.8 ml/min; 220 nm UV detection}. Rt=20.4 min, 89.8% ee. $^1$H-NMR (MeOH-$d_4$, 300 MHz)δ: 1.80–1.95 (m, 4H), 2.72–2.90 (m, 4H), 3.00 (t, 2H), 3.44 (ddd, 1H), 4.05 (t, 2H), 4.15 (dd, 1H), 4.21 (d, 1H), 4.34 (dd, 1H), 6.14 (m, 1H), 6.23 (dm, 1H), 6.31 (dd, 1H), 6.34 (d, 1H), 6.50–6.59 (m, 3H), 6.60–6.71 (m, 3H), 6.93 (dd, 1H), phenol OH signals not observed. $[\alpha]_D^{20}=-259.1°$ (c=0.77% in methanol).

EXAMPLE 10

(±)-cis-7-Hydroxy-3-(4-fluorophenyl)-4-(4-(2-pyrrolidinoethoxyl)phenyl)chromane

Step 1

4-(4-Acetoxyphenyl)-3-(4-fluorophenyl)7-methoxy-coumarin

A mixture of (2-hydroxy-4-methoxyphenyl)-(4-hydroxyphenyl)-methanone (7.33 g, 30.0 mmol), acetic anhydride (15 ml), triethylamine (5.5 ml, 39.5 mmol), and 4-fluorophenyl acetic acid (4.63 g, 30.0 mmol) was stirred at 135° C. for 18 h, and the resulting orange coloured solution poured into water (120 ml) and stirred for 3 h. The resulting mixture of aqueous solution plus sticky solid was diluted with ethyl acetate (300 ml) to dissolve the solid, and the organic layer separated. The aqueous phase was further extracted with ethyl acetate (2×100 ml). The combined organic extracts were washed with water, and saturated sodium chloride solution, then dried over sodium sulfate and evaporated to give a yellow/orange solid, which was recrystallised from 2:1 ethanol/water (600ml) to give the product as an off-white solid, which was vacuum dried.

Yield 7.98 g (65%) of 4-(4-acetoxyphenyl)-3-(4-fluorophenyl)-7-methoxy-coumarin. M.p 173–176° C. $^1$H-NMR (CDCl$_3$, 300 MHz)δ: 2.32 (s, 3H); 3.89 (s, 3H); 6.78 (dd, 1H); 6.82–6.95 (m, 3H); 7.03–7.14 (m, 6H); 7.15 (d, 1H). LRMS (EI) 404 (M$^+$), 362, 334, 319, 43. Elemental analysis; calculated for $C_{24}H_{17}FO_5$ : C, 71.28; H, 4.24%; found C, 71.26; H, 4.25%.

Step 2

3-(4-Fluorophenyl)-4-(4-hydroxyphenyl)-7-methoxy-chrom-3-ene

Lithium aluminium hydride (0.76 g, 20.03 mmol) was added in small portions to a stirred tetrahydrofuran (150 ml) solution of 4-(4-acetoxyphenyl)-3-(4-fluorophenyl)-7-methoxy-coumarin (4.04 g, 9.99 mmol). After complete addition, the mixture was stirred at room temperature for 30 min., then treated dropwise with 6M hydrochloric acid (30 ml). The resulting mixture was heated to 60–65° C. for 3 h, cooled and diluted with water (100 ml) and ethyl acetate (50 ml). The aqueous layer was separated and further extracted with ethyl acetate (3×100 ml). The combined organic solutions were washed with saturated aqueous sodium chloride, dried over sodium sulfate and evaporated to give an orange solid. This was recrystallised from ethanol/water (75 ml, 4:1) to give the first crop of solid product as colourless needles. The mother liquors were evaporated to give an orange gum, which was subjected to a second aqueous ethanol recrystallisation to give a second crop of colourless needles. The solids were combined and vacuum dried.

Yield 2.47 g (70%) of 3-(4-Fluorophenyl)-4-(4-hydroxyphenyl)-7-methoxy-chrom-3-ene. M.p. 155–156.5° C. $^1$H -NMR (CDCl$_3$, 300 MHz)δ: 3.79 (s, 3H), 4.80 (bs, 1H), 5.20 (s, 2H); 6.40 (dd, 1H), 6.51 (d, 1H), 6.70–7.00 (m, 9H). LRMS (EI) 348 (M$^+$), 255 (M—PhOH), 253 (M—PhF).

Step 3

(±)-cis-3-(4-Fluorophenyl)-4-(4-hydroxyphenyl)-7-methoxy-chromane

Palladium on carbon (10%, 0.20 g, 0.19 mmol) was added to a stirred solution of 3-(4-fluorophenyl)-4-(4-hydroxyphenyl)-7-methoxy-chrom-3-ene (1.74 g, 4.99 mmol) in ethanol, (150 ml) and the mixture hydrogenated at room temperature for 20 h. The catalyst was removed by filtration, and the solvent evaporated to give an off-white solid which was purified by recrystallisation from aqueous ethanol. This gave the product as a colourless solid, which was vacuum dried to give colourless platelets which contained 0.75 equivalents of ethanol of crystallisation.

Yield 1.29 g (73%) of (±)-cis-3-(4-fluorophenyl)-4-(4-hydroxyphenyl)-7-methoxy-chromane. M.p. 164–165° C. (aqueous ethanol). $^1$H-NMR (CDCl$_3$, 300 MHz)δ: 1.25 (t, 2.4H, 0.75EtOH), 3.55 (ddd, 1H), 3.73 (q, 1.6H, 0.75EtOH), 3.81 (s, 3H), 4.16–4.25 (m, 2H), 4.38 (dd, 1H), 4.90 (bs, 1H), 6.44–6.58 (m, 6H), 6.59–6.68 (m, 2H), 6.80–690 (m, 3H). LRMS (EI) 350 (M$^+$), 227, 211. Elemental analysis: calculated for $C_{22}H_{19}FO_3$.0.75EtOH C, 73.33; H, 6.13%; found C, 73.32; H, 6.11%.

Step 4

(±)-cis-3-(4-Fluorophenyl)- 7-methoxy-4-(4-(2-pyrrolidinoethoxy)phenyl)chromane

A mixture of (±)-cis-3-(4-fluorophenyl)-4-(4-hydroxyphenyl)-7-methoxy-chromane, (0.53 g, 1.51 mmol) potassium carbonate, (2.10 g, 15.2 mmol) sodium iodide, (0.01 g, 0.07 mmol) 1-(2-chloroethyl)pyrrolidine hydrochloride, (0.28 g, 1.65 mmol) and acetone, (35 ml) was stirred at 60° C., under reflux, for 24 h. The resulting mixture was filtered and the solvent evaporated to give a colourless gum, which solidified on cooling. The crude solid was recrystallised from aqueous ethanol to give the product as colourless needles, which were vacuum dried.

Yield 0.57 g (83%) of (±)-cis-3-(4-fluorophenyl)-7-methoxy-4-(4-(2-piperidinoethoxy) -phenyl)chromane. M.p. 93.5–94.5° C. (aqueous ethanol). $^1$H-NMR (CDCl$_3$, 300 MHz)δ: 1.75–1.85 (m, 4H), 2.55–2.65 (m, 4H), 2.85 (t, 2H), 3.55 (ddd, 1H), 3.81 (s, 3H), 4.08 (t, 2H), 4.16–4.23 (m, 2H), 4.37 (dd, 1H), 6.43–6.53 (m, 4H), 6.57–6.66 (m, 4H), 6.80–6.88 (m. 3H). LRMS (EI) 447 (M$^+$), 84 ($C_5H_{10}$N).

Step 5

(±)-cis-7-Hydroxy-3-(4-fluorophenyl)-4-(4-(2-pyrrolidinoethoxy)phenyl)chromane

A mixture of (±)-cis-3-(4-fluorophenyl)-7-methoxy-4-(4-(2-pyrrolidinoethoxy)phenyl) -chromane (0.90 g, 2.01 mmol) and anhydrous pyridine hydrochloride (11.60 g, 100 mmol) was heated to 150–155° C. as a melt for 18 hours. The mixture was cooled to room temperature, and the resulting orange coloured wax dissolved in a mixture of water (100 ml), hot ethanol (20 ml) and dichloromethane (150 ml). The aqueous layer was basified to pH 14 by adding 10M sodium hydroxide, then 1M hydrochloric acid was added until pH 8–9. The organic layer was collected and the aqueous layer further extracted with dichloromethane (2×150 ml). The combined organics were washed with saturated sodium chloride, dried over sodium sulfate and evaporated to a dark coloured gum, which was purified by column chromatography on silica gel, with 7% methanol in dichloromethane as eluent, giving the product as a colourless glass. This was dissolved in a minimum of acetone and petroleum ether added to precipitate the product as an amorphous solid, which was vacuum dried.

Yield 0.632 g (72%) of (±)-cis-7-hydroxy-3-(4-fluorophenyl)-4-(4-(2-pyrrolidinoethoxy)phenyl)chromane. M.p. 164–167° C. (acetone/petrol). $^1$H-NMR (DMSO-$d_6$ 300 MHz)δ: 1.55–1.80 (m, 4H), 2.40–2.60 (m, 4H), 2.70 (t, 2H), 3.50–3.61 (m, 1H), 3.93 (t, 2H), 4.13–4.25 (m, 2H), 4.29 (dd, 1H), 6.25–6.35 (m, 2H), 6.46 (d, 2H), 6.60–6.70 (m, 3H), 6.74–6.81 (m, 2H), 6.98 (t, 2H), 9.30 (s, 1H). LRMS (EI) 433 (M$^+$), 84 ($C_5H_{10}N$).

The following examples were prepared according to the method described above; with substitution of the appropriate functionalized phenyl acetic acid in step 1, and/or the appropriate amino-chloro-alkane electrophile in step 4.

EXAMPLE 11

(±)-cis-7-Hydroxy-3-(4-fluorophenyl)-4-(4-(2-piperidinoethoxy)phenyl)-chromane

In an manner analogous to that described in step 5 for Example 10, (±)-cis-3-(4-fluorophenyl)-7-methoxy-4-(4-(2-piperidinoethoxy)phenyl)chromane (0.923 g, 2.0 mmol) was de-methylated by heating with pyridine hydrochloride to give the title compound as a colourless, amorphous solid.

Yield 0.525 g (58%) of (±)-cis-7-hydroxy-3-(4-fluorophenyl)-4-(4-(2-piperidinoethoxy)phenyl)-chromane. M.p. 146–147° C. (acetone/petrol). $^1$H-NMR (DMSO-$d_6$, 300 MHz)δ: 1.30–1.40 (m, 2H), 1.40–1.55 (m, 4H), 2.35–2.45 (m, 4H), 2.60 (t, 2H) 3.56 (ddd, 1H), 3.93 (t, 2H), 4.18 (dd, 1H), 4.21 (d, 1H), 4.29 (dd, 1H), 6.28 (d, 1H), 6.46 (d, 2H), 6.60–6.69 (m, 3H), 6.78 (dd, 2H), 6.98 (t, 2H), 9.30 (s, 1H). LRMS (EI) 447 (M$^+$), 98 ($C_6H_{12}N$, 100%). Elemental analysis: calculated for $C_{28}H_{30}FNO_3$; C, 75.14; H, 6.76; N, 3.13%; Found C, 75.05; H, 7.02; N, 2.90%.

EXAMPLE 12

(±)-cis-7-Hydroxy-3-(4-fluorophenyl)-4-(4-(3-piperidinopropoxy)phenyl)chromane

In an manner analogous to that described in step 5 for Example 10, (±)-cis-3-(4-fluorophenyl)-7-methoxy-4-(4-(3-piperidinopropoxy)phenyl)chromane (0.476 g, 1.0 mmol) was de-methylated by heating with pyridine hydrochloride to give the title compound as an off-white foam.

Yield 0.264 g (57%) of (±)-cis-7-Hydroxy-3-(4-fluorophenyl)-4-(4-(3-piperidinopropoxy)phenyl)chromane. M.p. 78–84° C. ($CH_2Cl_2$/petrol). $^1$H-NMR (DMSO-$d_6$, 300 MHz)δ: 1.30–1.60 (m, 6H), 1.75–7.90 (m, 2H), 2.30–2.60 (m, 6H), 3.50–3.60 (m, 1H), 3.86 (t, 2H), 4.05–4.35 (m, 3H), 6.25–6.35 (m, 2H), 6.42–6.52 (m, 2H), 6.58–6.69 (m, 3H), 6.73–6.83 (m, 2H), 6.91–7.03 (m, 2H), 9.30 (s, 1H). LRMS (EI) 461 (M$^+$), 98 ($C_6H_{12}N$, 100%).

EXAMPLE 13

(±)-cis-7-Hydroxy-3-phenyl-4-(4-(2-piperidinoethoxy)phenyl)chromane

In an manner analogous to that described in step 5 for Example 10, (±)-cis-7-methoxy-3-phenyl-4-(4-(2-piperidinoethoxy)phenyl)chromane (0.89 g, 2.0 mmol) was de-methylated by heating with pyridine hydrochloride to give the title compound as an off-white solid.

Yield 0.424 g (49%) of (±)-cis-7-Hydroxy-3-phenyl-4-(4-(2-piperidinoethoxy)phenyl)-chromane. M.p. 168–170° C. (aqueous EtOH). $^1$H-NMR (DMSO-$d_6$, 300 MHz)δ: 1.30–1.40 (m, 2H), 1.40–1.55 (m, 4H), 2.35–2.45 (m, 4H), 2.60 (t, 2H), 3.53 (ddd, 1H), 3.72 (t, 2H), 4.15–4.26 (m, 2H), 4.13 (dd, 1H), 6.28 (dd, 1H), 6.31 (d, 1H), 6.44 (d, 2H), 6.61 (d, 2H), 6.66 (d, 1H), 6.71–6.80 (m, 2H), 7.10–7.20 (m, 3H), 9.30 (s, 1H). LRMS (EI) 429 (M$^+$), 98 ($C_6H_{12}N$, 100%). Elemental analysis: calculated for $C_{28}H_{31}NO_3$; C, 78.29; H, 7.27; N, 3.26%; found C, 78.46; H, 7.26; N, 3.21%.

EXAMPLE 14

(±)-cis-7-Hydroxy-3-phenyl-4-(4-(3-piperidinopropoxy)phenyl)chromane

In an manner analogous to that described in step 5 for Example 10, (±)-cis-7-methoxy-3-phenyl-4-(4-(3-piperidinopropoxy)phenyl)chromane (0.114 g, 0.25 mmol) was de-methylated by heating with pyridine hydrochloride to give the title compound as an off-white foam.

Yield 52 mg (47%) of (i)-cis-7-Hydroxy-3-phenyl-4-(4-(3-piperidinopropoxy)phenyl)-chromane. $^1$H-NMR (CDCl$_3$, 300 MHz) δ: 1.45–1.60 (m, 2H), 1.70–1.85 (m, 4H), 2.05–2.20 (m, 2H), 2.65–2.85 (m, 6H), 3.54 (ddd, 1H), 3.86 (t, 2H), 4.14–4.23 (m, 2H), 4.37 (dd, 1H), 6.39 (dd, 1H), 6.42–6.56 (m, 5H), 6.61–6.68 (m, 2H), 6.72 (d, 1H), 6.70–6.90 (bs, 1H), 7.10–7.20 (m, 3H). LRMS (EI) 443 (M$^+$), 98 ($C_6H_{12}N$, 100%).

EXAMPLE 15

(±)-cis-7-Hydroxy-3-(4-hydroxyphenyl)-4-(4-(2-pyrrolidinoethoxy)phenyl)chromane

In an manner analogous to that described in step 5 for Example 10, (±)-cis-7-methoxy-3-(4-methoxyphenyl)-4-(4-(2-pyrrolidinoethoxy)phenyl)chromane (4.60 g, 10.0 mmol) was de-methylated by heating with pyridine hydrochloride to give the title compound as colourless platelets.

Yield 1.59 g (31%) of (±)-cis-7-hydroxy-3-(4-hydroxyphenyl)-4-(4-(2-pyrrolidinoethoxy)phenyl) chromane. M.p. 112–116° C. (acetone/petrol). $^1$H-NMR (MeOH-$d_4$, 300 MHz) δ: 1.85–2.00 (m, 4H), 2.88–3.04 (m, 4H), 3.15 (t, 2H), 3.44 (ddd, 1H), 4.11 (t, 2H), 4.06–4.20 (m, 2H), 4.32 (dd, 1H), 6.29 (dd, 1H), 6.34 (d, 1H), 6.47–6.64–6.72 (m, 3H), phenol OH not observed. LRMS (EI) 431 (M$^+$), 84 ($C_5H_{10}N$, 100%).

EXAMPLE 16

(±)-cis-7-Hydroxy-3-(4-phenyl-phenyl)-4-(4-(2-pyrrolidinoethoxy)phenyl)chromane

In an manner analogous to that described in step 5 for Example 10, (±)-cis-7-methoxy-3-(4-phenyl-phenyl)-4-(4-(2-pyrrolidinoethoxy)phenyl)chromane (0.202 g, 0.399 mmol) was de-methylated by heating with pyridine hydrochloride to give the title compound as an off-white solid.

Yield 43 mg (22%) of (±)-cis-7-hydroxy-3-(4-phenyl-phenyl)-4-(4-(2-pyrrolidinoethoxy)phenyl)chromane. $^1$H-NMR (DMSO-$d_6$, 300 MHz) δ: 1.70–1.90 (m, 4H), 2.90–3.10 (m, 4H), 3.15–3.25 (m, 2H), 3.55–3.65 (m, 1H), 4.05–4.15 (m, 2H), 4.20–4.45 (m, 3H), 6.27–6.37 (m, 2H), 6.50–6.58 (m, 2H), 6.62–6.75 (m, 3H), 6.82–6.90 (m, 2H), 7.29–7.40 (m, 1H), 7.40–7.52 (m, 4H), 7.57–7.66 (m, 2H), 9.30 (s, 1H). LRMS (EI) 491 (M$^+$), 84 ($C_5H_{10}N$, 100%).

EXAMPLE 17

(±)-cis-7-Hydroxy-3-(4-methylphenyl)-4-(4-(2-pyrrolidinoethoxy)phenyl)chromane

In an manner analogous to that described in step 5 for Example 10, (±)-cis-7-methoxy-3-(4-methylphenyl)-4-(4-

(2-pyrrolidinoethoxy)phenyl)chromane (0.444 g, 1.0 mmol) was de-methylated by heating with pyridine hydrochloride to give the title compound as an off-white solid.

Yield 0.305 g (71%) of (±)-cis-7-hydroxy-3-(4-methylphenyl)-4-(4-(2-pyrrolidinoethoxy)phenyl) chromane. M.p. 161–165° C. (ethanol/$CH_2Cl_2$/petrol). $^1$H-NMR ($CDCl_3$, 300 MHz) δ: 1.80–1.95 (bm, 4H), 2.30 (s, 3H), 2.64–2.80 (m, 4H), 2.81–2.92 (m, 1H), 2.97–3.10 (m, 1H), 3.52 (ddd, 1H), 3.96–4.06 (m, 2H), 4.08–4.19 (m, 2H), 4.32 (dd, 1H), 6.34 (dd, 1H), 6.39 (d, 1H), 6.40–6.49 (m, 4H), 6.50–6.56 (m, 2H), 6.75 (d, 1H), 6.92–6.98 (m, 2H), phenol OH not observed. LRMS (EI) 429 (M$^+$), 84 ($C_5H_{10}N$, 100%). Elemental analysis: calculated for $C_{29}H_{33}NO_3$ C, 78.29; H, 7.27; N, 3.26%; found C, 75.06; H, 7.23; N, 3.21%

EXAMPLE 18

(±)-cis-7-Hydroxy-3-(4-methylphenyl)-4-(4-(2-piperidinoethoxy)phenyl)chromane

In an manner analogous to that described in step 5 for Example 10, (±)-cis-7-methoxy-3-(4-methylphenyl)-4-(4-(2-piperidinoethoxy)phenyl)chromane (0.458 g, 1.0 mmol) was de-methylated by heating with pyridine hydrochloride to give the title compound as an off-white solid.

Yield 0.315 g (70%) of (±)-cis-7-hydroxy-3-(4-methylphenyl)-4-(4-(2-piperidinoethoxy)phenyl)chromane. M.p. 146–147.5° C. ($CH_2Cl_2$/petrol). $^1$H-NMR ($CDCl_3$, 300 MHz) δ: 1.45–1.55 (m, 2H), 1.64–1.75 (m, 4H), 2.32 (s, 3H), 2.50–2.70 (m, 4H), 2.70–2.82 (m, 1H), 2.82–2.95 (m, 1H), 3.53 (ddd, 1H), 3.96–4.10 (m, 2H), 4.10–4.20 (m, 2H), 4.33 (dd, 1H), 6.37 (dd, 1H), 6.40 (d, 1H), 6.41–6.50 (m, 4H), 6.50–6.58 (m, 2H), 6.77 (d, 1H), 6.92–7.00 (m, 2H), phenol OH not observed. LRMS (EI) 443 (M$^+$), 98 ($C_6H_{12}N$, 100%). Elemental analysis: calculated for $C_{29}H_{33}NO_3$; C, 78.52; H, 7.50; N, 3.16%; found C, 77.39; H, 7.61; N, 3.06%.

EXAMPLE 19

(±)-cis-7-Hydroxy-4-(4-(2-piperidinoethoxy) phenyl)-3-(4-(trifluoromethyl)phenyl)-chromane In an manner analogous to that described in step 5 for Example 10, (±)-cis-7-methoxy-4-(4-(2-piperidinoethoxy) phenyl)-3-(4-(trifluoromethyl)phenyl)chromane (0.512 g, 1.0 mmol) was de-methylated by heating with pyridine hydrochloride to give the title compound as an off-white solid.

Yield 0.30 g (61%) of (±)-cis-7-hydroxy-4-(4-(2-piperidinoethoxy)phenyl)-3-(4-(trifluoromethyl)phenyl) chromane. M.p. 117–119° C. $^1$H-NMR (DMSO-$d_6$, 300 MHz) δ: 1.30–1.60 (m, 6H), 2.35–2.45 (m, 4H), 2.55–2.65 (m, 2H), 3.60–3.72 (m, 1H), 3.87–4.0 (m, 2H), 4.19–4.42 (m, 3H), 6.25–6.35 (m, 2H), 6.43–6.52 (m, 2H), 6.60–6.70 (m, 3H), 6.95–7.03 (m, 2H), 7.46–7.55 (m, 2H), 9.35 (s, 1H). LRMS (EI) 497 (M$^+$), 98 ($C_6H_{12}N$, 100%). Elemental analysis: calculated for $C_{29}H_{30}F_3NO_3$; C, 70.01; H, 6.08; N, 2.82%; found C, 69.39; H, 6.25; N, 2.64%.

EXAMPLE 20

(±)-cis-7-Hydroxy-4-(4-(2-pyrrolidinoethoxy) phenyl)-3-(4-(trifluoromethyl)phenyl)-chromane In an manner analogous to that described in step 5 for Example 10, (±)-cis-7-methoxy-4-(4-(2-pyrrolidinoethoxy) phenyl)-3-(4-(trifluoromethyl)phenyl)chromane (0.30 g, 0.60 mmol) was de-methylated by heating with pyridine hydrochloride to give the title compound as a colourless powder.

Yield 0.20 g (68%) of (±)-cis-7-hydroxy-4-(4-(2-pyrrolidinoethoxy)phenyl)-3-(4-(trifluoromethyl)phenyl)-chromane. M.p. 100° C. (dec). $^1$H-NMR ($CDCl_3$, 300 MHz) δ: 1.80– 1.95 (m, 4H), 2.65–2.82 (m, 4H), 2.82–2.94 (m, 1H), 3.0–3.12 (m, 1H), 3.62 (ddd, 1H), 3.77–4.08 (m, 2H), 4.16 (dd, 1H), 4.21 (d, 1H), 4.38 (dd, 1H), 6.36 (dd, 1H), 6.41–6.45 (m, 4H), 6.72–6.79 (m, 3H), 7.37–7.44 (m, 2H), phenol OH not observed. LRMS (EI) 483 (M$^+$), 84 ($C_5H_{10}N$, 100%).

EXAMPLE 21

(±)-cis-7-Hydroxy-3-(3-methylphenyl)-4-(4-(2-pyrrolidinoethoxy)phenyl)chromane

In an manner analogous to that described in step 5 for Example 10, (±)-cis-7-methoxy-3-(3-methylphenyl)-4-(4-(2-pyrrolidinoethoxy)phenyl)chromane (0.360 g, 0.75 mmol) was de-methylated by heating with pyridine hydrochloride to give the title compound as an off-white foam.

Yield 0.228 g (70%) of (±)-cis-7-hydroxy-3-(3-methylphenyl)-4-(4-(2-pyrrolidinoethoxy)phenyl) chromane. M.p. 85–90° C. $^1$H-NMR ($CDCl_3$, 300 MHz) δ: 1.85–2.00 (m, 4H), 2.20 (s, 3H), 2.75–2.90 (m, 4H), 2.90–3.03 (m, 1H), 3.03–3.17 (m, 1H), 3.52 (ddd, 1H), 4.00–4.10 (m, 2H), 4.10–4.20 (m, 2H), 4.32 (dd, 1H), 6.32–6.52 (m, 8H), 6.72 (d, 1H), 6.94–7.06 (m, 2H), phenol OH not observed. LRMS (EI) 429 (M$^+$), 84 ($C_5H_{10}N$, 100%). Elemental analysis: calculated for $C_{28}H_{31}NO_3$; C, 78.29; H, 7.27; N, 3.26%; found C, 76.25; H, 7.45; N, 3.00%.

EXAMPLE 22

(±)-cis-3-(3-Fluorophenyl)-7-hydroxy-4-(4-(2-pyrrolidinoethoxy)phenyl)chromane

In an manner analogous to that described in step 5 for Example 10, (±)-cis-3-(3-fluorophenyl)-7-methoxy-4-(4-(2-pyrrolidinoethoxy)phenyl)chromane (0.224 g, 0.50 mmol) was de-methylated by heating with pyridine hydrochloride to give the title compound as an off-white solid.

Yield 0.107 g (49%) of (±)-cis-3-(3-fluorophenyl)-7-hydroxy-4-(4-(2-pyrrolidinoethoxy)phenyl)chromane. M.p. 146–150° C. (ether/petrol). $^1$H-NMR ($CDCl_3$, 300 MHz) δ: 1.85–2.00 (m, 4H), 2.65–2.88 (m, 4H), 2.88–3.14 (m, 2H), 3.50–3.60 (m, 1H), 4.00–4.10 (m, 2H), 4.10–4.23 (m, 2H), 4.32 (dd, 1H), 6.30–6.55 (m, 8H), 6.74 (d, 1H), 6.80–6.90 (m, 1H), 7.05–7.17 (m, 1H), phenol OH not observed. LRMS (EI) 433 (M$^+$), 84 ($C_5H_{10}N$, 100%).

EXAMPLE 23

(±)-cis-7-Hydroxy-3-(3-hydroxyphenyl)-4-(4-(2-pyrrolidinoethoxy)phenyl)chromane

In an manner analogous to that described in step 5 for Example 10, (±)-cis-7-methoxy-3-(3-methoxyphenyl)-4-(4-(2-pyrrolidinoethoxy)phenyl)chromane (0.345 g, 0.75 mmol) was de-methylated by heating with pyridine hydrochloride to give the title compound as an off-white foam.

Yield 0.252 g (77%) of (±)-cis-7-hydroxy-3-(3-hydroxyphenyl)-4-(4-(2-pyrrolidinoethoxy)phenyl) chromane. M.p. 126° C. (dec). $^1$H-NMR (DMSO-$d_6$, 300 MHz) δ: 1.65–1.80 (m, 4H), 2.60–2.80 (m, 4H), 2.85–3.00 (m, 2H), 3.30–3.60 (m, 1H plus water from solvent), 4.00 (t, 2H), 4.12–4.30 (m, 3H), 6.17–6.22 (m, 2H), 6.22–6.34 (m, 2H), 6.44–6.60 (m, 3H), .6.0–6.70 (m, 3H), 6.92 (t, 1H), 9.20 (s, 1H), 9.30 (s, 1H). LRMS (EI) 431 (M$^+$), 84 ($C_5H_{10}N$, 100%)

EXAMPLE 24

(±)-cis-7-Hydroxy-3-(3-hydroxyphenyl)-4-(4-(2-piperidinoethoxy)phenyl)chromane

In an manner analogous to that described in step 5 for Example 10, (±)-cis-7-methoxy-3-(3-methoxyphenyl)-4-(4-

(2-piperidinoethoxy)phenyl)chromane (0.355 g, 0.75 mmol) was de-methylated by heating with pyridine hydrochloride to give the title compound as an off-white foam.

Yield 0.16 (48%) of (±)-cis-7-hydroxy-3-(3-hydroxyphenyl)-4-(4-(2-piperidinoethoxy)phenyl) chromane. M.p. 144° C. (dec). $^1$H-NMR (DMSO-d$_6$, 300 MHz) δ: 1.35–1.65 (bm, 6H), 2.40–3.00 (m, 6H), 3.30–3.50 (m, 1H), 3.95–4.10 (m, 2H) 4.10–4.30 (m, 3H), 6.18–6.22 (m, 2H), 6.22–6.31 (m, 2H), 6.45–6.59 (m, 3H), 6.60–6.7 (m, 3H), 6.92 (t, 1H), 9.18 (s, 1H), 9.30 (s, 1H). LRMS (EI) 445 (M$^+$), 98 (C$_6$H$_{12}$N, 100%).

EXAMPLE 25

(±)-cis-7-Hydroxy-3-(3-hydroxyphenyl)-4-(4-(3-piperidinopropoxy)phenyl)chromane

In an manner analogous to that described in step 5 for Example 10, (±)-cis-7-methoxy-3-(3-methoxyphenyl)-4-(4-(3-piperidinopropoxy)phenyl)chromane (0.49 g, 1.0 mmol) was de-methylated by heating with pyridine hydrochloride to give the title compound as a yellow solid.

Yield 0.28 g (58%) of (±)-cis-7-hydroxy-3-(3-hydroxyphenyl)-4-(4-(3-piperidinopropoxy)phenyl) chromane. $^1$H-NMR (DMSO-d$_6$, 300 MHz) δ: 1.30–1.42 (m, 2H), 1.42–1.54 (m, 4H), 1.80 (pentet, 2H), 2.25–2.44 (m, 6H), 3.40 (ddd, 1H), 3.87 (t, 2H), 4.00–4.32 (m, 3H), 6.15–6.22 (m, 2H), 6.27 (dd, 1H), 6.31 (d, 1H), 6.47 (dm, 2H), 6.57–6.69 (m, 3H), 6.93 (dd, 1H), 9.15 (bs, 1H), 9.28 (s, 1H). LRMS (EI) 459 (M$^+$), 98 (C$_6$H$_{12}$N, 100%).

EXAMPLE 26

(±)-cis-7-Hydroxy-4-(4-(2-pyrrolidinoethoxy) phenyl)-3-(3-(trifluoromethyl)phenyl)chromane In an manner analogous to that described in step 5 for Example 10, (±)-cis-7-methoxy-4-(4-(2-pyrrolidinoethoxy)phenyl)-3-(3-(trifluoromethyl)phenyl)chromane (0.25 g, 0.50 mmol) was de-methylated by heating with pyridine hydrochloride to give the title compound as an off-white solid.

Yield 0.131 g (53%) of (±)-cis-7-hydroxy-4-(4-(2-pyrrolidinoethoxy)phenyl)-3-(3-(trifluoromethyl)phenyl) chromane. M.p. 87–89° C. $^1$H-NMR (CDCl$_3$, 300 MHz) δ: 1.85–2.00 (m, 4H), 2.75–2.90 (m, 4H), 2.90–3.01 (m, 1H), 3.04–3.16 (m, 1H), 3.55–3.66 (m, 1H), 3.77–4.21 (m, 4H), 4.34 (m, 1H), 6.30–6.48 (m, 6H), 6.72 (d, 1H), 6.79 (d, 1H), 6.82 (s, 1H); 7.20–7.30 (m, 1H), 7.40 (d, 1H), phenol OH not observed. LRMS (EI) 483 (M$^+$), 84 (C$_5$H$_{10}$N, 100%). Elemental analysis: calculated for C$_{28}$H$_{28}$F$_3$NO$_3$; C, 69.55; H, 5.84; N, 2.90%; found C, 68.18; H, 5.91; N, 2.78%.

EXAMPLE 27

(±)-cis-7-Hydroxy-4-(4-(2-piperidinoethoxy) phenyl)-3-(3-(trifluoromethyl)phenyl)chromane In an manner analogous to that described in step 5 for Example 10, (±)-cis-7-methoxy-4-(4-(2-piperidinoethoxy) phenyl)-3-(3-(trifluoromethyl)phenyl)chromane (0.256 g, 0.50 mmol) was de-methylated by heating with pyridine hydrochloride to give the title compound as an off-white solid.

Yield 0.19 g (77%) of (±)-cis-7-hydroxy-4-(4-(2-piperidinoethoxy)phenyl)-3-(3-(trifluoromethyl)phenyl)-chromane. M.p. 118–119° C. $^1$H-NMR (CDCl$_3$, 300 MHz) δ: 1.45–1.55 (m, 2H), 1.60–1.80 (m, 4H), 2.50–2.70 (m, 4H), 2.70–2.95 (m, 2H), 3.62 (ddd, 1H), 3.99–4.07 (m, 2H), 4.11–4.22 (m, 2H), 4.37 (dd, 1H), 6.34–6.49 (m, 6H), 6.74–6.83 (m, 2H), 6.85 (s, 1H), 7.22–7.30 (m, 1H), 7.43 (d, 1H), phenol OH not observed. LRMS (EI) 497 (M$^+$), 98 (C$_6$H$_{12}$N, 100%). Elemental analysis: calculated for C$_{29}$H$_{30}$F$_3$NO$_3$; C, 70.01; H, 6.08; N, 2.82%; found C, 68.98; H, 6.18; N, 2.73%.

EXAMPLE 28

(±)-cis-3-(2-Fluorophenyl)-7-hydroxy-4-(4-(2-pyrrolidinoethoxy)phenyl)chromane

In an manner analogous to that described in step 5 for Example 10, (±)-cis-3-(2-fluorophenyl)-7-methoxy-4-(4-(2-pyrrolidinoethoxy)phenyl)chromane (0.20 g, 0.41 mmol) was de-methylated by heating with pyridine hydrochloride to give the title compound as an off-white foam.

Yield 0.104 g (58%) of (±)-cis-3-(2-fluorophenyl)-7-hydroxy-4-(4-(2-pyrrolidinoethoxy)-phenyl)chromane. M.p. 190° C. (dec). $^1$H-NMR (CDCl$_3$ +drop DMSO-d$_6$, 300 MHz) δ: 1.95–2.10 (m, 4H), 3.00–3.18 (m, 4H), 3.18–3.25 (m, 2H), 3.88 (ddd, 1H), 4.14–4.32 (m, 4H), 4.39 (t, 1H), 6.24 (tm, 1H), 6.41 (dd, 1H), 6.48 (d, 1H), 6.50–6.60 (m, 4H), 6.72 (d, 1H), 6.82 (tm, 1H), 6.98–7.07 (m, 1H), 7.11–7.20 (m, 1H), phenol OH not observed. LRMS (EI) 433 (M$^+$), 84 (C$_5$H$_{10}$N, 100%).

EXAMPLE 29

(±)-cis-7-Hydroxy-3-(2,3,4,5,6-pentafluorophenyl)-4-(4-(2-pyrrolidinoethoxy)phenyl)-chromane In an manner analogous to that described in step 5 for Example 10, (±)-cis-7-methoxy-3-(2,3,4,5,6-pentafluorophenyl)-4-(4-(2-pyrrolidinoethoxy)phenyl) chromane (0.260 g, 0.50 mmol) was de-methylated by heating with pyridine hydrochloride to give the title compound as an off-white foam.

Yield 0.198 g (78%) of (±)-cis-7-hydroxy-3-(2,3,4,5,6-pentafluorophenyl)-4-(4-(2-pyrrolidinoethoxy)phenyl) chromane. M.p. 125° C. (dec). $^1$H-NMR (CDCl$_3$, 300 MHz) δ: 1.90–2.05 (m, 4H), 2.90–3.05 (m, 4H), 3.05–3.25 (m, 2H), 3.90–4.02 (m, 1H) 4.10–4.30 (m, 4H), 4.51–4.65 (m, 1H), 6.35–6.45 (m, 2H), 6.50–6.63 (m, 4H), 6.69 (d, 1H), phenol OH not observed. LRMS (EI) 505 (M$^+$), 84 (C$_5$H$_{10}$N+, 100%).

EXAMPLE 30

(±)-cis-7-Hydroxy-3-(2,3,4,5,6-pentafluorophenyl)-4-(4-(2-piperidinoethoxy)phenyl)-chromane In an manner analogous to that described in step 5 for Example 10, (±)-cis-7-methoxy-3-(2,3,4,5,6-pentafluorophenyl)-4-(4-(2-piperidinoethoxy)phenyl) chromane (0.428 g, 0.75 mmol) was de-methylated by heating with pyridine hydrochloride to give the title compound as an off-white foam.

Yield 0.317 g (81%) of (±)-cis-7-hydroxy-3-(2,3,4,5,6-pentafluorophenyl)-4-(4-(2-piperidinoethoxy)phenyl) chromane. M.p. 174° C. (dec). $^1$H-NMR (CDCl$_3$, 300 MHz) δ: 1.45–1.60 (m, 2H), 1.65–1.90 (m, 4H), 2.65–2.85 (m, 4H), 2.85–3.05 (m, 2H) 3.80–4.05 (m, rotamers, 1H), 4.05–4.35 (m, 4H), 4.52–4.68 (m, 1H), 6.35–6.50 (m, 2H), 6.50–6.70 (m, 4H), phenol OH not observed. LRMS (EI) 519 (M$^+$), 98 (C$_6$H$_{12}$N, 100%).

EXAMPLE 31

(±)-cis-6-Hydroxy-3-phenyl-4-(4-(2-pyrrolidinoethoxy)phenyl)-chromane

Step 1
(4-Benzyloxyphenyl)-(2, 5-dimethoxyphenyl)-methanone

Butyllithium (2.0M in hexanes, 6.6 ml, 13.2 mmol) was added dropwise under nitrogen, at −78° C. to a stirred tetrahydrofuran (20 ml) solution of 4-benzyloxy-bromobenzene (3.15 g, 11.97 mmol) to give a yellow coloured suspension, which was stirred for 10 minutes. A tetrahydrofuran (10 ml) solution of N,N-dimethyl 2,5-dimethoxybenzamide (2.09 g, 9.99 mmol) was then added slowly, and the resulting mixture warmed to room temperature over 20 h. The mixture was diluted with 50ml of 1M hydrochloric acid and the product extracted into dichloromethane (4×50 ml). The combined extracts were washed with brine, dried over sodium sulfate and evaporated to a yellow coloured solid. This crude product was purified by column chromatography on silica gel 60, using 4:1 petrol/ethyl acetate as the eluent. This gave the product as a colourless solid, which was recrystallised from hot ethanol (25 ml) to give the product as colourless platelets which were vacuum dried.

Yield 1.61 g (46%) of (4-benzyloxyphenyl)-(2,5-dimethoxyphenyl)-methanone. M.p. 111–113° C. (ethanol). $^1$H-NMR (CDCl$_3$, 300 MHz) δ: 3.70 (s, 3H), 3.78 (s, 3H), 5.13 (s, 2H), 6.85–7.02 (m, 5H), 7.30–7.47 (m, 5H), 7.82 (dm, 2H). LRMS (EI) 348 (M$^+$), 257, 91.

Step 2
(2-Hydroxy-5-methoxyphenyl)-(4-hydroxyphenyl)-methanone

Palladium on carbon catalyst (10%, 1.0 g, 0.94 mmol) was added to a stirred ethanol (500 ml) solution of (4-benzyloxyphenyl)-(2,5-dimethoxyphenyl)-methanone (10.86 g, 31.2 mmol) and the suspension hydrogenated for 18 h. The catalyst was removed by filtration, and the solvent evaporated to give an orange coloured gum. This was dissolved in glacial acetic acid (16 ml), hydrogen bromide (33% w/w in acetic acid, 8.20 ml, 46.76 mmol) added, and the resulting mixture heated to 70° C. for 18 h. The mixture was diluted with water (25ml) and the product extracted into ethyl acetate (3×25 ml). The combined extracts were washed with brine, dried over magnesium sulfate and evaporated to a yellow gum, which was purified by column chromatography on silica gel 60, with 7:3 petrol/ethyl acetate as eluent. This gave a yellow gum, which was dissolved in a minimum of ether and precipitated by adding petrol, to give the title product as a yellow powder.

Yield 0.59 g (8%) of (2-hydroxy-5-methoxyphenyl)-(4-hydroxyphenyl)-methanone M.p. 144.5–147.5° C. (ethyl acetate/petrol). $^1$H-NMR (CDCl$_3$, 300 MHz) δ: 3.74 (s, 3H), 6.30 (bs, 1H), 6.92 (dm, 2H), 7.01 (d, 1H), 7.10 (d, 1H), 7.13 (dd, 1H), 7.68 (dm, 2H), 11.50 (s, 1H). LRMS (EI) 244 (M$^+$), 150 (M-PhOH).

Step 3
4-(4-Acetoxyphenyl)-3-phenyl-6-methoxy-coumarin

A mixture of (2-hydroxy-5-methoxyphenyl)-(4-hydroxyphenyl)-methanone (0.59 g, 2.42 mmol), acetic anhydride (1.15 ml, 12.1 mmol), triethylamine (0.44 ml, 3.16 mmol), and phenyl acetic acid (0.33 g, 2.42 mmol) was stirred at 135° C. for 18 h. The resulting orange coloured solution was poured into water (20 ml) and stirred for 3 h, and the resulting mixture of aqueous solution plus sticky solid was diluted with ethyl acetate (20 ml) to dissolve the solid, and the organic layer separated. The aqueous phase was further extracted with ethyl acetate (2×20 ml). The combined organic extracts were washed with water, then brine, dried over sodium sulfate and evaporated to give a yellow/orange gum. This gum was dissolved in a minimum of ether and petrol added to precipitate the title compound as an off white powder.

Yield 0.49 g (52%) of 4-(4-acetoxyphenyl)-3-phenyl-6-methoxy-coumarin. $^1$H-NMR (CDCl$_3$, 300 MHz) δ: 2.28 (s, 3H), 3.72 (s, 3H), 6.70 (d, 1H), 7.04–7.25 (m, 10H), 7.48 (d, 1H). LRMS (EI) 386 (M$^+$), 344, 327, 316, 43.

Step 4
(±)-cis-6-Methoxy-3-phenyl-4-(4-(2-pyrrolidinoethoxy)phenyl)chromane

Lithium aluminium hydride (0.96 g, 2.54 mmol) was added in small portions to a stirred solution of 4-(4-acetoxyphenyl)-3-phenyl-6-methoxy-coumarin (0.49 g, 1.27 mmol) in tetrahydrofuran (75 ml). The resulting mixture was stirred for 30 min., 6M hydrochloric acid (4 ml) added dropwise, and the mixture heated to 65° C. for 3 h. The mixture was cooled to room temperature, diluted with 100 ml water, and the product extracted into ethyl acetate (2×100 ml). The extracts were washed with brine, dried over sodium sulfate and evaporated to give a yellow gum. This gum was dissolved in ethanol (100 ml), and palladium on carbon (5%, 0.045 g, 0.02 mmol) added, then the mixture was hydrogenated for 18 h. The catalyst was removed by filtration and the solvents evaporated to give an orange gum, which was vacuum dried. The gum was dissolved in dry acetone (20 ml) then potassium carbonate (1.87 g, 13.50 mmol), 1-(2-chloroethyl)pyrrolidine hydrochloride (0.257 g, 1.51 mmol) and sodium iodide (0.01 g, catalyst) were added and the mixture heated to 60° C. for 20 h. The inorganic solids were removed by filtration and the solvent removed to give an orange gum, which was purified by column chromatography on silica gel 60 with 9:1 dichloromethane/methanol eluent. This gave the product as a pale orange gum, which was vacuum dried.

Yield 0.34 g (62%) of (±)-cis-6-methoxy-3-phenyl-4-(4-(2-pyrrolidinoethoxy)phenyl)-chromane. $^1$H-NMR (CDCl$_3$, 300 MHz) δ: 1.70–1.90 (m, 4H), 2.55–2.70 (m, 4H), 2.85 (t, 2H), 3.56 (ddd, 1H), 3.69 (s, 3H), 4.02 (t, 2H), 4.15–4.28 (m, 2H), 4.40 (dd, 1H), 6.45–6.55 (m, 3H), 6.55–6.72 (m, 4H), 6.79 (dd, 1H), 6.90 (d, 1H), 7.10–7.20 (m, 3H).

Step 5
(±)-cis-6-Hydroxy-3-phenyl-4-(4-(2-pyrrolidinoethoxy)phenyl)chromane

A mixture of (±)-cis-6-methoxy-3-phenyl-4-(2-pyrrolidinoethoxy)phenyl)chromane (0.34 g, 0.79 mmol) and pyridine hydrochloride (0.91 g, 7.9 mmol) was stirred at 135° C. for 18 h, cooled to room temperature and the resulting dark solid dissolved in a mixture of methanol (10 ml), water (50 ml) and dichloromethane (50 ml). The aqueous layer was separated and further extracted with 4:1 dichloromethane /methanol (50 ml). The organic layers were combined, washed with brine, dried over magnesium sulfate, and evaporated. The product was purified by column chromatography on silica gel 60, with 5% methanol in di-chloromethane as eluent. The resulting gum was dissolved in approximately 1 ml ethanol and then diethylether added. This resulted in the precipitation of the title compound as a partial hydrochloride salt. The solid was dissolved in dichloromethane, washed with sodium hydrogen carbonate solution, brine, dried over magnesium sulfate and evaporated to give the title compound as a pale yellow foam.

Yield 70 mg (21%) of (±)-cis-6-hydroxy-3-phenyl-4-(4-(2-pyrrolidinoethoxy)phenyl)-chromane. $^1$H-NMR (CDCl$_3$, 200 MHz) δ: 1.70–1.90 (m, 4H), 2.55–2.75 (m, 4H), 2.85 (t, 2H), 3.55 (ddd, 1H), 3.90–4.10 (m, 2H), 4.15–4.28 (m, 2H), 4.40 (dd, 1H), 6.38 (d, 1H), 6.42–6.60 (m, 4H), 6.60–6.75 (m, 3H), 6.85 (d, 1H), 7.05–7.25 (m, 3H), phenol OH not observed.

EXAMPLE 32

(±)-cis-6-Hydroxy-3-(3-hydroxyphenyl)-4-(4-(2-pyrrolidinoethoxy)phenyl)chromane

The title compound was prepared in a manner exactly analogous to that described for Example 32, with the substitution of 3-methoxyphenyl acetic acid in the place of phenyl acetic acid in Step 3.

Thus, (±)-cis-6-methoxy-3-(3-methoxyphenyl)-4-(4-(2-pyrrolidinoethoxy)phenyl)-chromane (0.24 g, 0.52 mmol) was de-methylated by heating with pyridine hydrochloride (0.60 g, 5.20 mmol) to give the title compound, after purification and drying, as a colourless gum.

Yield 95 mg (35%) of (±)-cis-6-hydroxy-3-(3-hydroxyphenyl)-4-(4-(2-pyrrolidinoethoxy)phenyl) chromane. $^1$H-NMR (MeOH-$d_4$, 200 MHz) δ: 1.90–2.10 (m, 4H), 3.05–3.25 (m, 4H), 3.25–3.55 (m, 3H), 4.10–4.42 (m, 5H), 6.15 (m, 1H), 6.26 (dm, 1H), 6.30 (d, 1H), 6.50–6.80 (m, 7H), 6.92 (dd, 1H), phenol OH signals not observed.

EXAMPLE 33

(±)-cis-4-(4-Hexylphenyl)-7-hydroxy-3-phenylchromane

Step 1

(±)-(cis-4-((7-methoxy-3-phenyl)chroman-4-yl)phenyl trifluoromethanesulfonic acid ester A stirred suspension of (±)-cis-4-(4-hydroxyphenyl)-7-methoxy-3-phenylchromane (5.0 g, 15 mmol) in a mixture of dichloromethane (50 ml) and triethylamine (2.9 ml, 21 mmol) was treated dropwise at 0° C., under a nitrogen atmosphere, with trifluoromethanesulfonic anhydride (5.0 g, 17 mmol), and the mixture warmed slowly to room temperature. The resulting rather viscous solution was diluted with tetrahydrofuran (100 ml), and stirred for a further 24 hours. The reaction mixture was filtered, the solvents evaporated, and the residue partitioned between dichloromethane (200 ml) and 10% aqueous acetic acid (200 ml). The organic layer was separated, washed with 10% aqueous acetic acid (100 ml), sodium hydrogen carbonate solution (3×100 ml), brine (100 ml), dried over sodium sulfate, and evaporated. The product was purified by column chromatography on silica gel 60, with dichloromethane as the eluent. This gave the product as a clear gum, which was crystallised from diethylether and petrol, to afford the title product as colourless crystals.

Yield 2.88 g (41%) of (±)-(cis-4-((7-methoxy-3-phenyl) chroman4-yl)phenyl trifluoromethanesulfonic acid ester. M.p. 98–99° C. $^1$H-NMR (CDCl$_3$, 300 MHz) δ: 3.65 (m, 1H), 3.81 (s, 3H), 4.24–4.40 (m, 3H), 6.49 (dd, 1H), 6.53 (d, 1H), 6.61–6.69 (m, 4H), 6.82 (d, 1H), 6.96 (d, 2H), 7.11–7.20 (m, 3H). LRMS(EI): 464 (M$^+$).

Step 2

(±)-cis-4-(4-Hexylphenyl)-7-methoxy-3-phenylchromane

An oven dried 2-necked flask fitted with a reflux condenser and an inlet septum, was charged, under a nitrogen atmosphere, with 9-borabicylo[3.3.1]nonane) (0.5M in tetrahydrofuran solution, 4.74 ml, 2.37 mmol), which was cooled to 0° C. 1-Hexene (199 mg, 2.37 mmol) was added, and the mixture slowly warmed to room temperature over 7 hours. Anhydrous dioxane (20 ml), caesium carbonate (1.05 g, 3.23 mmol), tetrakis(triphenylphosphine)palladium (0) (62 mg, 0.05 mmol) and (±)-(cis-4-((7-methoxy-3-phenyl) chroman-4-yl)phenyl trifluoromethanesulfonic acid ester (1.0 g, 2.15 mmol) were added, and the mixture heated to gentle reflux for 24 h. The mixture was cooled to room temperature and diluted with hexane (20 ml), then 2M sodium hydroxide (1.6 ml) and 30% hydrogen peroxide (1 ml) were added, and the mixture stirred for 2 hours to destroy the excess borane. The resulting mixture was diluted with ethyl acetate (200 ml) and water (200 ml), and the organic layer separated, washed with water (100 ml), brine (100 ml), dried over sodium sulfate, and evaporated. The crude product was purified by column chromatography on silica gel 60, with 2% methanol in dichloromethane as the eluent. This gave the title compound as a clear oil.

Yield 0.758 g (88%) of (±)-cis-4-(4-hexylphenyl)-7-methoxy-3-phenylchromane. $^1$H-NMR (CDCl$_3$, 300 MHz) δ: 0.88 (t, 3H), 1.20–1.32 (m, 6H), 1.53 (m, 2H), 2.50 (t, 2H), 3.59 (m, 1H), 3.80 (s, 3H), 4.20–4.29 (m, 2H), 4.45 (t, 1H), 6.42–6.53 (m, 4H), 6.61–6.68 (m, 2H), 6.82–6.89 (m, 3H), 7.08–7.19 (m, 3H). LRMS (EI): 400 (M$^+$).

Step 3

(±)-cis-4-(4-Hexylphenyl)-7-hydroxy-3-phenylchromane

A mixture of (±)-cis-4-(4-hexylphenyl)-7-methoxy-3-phenylchromane (0.46 g, 1.15 mmol) and anhydrous pyridine hydrochloride (6.60 g, 57.4 mmol) was heated to 150–155° C. as a melt for 18 hours. The mixture was cooled to room temperature, and the resulting orange coloured wax dissolved in a mixture of water (100 ml), hot ethanol (10 ml) and dichloromethane (100 ml). The organic layer was separated and the aqueous layer further extracted with dichloromethane (3×50 ml). The combined organic layers were washed with saturated sodium chloride, dried over sodium sulfate and evaporated to a dark coloured oil, which was purified by column chromatography on silica gel 60, with 2% methanol in dichloromethane as eluent; giving the title compound as a red oil.

Yield 158 mg (35%) of (±)-cis-4-(4-Hexylphenyl)-7-hydroxy-3-phenylchromane. $^1$H-NMR (CDCl$_3$, 300 MHz) δ: 0.87 (t, 3H), 1.20–1.32 (m, 6H), 1.51 (m, 2H), 2.49 (t, 2H), 3.57 (m,1H), 4.18–4.25 (m, 2H), 4.43(t, 1H), 4.78 (s, 1H), 6.36 (dd, 1H), 6.46 (d, 1H), 6.49 (d, 2H), 6.62 (dd, 2H), 6.79–6.88 (m, 3H), 7.08–7.20 (m, 3H). Elemental analysis: calculated for $C_{27}H_{30}O_2$: C, 83.91; H, 7.82%; Found: C, 83.45; H, 7.78%. LRMS (EI): 386 (M$^+$).

EXAMPLE 34

(+, −) cis [4-(7-Hydroxy-3-phenyl-chroman-4-yl)-phenoxy]-acetic acid

Step 1

(+−) cis [4-(7-Benzyloxy-3-phenyl-chroman-4-yl)-phenoxy]-acetic acid methyl ester (+,−) cis 4-(7-Benzyloxy-3-phenyl-chroman-4-yl)-phenol (0.5 g, 1.22 mmol), methyl bromoacetate (0.37 g, 2.44 mmol), 18-crown-6 (0.48 g, 1.83 mmol), and potassium carbonate 0.25 g, 1.83 mmol) was slurried in toluene (25 ml), and stirred at 100° C. for 75 min. After cooling the reaction mixture was filtered through a 1.6×6 cm silica column, eluted with 10% tetrahydrofuran in toluene and evaporated.

Yield 550 mg (94%) of (+,−) cis [4-(7-Benzyloxy-3-phenyl-chroman-4-yl)-phenoxy]-acetic acid methyl ester; m.p. 143.3–144.1° C.

The product was identified by $^1$H-NMR.

Step 2

(+,−) cis [4-(7-Hydroxy-3-phenyl-chroman-4-yl)-phenoxy]-acetic acid methyl ester (+,−) cis [4-(7-Benzyloxy-3-phenyl-chroman-4-yl)-phenoxy]-acetic acid methyl ester(100 mg, 0.21 mmol) was dissolved in a solvent mixture of tetrahydrofuran-methanol-formic acid (8+1+1, 10 ml). The solution was added to a 5% Palladium on carbon catalyst (20 mg), and hydrogenated (1 atm.) overnight. The reaction mixture was filtered and evaporated to give a dark oil, which was dissolved and evaporated from EtOH (×3), triturated with toluene, and recrystallised from toluene.

Yield 60 mg (73%) of (+,−) cis [4-(7-Hydroxy-3-phenyl-chroman-4-yl)-phenoxy]-acetic acid methyl ester; m.p. 132.8–134° C.

The product was identified by $^1$H-NMR.

Step 3

(+,−) cis [4-(7-Hydroxy-3-phenyl-chroman-4-yl)-phenoxy]-acetic acid (+,−) cis [4-(7-Hydroxy-3-phenyl-chroman-4-yl)-phenoxy]-acetic acid methyl ester (30 mg, 0.077 mmol) was stirred in 2N potassium hydroxide in methanol (1 ml) for 120 min. The reaction mixture was acidified by 1 N hydrochloric acid (2.5 ml), and stirring continued for 60 min. The precipitated product was filtered, washed with water and vacuum dried with sicapent (Merck) at 50° C. overnight.

Yield 20 mg (69%) of (+,−) cis [4-(7-Hydroxy-3-phenyl-chroman-4-yl)-phenoxy]-acetic acid;
m.p. 177.5–178.5° C.° C.

The product was identified by $^1$H-NMR.

EXAMPLE 35

This example was performed essentially as described in example 35.

(+,−) cis 4-[4-(7-Hydroxy-3-phenyl-chroman-4-yl)-phenoxy]-butyric acid

Step 1

(+,−) cis 4-[4-(7-Benzyloxy-3-phenyl-chroman-4-yl)-phenoxy]-but-2-enoic acid ethyl ester From (+,−) cis 4-(7-Benzyloxy-3-phenyl-chroman-4-yl)-phenol (0.5 g, 1.22 mmol), and 4-Bromo-but-2-enoic acid ethyl ester (0.63 g, 2.44 mmol).

Yield 0.45 g (71%) of (+−) cis 4-[4-(7-Benzyloxy-3-phenyl-chroman-4-yl)-phenoxy]-but-2-enoic acid ethyl ester, m.p.74.4–75.1 (EtOH)

The product was identified by $^1$H-NMR.

Step 2

(+,−) cis 4-[4-(7-Hydroxy-3-phenyl-chroman-4-yl)-phenoxy]-butyric acid ethyl ester From (+,−) cis 4-[4-(7-Benzyloxy-3-phenyl-chroman-4-yl)-phenoxy]-but-2-enoic acid ethyl ester (0.3 g, 0.58 mmol) in tetrahydrofuran (25 ml). Purified further on a silica column using tetrahydrofuran-toluen (1+9) as eluent.

Yield 0.21 g (84%) of (+,−) cis 4-[4-(7-Hydroxy-3-phenyl-chroman-4-yl)-phenoxy]-butyric acid ethyl ester, oil.). $^1$H-NMR (CDCl$_3$, 300 MHz) δ: 1.26 (t, 3H); 2.06 (m, 2H); 2.48 (t, 2H); 3.55 (m, 1H); 3.90 (t, 2H), 4.17 (m, 4H); 4.40 (t, 1H); 6.18 (br, 1H); 6.37 (dd, 1H), 6.48 (m, 3H); 6.57 (d, 2H); 6.66 (m, 2H); 6.78 (d, 1H); 7.12 (m, 3H)

Step 3

(+,−) cis 4-[4-(7-Hydroxy-3-phenyl-chroman-4-yl)-phenoxy]-butyric acid

From (+,−) cis 4-[4-(7-Hydroxy-3-phenyl-chroman-4-yl)-phenoxy]-butyric acid ethyl ester (100 mg, 0.46 mmol).

Yield 57 mg of (+,−) cis 4-[4-(7-Hydroxy-3-phenyl-chroman-4-yl)-phenoxy]-butyric acid, m.p.91.5–94° C.

The product was identified by $^1$H-NMR.

EXAMPLE 36

(+,−) cis 7-hydroxy-4-[4-(6-morpholinohexyloxy)-phenyl]-3-phenyl-chroman

Step 1

(+,−) cis 7-Benzyloxy-4-[4-(6-morpholinohexyloxy)-phenyl]-3-phenyl-chroman

7-Benzyloxy-4-[4-(6-bromohexyloxy)-phenyl]-3-phenyl-chroman (300 mg, 0.53 mmol), morpholine (229 mg, 2.63 mmol), potassium carbonate (145 mg, 1.05 mmol), and potassium iodide (17 mg, 0.11 mmol) was refluxed in toluene (5 ml) for 3 days. The reaction mixture was cooled, filtered, and the precipitate washed with toluene. The combined filtrate and washings were evaporated, triturated with ethanol, and recrystallised from ethanol.

Yield 229 mg (75%) of (+,−) cis 7-Benzyloxy-4-[4-(6-morpholinohexyloxy)-phenyl]-3-phenyl-chroman, m.p. 85.7–87.5° C.

The product was identified by $^1$H-NMR.

Step 2

(+,−) cis 7-hydroxy-4-[4-(6-morpholinohexyloxy)-phenyl]-3-phenyl-chroman (+,−) cis 7-Benzyloxy-4-[4-(6-morpholinohexyloxy)-phenyl]-3-phenyl-chroman (150 mg, 0.26 mmol) was dissolved in a solution of 1% Hydrochloride in ethanol (5 ml). The solution was added to a 10% palladium on carbon catalyst, and hydrogenated (1 atm.) overnight. The reaction mixture was filtered and evaporated to give an oil which solidified.

Yield 117 mg (86%) of (+,−) cis 7-hydroxy-4-[4-(6-morpholinohexyloxy)-phenyl]-3-phenyl-chroman.HCl m.p. 97–99° C.

The product was identified by $^1$H-NMR.

EXAMPLE 37

(+,−) cis 7-Hydroxy-4-[4-(morpholinodecyloxy)-phenyl]-3-phenylchroman

Step 1

(+,−) cis 7-Benzyloxy-4-[4-(morpholinodecyloxy)-phenyl]-3-phenylchroman

From (+,−) cis 7-Benzyloxy-4-[4-(bromodecyloxy)-phenyl]-3-phenylchroman (300 mg, 0.48 mmol) and morpholine (208 mg, 2.4 mmol).

Yield 122 mg (40%) of (+,−) cis 7-Benzyloxy-4-[-(morpholinodecyloxy)-phenyl]-3-phenylchroman. Oil. $^1$H-NMR (CDCl$_3$, 200 MHz) δ: 1.3 (m, 14H); 1.7 (m, 2H); 2.31 (t, 2H); 2.40 (m, 4H); 3.55 (m, 1H); 3.70 (m, 4H); 3.85 (t, 2H); 4.22 (m, 2H); 4.43 (t, 1H); 5.05 (s, 2H); 6.68 (m, 8H); 6.85 (d, 1H); 7.15 (m, 3H); 7.38 (m, 5H).

Step 2

(+,−) cis 7-Hydroxy-4-[4-(morpholinodecyloxy)-phenyl]-3-phenylchroman

From (+,−) cis 7-Benzyloxy-4-[4-(morpholinodecyloxy)-phenyl]-3-phenylchroman (122 mg, 0.19 mmol). The evaporated product was reevaporated from acetone (×3) to give a solid.

Yield 64 mg (61%) of (+,−) cis 7-Hydroxy-4-[4-(morpholinodecyloxy)-phenyl]-3-phenylchroman.HCl. $^1$H-NMR (CDCl$_3$, 200 MHz) δ: 1.35 (m, 14H); 1.7 (m, 2H); 2.85 (m, 4H); 3.1 (m, 2H); 3.55 (m, 1H); 3.82 (m, 4H); 3.85 (t, 2H); 4.22 (m, 2H); 4.43 (t, 1H); 5.05 (s, 2H); 6.3 (m, 2H); 6.65 (m, 7H); 7.1 (m, 3H).

EXAMPLE 38

(+,−) cis 7-Hydroxy 4-[4-(morpholinoethyloxy)-phenyl]-3-phenyl-chroman

Step 1

(+,−) cis 7-Benzyloxy 4-[4-(morpholinoethyloxy)-phenyl]-3-phenyl-chroman (+,−) cis 7-Benzyloxy-4-[4-(2-chloroethyloxy)-phenyl]-3-phenyl-chroman (263 mg, 0.56 mmol), morpholine (243 mg, 2.79 mmol), potassium carbonate (155 mg, 1.12 mmol), and potassium iodide (18 mg, 0.11 mmol) in dimethylformamide (5 ml) was stirred at 60° C. for 4 days. The reaction mixture was cooled and ether and water was added. The aqueous phase was extracted with ether, and the combined organic phases were washed with water and brine, dried (magnesium sulphate), and evaporated. The evaporated product was precipitated from ethanol.

Yield 139 mg (48%) of (+,−) cis 7-Benzyloxy 4-[4-(morpholinoethyloxy)-phenyl]-3-phenyl-chroman, $^1$H-NMR (CDCl$_3$, 200 MHz) δ: 2.52 (t, 4H); 2.75 (t, 2H); 3.58 (m, 1H); 3.70 (t, 4H); 4.0 (t, 2H); 4.2 (m, 2H); 4.4 (t, 1H); 5.05 (s, 2H); 6.6 m (m, 8H); 6.83 (d, 1H); 7.13 (m, 3H); 7.38 (M, 5H).

Step 2

(+,−) cis 7-Hydroxy-4-[4-(morpholinoethyloxy)-phenyl]-3-phenyl-chroman (+,−) cis 7-Benzyloxy-4-[4-(morpholinoethyloxy)-phenyl]-3-phenyl-chroman (139 mg, 0.27 mmol) was dissolved in a solution of 1% hydrochloride in ethanol (5 ml). The solution was added to a 10% palladium on carbon catalyst, and hydrogenated (1 atm.) overnight. The reaction mixture was filtered and evaporated. The evaporated product was dissolved in acetone and evaporated to give a glassy solid.

Yield 20 mg (17%) of (+,−) cis 7-Hydroxy 4-[4-(morpholinoethyloxy)-phenyl]-3-phenyl-chroman. $^1$H-NMR (MeOH, 200 MHz) δ: 2.52 (t, 4H); 2.82 (t, 2H); 3.49 (m, 1H); 3.70 (t, 4H); 4.0 (t, 2H); 4.18 (m, 2H); 4.38 (t, 1H); 5.1 (s, 2H); 6.3 (m, 1H); 6.38 (m, 1H); 6.47 (d, 2H); 6.56 (d, 2H); 6.86 (m, 3H); 7.10 (m, 3H).

The following example was performed essentially as described above.

EXAMPLE 39

(+,−) cis 7-Hydroxy 4-[4-(N-methylpiperazinoethyloxy)-phenyl]-3-phenyl-chroman

Step 1

(+,−) cis 7-Benzyloxy 4-[4-(N-methylpiperazinoethyloxy)-phenyl]-3-phenyl-chroman From (+,−) cis 7-Benzyloxy-4-[4-(2-chloroethyloxy)-phenyl]-3-phenyl-chroman (235 mg, 0.50 mmol) and N-methylpiperazine (250 mg, 2.5 mmol). Reaction time 3 days. The reaction mixture was filtered, and water and ether was added. The aqueous phase was extracted with ether. The combined organic extracts was washed with water, and extracted with 0.01 N hydrochloric acid. (×5). The combined acidic extracts were basified to pH 10 and extracted with ether (×3), dried, and evaporated. The product was precipitated from ether-petrol ether.

Yield 122 mg (46%) of (+,−) cis 7-Benzyloxy 4-[4-(N-methylpiperazinoethyloxy)-phenyl]-3-phenyl-chroman, m.p. 103.2–106.8° C.

The product was identified by $^1$H-NMR.

Step 2

(+,−) cis 7-Hydroxy 4-[4-(N-methylpiperazinoethyloxy)-phenyl]-3-phenyl-chroman

From (+,−) cis 7-Benzyloxy 4-[4-(N-methylpiperazinoethyloxy)-phenyl]-3-phenyl-chroman (100 mg, 0.19 mmol). The evaporated product was evaporated from acetone (×3) to give a yellow solid.

Yield 60 mg (67%) of (+,−) cis 7-Hydroxy 4-[4-(N-methylpiperazinoethyloxy)-phenyl]-3-phenyl-chroman.HCl. $^1$H-NMR (MeOH, 200 MHz) δ: 3.0 (s, 3H); 3.65 (m, 11H); 4.28 (m, 5H); 6.3 (m, 2H); 6.65 (m, 7H); 7.1 (m, 3H).

EXAMPLE 40

(+,−) cis 7-Hydroxy 4-[4-(morpholinobutyloxy)-phenyl]-3-phenyl-chroman

Step 1

(+,−) cis 7-Benzyloxy 4-[4-(morpholinobutyloxy)-phenyl]-3-phenyl-chroman

From (+,−) cis 7-Benzyloxy-4-[4-(4-chlorobutyloxy)-phenyl]-3-phenyl-chroman (300 mg, 0.60 mmol) and morpholine (240 mg, 3 mmol). Reaction time 4 days. The evaporated product was crystallised from ether-petrolether, and further purified by silica column chromatography using methanol-methylene chloride (1+19) as eluent.

Yield 160 mg (47%) of (+,−) cis 7-Benzyloxy 4-[4-(morpholinobutyloxy)-phenyl]-3-phenyl-chroman. Oil. $^1$H-NMR (CDCl$_3$, 200 MHz) δ: 1.68 (m,4H); 2.38 (m, 6H); 3.55 (m, 1H); 3.70 (t, 4H); 3.88 (t, 2H); 4.2 (m, 2H); 4.40 (t, 1H); 5.03 (s, 2H); 6.56 (m, 8H); 6.83 (d, 1H); 7.15 (m, 3H); 7.38 (m, 5H).

Step 2

(+,−) cis 7-Hydroxy-4-[4-(morpholinobutyloxy)-phenyl]-3-phenyl-chroman

From (+,−) cis 7-Benzyloxy-4-[4-(morpholinobutyloxy)-phenyl]-3-phenyl-chroman (160 mg, 0.29 mmol) The evaporated product crystallised.

Yield 130 mg (92%) of (+,−) c.s 7-Hydroxy-4-[4-(morpholinobutyloxy)-phenyl]-3-phenyl-chroman. HCl m.p. 79.8–81.8° C.

The product was identified by $^1$H-NMR.

What is claimed is:

1. A compound of the formula I in which substituents $R^2$ and $R^3$ are arranged in cis-configuration:

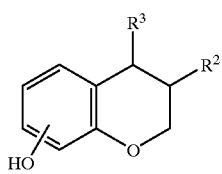

(I)

wherein:

$R^2$ is phenyl optionally substituted with 1 to 5 substituents independently selected from the group consisting of OH, halogen, nitro, cyano, SH, $SR^4$, trihalo-$C_1$–$C_6$-alkyl, $C_1$–$C_6$-alkyl, $C_1$–$C_6$-alkoxy and phenyl;

$R^3$ is:

(a) phenyl substituted with —X—$(CH_2)_n$—Y, wherein:
X is a valency bond, O or S,
n is an integer in the range of 1 to 12,
Y is H, halogen, OH, $OR^4$, $NHCOR^4$, $NHSO_2R^4$, $CONHR^4$, $CONR_2^4$, COOH, $COOR^4$, $SO_2R^4$, $SOR^4$, $SONHR^4$, $SONR_2$, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy; or (b) —$(CH_2)_n$—V, wherein n is as defined above and V is H, OH, $OR^4$, $NHR^4$, $NR_2^4$, $NHCOR^4$, $NHSC_2R^4$, $CONHR^4$, $CONR_2^4$, COOH, $COOR^4$, $SO_2R^4$, $SOR^4$, $SONHR^4$, $SONR_2^4$, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy; or (c) phenyl fused to a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy; and $R^4$ is $C_1$–$C_6$-alkyl;

and optical and geometrical isomers, and pharmaceutically acceptable salts thereof.

2. A compound of the formula I in which substituents $R^2$ and $R^3$ are arranged in cis-configuration:

(I)

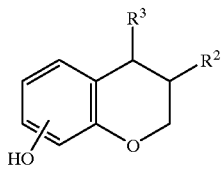

wherein:

R² is phenyl optionally substituted with 1 to 3 substituents independently selected from the group consisting of OH, halogen, nitro, cyano, SH, SR⁴, trihalo-$C_1$–$C_6$-alkyl, $C_1$–$C_6$-alkyl and $C_1$–$C_6$-alkoxy;

R³ is:
(a) phenyl substituted with —X—(CH$_2$)$_n$—Y, wherein:
X is a valency bond, O or S,
n is an integer in the range of 1 to 12,
Y is H, OH, OR⁴, NHCOR⁴, NHSO$_2$R⁴, CONHR⁴, CONR$_2$⁴, COOH, COOR⁴, SO$_2$R⁴, SOR⁴, SONHR⁴, SONR$_2$⁴, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, SR⁴, trihalo-$C_1$–$C_6$-alkyl, $C_1$–$C_6$-alkyl and $C_1$–$C_6$-alkoxy; or
(b) —(CH$_2$)$_n$—V, wherein n is as defined above and V is H, OH, OR⁴, NHR⁴, NR$_2$⁴, NHCOR⁴, NHSO$_2$R⁴, CONHR⁴, CONR$_2$⁴, COOH, COOR⁴, SO$_2$R⁴, SOR⁴, SONHR⁴, SONR$_2$⁴, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, SR⁴, trihalo-$C_1$–$C_6$-alkyl, $C_1$–$C_6$-alkyl and $C_1$–$C_6$-alkoxy; or
(c) phenyl fused to a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, SR⁴, trihalo-$C_1$–$C_6$-alkyl, $C_1$–$C_6$-alkyl and $C_1$–$C_6$-alkoxy; and R⁴ is $C_1$–$C_6$-alkyl;

and optical and geometrical isomers, and pharmaceutically acceptable salts thereof.

3. A compound according to claim 1 having the formula (Ia)

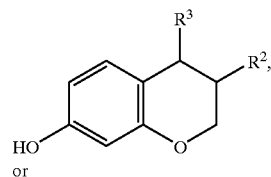

or (Ib)

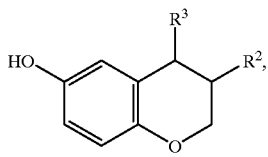

wherein R¹, R² and R³ are as defined above.

4. A compound according to claim 1 in which R² is phenyl optionally substituted with 1 to 5 substituents independently selected from the group consisting of OH, halogen, nitro, cyano, SH, SR⁴, trihalo-$C_1$–$C_6$-alkyl, $C_1$–$C_6$-alkyl and $C_1$–$C_6$-alkoxy.

5. A compound according to claim 1 in which R² is phenyl optionally substituted with 1 to 3 substituents independently selected from the group consisting of OH, halogen, nitro, cyano, SH, SR⁴, trihalo-$C_1$–$C_6$-alkyl, $C_1$–$C_6$-alkyl and $C_1$–$C_6$-alkoxy.

6. A compound according to claim 1 in which R³ is phenyl substituted with —X—(CH$_2$)$_n$—Y, wherein:
X is a valency bond, O or S,
n is an integer in the range of 1 to 12,
Y is H, OH, OR⁴, NHCOR⁴, NHSO$_2$R⁴, CONHR⁴, CONR$_2$⁴, COOH, COOR⁴, SO$_2$R⁴, SOR⁴, SONHR⁴, SONR$_2$⁴, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, SR⁴, trihalo-$C_1$–$C_6$-alkyl, $C_1$–$C_6$-alkyl and $C_1$–$C_6$-alkoxy.

7. A compound according to claim 1 wherein R³ is —(CH$_2$)$_n$—V, wherein n is as defined above and V is H, OH, OR⁴, NHR⁴, NR$_2$⁴, NHCOR⁴, NHSO$_2$R⁴, CONHR⁴, CONR$_2$⁴, COOH, COOR⁴, SO$_2$R⁴, SOR⁴, SONHR⁴, SONR$_2$⁴, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, SR⁴, trihalo-$C_1$–$C_6$-alkyl, $C_1$–$C_6$-alkyl and $C_1$–$C_6$-alkoxy.

8. A compound according to claim 1 wherein R³ is phenyl fused to a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, SR⁴, trihalo-$C_1$–$C_6$-alkyl, $C_1$–$C_6$-alkyl and $C_1$–$C_6$-alkoxy.

9. A compound according to claim 1 having the formula

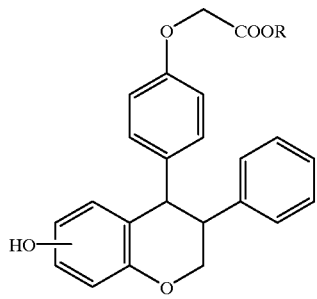

wherein R is H or $C_1$–$C_6$ alkyl.

10. A compound according to claim 1 having the formula

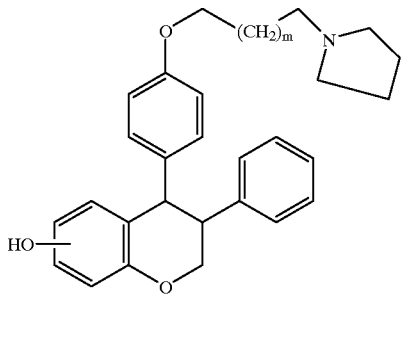

wherein m is an integer from 0 to 10.

11. A compounds according to claim 1 having the formula

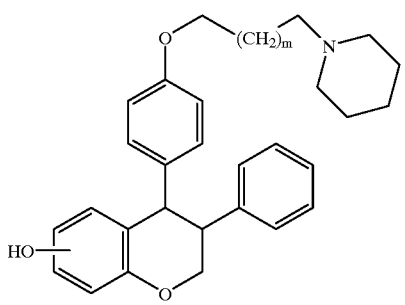

wherein m is as defined above.

12. A compound according to claim 1 having the formula

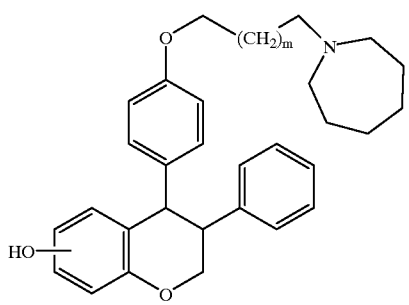

wherein m is as defined above.

13. A compound according to claim 1 having the formula

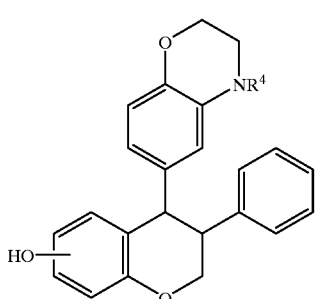

wherein $R^4$ is as defined above.

14. A compound according to claim 1 having the formula

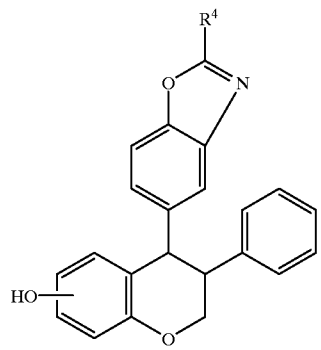

wherein $R^4$ is as defined above.

15. A compound according to claim 1 having the formula

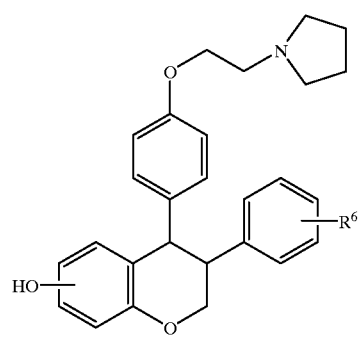

wherein $R^6$ represents one or more of the following substituents: methoxy, hydroxy, trifluormethyl, fluoro and chloro.

16. A compound according to claim 1 selected from the following:
(−)-cis-4-(4-(Carboxymethoxy)phenyl)-7-hydroxy-3-phenylchromane,
(−)-cis-7-Hydroxy-4-(4-methoxycarbonylmethoxy)phenyl)-3-phenylchromane,
(−)-cis-4-(4-(Ethoxycarbonylmethoxy)phenyl)-7-hydroxy-3-phenylchromane,
(−)-cis-4-(4-(Benzyloxycarbonylmethoxy)phenyl)-7-hydroxy-3-phenylchromane,
(−)-cis-7-Hydroxy-3-phenyl-4-(4-(2-pyrrolidinoethoxy)phenyl)chromane,
(−)-cis-7-Hydroxy-3-phenyl-4-(4-(3-pyrrolidinopropoxy)phenyl)chromane,
(−)-cis-7-Hydroxy-3-phenyl-4-(4-(4-pyrrolidinobutoxy)phenyl)chromane,
(−)-cis-7-Hydroxy-3-phenyl-4-(4-(5-pyrrolidinopentoxy)phenyl)chromane,
(−)-cis-7-Hydroxy-3-phenyl-4-(4-(6-pyrrolidinohexyloxy)phenyl)chromane,
(−)-cis-7-Hydroxy-3-phenyl-4-(4-(7-pyrrolidinoheptyloxy)phenyl)chromane,
(−)-cis-7-Hydroxy-3-phenyl-4-(4-(8-pyrrolidinooctyloxy)phenyl)chromane,
(−)-cis-7-Hydroxy-3-phenyl-4-(4-(9-pyrrolidinononyloxy)phenyl)chromane,
(−)-cis-7-Hydroxy-3-phenyl-4-(4-(10-pyrrolidinodecyloxy)phenyl)chromane,
(−)-cis-7-Hydroxy-3-phenyl-4-(4-(11-pyrrolidinoundecyloxy)phenyl)chromane,
(−)-cis-7-Hydroxy-3-phenyl-4-(4-(12-pyrrolidinododecyloxy)phenyl)chromane, (−)-cis-7-Hydroxy-3-phenyl-4-(4-(2-piperidinoethoxy) phenyl)chromane,
(−)-cis-7-Hydroxy-3-phenyl-4-(4-(3-piperidinopropoxy) phenyl)chromane,
(−)-cis-7-Hydroxy-3-phenyl-4-(4-(4-piperidinobutoxy) phenyl)chromane,
(−)-cis-7-Hydroxy-4-(4-(2-perhydroazepinoethoxy) phenyl)-3-phenylchromane,
(−)-cis-7-Hydroxy-4-(4-(3-perhydroazepinopropoxy) phenyl)-3-phenylchromane,
(−)-cis-7-Hydroxy-4-(4-(4-perhydroazepinobutoxy) phenyl)-3-phenylchromane,
(−)-cis-4-(2,3-Dihydro-1,4-benzoxazin-6-yl)-7-hydroxy-3-phenylchromane,
(−)-cis-7-Hydroxy-4-(4-methyl-2,3-dihydro-1,4-benzoxazin-6-yl)-3-phenylchromane,
(−)-cis-4-(4-Ethyl-2,3-dihydro-1,4-benzoxazin-6-yl)-7-hydroxy-3-phenylchromane,
(−)-cis-7-Hydroxy-3-(4-hydroxyphenyl)-4-(4-(2-pyrrolidinoethoxy)phenyl)chromane,
(−)-cis-7-Hydroxy-3-(4-trifluoromethylphenyl)-4-(4-(2-pyrrolidinoethoxy)phenyl)chromane,
(−)-cis-7-Hydroxy-3-(4-fluorophenyl)-4-(4-(2-pyrrolidinoethoxy)phenyl)chromane,
(−)-cis-3-(4-Chlorophenyl)-7-hydroxy-4-(4-(2-pyrrolidinoethoxy)phenyl)chromane,
(−)-cis-3-(3,4-Dimethoxyphenyl)-7-hydroxy-4-(4-(2-pyrrolidinoethoxy)phenyl)chromane,
(−)-cis-7-Hydroxy-3-(pentafluorophenyl)-4-(4-(2-pyrrolidinoethoxy)phenyl)chromane,
(−)-cis-4-(4-(Carboxymethoxy)phenyl)-6-hydroxy-3-phenylchromane,
(−)-cis-6-Hydroxy-4-(4-(methoxycarbonylmethoxy)phenyl)-3-phenylchromane,
(−)-cis-4-(4-(Ethoxycarbonylmethoxy)phenyl)-6-hydroxy-3-phenylchromane,
(−)-cis-4-(4-(Benzyloxycarbonylmethoxy)phenyl)-6-hydroxy-3-phenylchromane,
(−)-cis-6-Hydroxy-3-phenyl-4-(4-(2-pyrrolidinoethoxy) phenyl)chromane,
(−)-cis-6-Hydroxy-3-phenyl-4-(4-(3-pyrrolidinopropoxy) phenyl)chromane,
(−)-cis-6-Hydroxy-3-phenyl-4-(4-(4-pyrrolidinobutoxy) phenyl)chromane,
(−)-cis-6-Hydroxy-3-phenyl-4-(4-(5-pyrrolidinopentoxy) phenyl)chromane,
(−)-cis-6-Hydroxy-3-phenyl-4-(4-(6-pyrrolidinohexyloxy) phenyl)chromane,
(−)-cis-6-Hydroxy-3-phenyl-4-(4-(7-pyrrolidinoheptyloxy) phenyl)chromane,
(−)-cis-6-Hydroxy-3-phenyl-4-(4-(8-pyrrolidinooctyloxy) phenyl)chromane,
(−)-cis-6-Hydroxy-3-phenyl-4-(4-(9-pyrrolidinononyloxy) phenyl)chromane,
(−)-cis-6-Hydroxy-3-phenyl-4-(4-(10-pyrrolidinodecyloxy) phenyl)chromane,
(−)-cis-6-Hydroxy-3-phenyl-4-(4-(11-pyrrolidinoundecyloxy)phenyl)chromane,
(−)-cis-6-Hydroxy-3-phenyl-4-(4-(12-pyrrolidinododecyloxy)phenyl)chromane,
(−)-cis-6-Hydroxy-3-phenyl-4-(4-(2-piperidinoethoxy) phenyl)chromane,
(−)-cis-6-Hydroxy-3-phenyl-4-(4-(3-piperidinopropoxy) phenyl)chromane,
(−)-cis-6-Hydroxy-3-phenyl-4-(4-(4-piperidinobutoxy) phenyl)chromane,
(−)-cis-6-Hydroxy-4-(4-(2-perhydroazepinoethoxy) phenyl)-3-phenylchromane,
(−)-cis-6-Hydroxy-4-(4-(3-perhydroazepinopropoxy) phenyl)-3-phenylchromane,
(−)-cis-6-Hydroxy-4-(4-(4-perhydroazepinobutoxy) phenyl)-3-phenylchromane,
(−)-cis-4-(2,3-Dihydro-1,4-benzoxazin-6-yl)-6-hydroxy-3-phenylchromane,
(−)-cis-6-Hydroxy-4-(4-methyl-2,3-dihydro-1,4-benzoxazin-6-yl)-3-phenylchromane,
(−)-cis-4-(4-Ethyl-2,3-dihydro-1,4-benzoxazin-6-yl)-6-hydroxy-3-phenylchromane,
(−)-cis-6-Hydroxy-3-(4-hydroxyphenyl)-4-(4-(2-pyrrolidinoethoxy)phenyl)chromane,
(−)-cis-6-Hydroxy-3-(4-trifluoromethylphenyl)-4-(4-(2-pyrrolidinoethoxy)phenyl)chromane,
(−)-cis-6-Hydroxy-3-(4-fluorophenyl)-4-(4-(2-pyrrolidinoethoxy)phenyl)chromane,
(−)-cis-3-(4-Chlorophenyl)-6-hydroxy-4-(4-(2-pyrrolidinoethoxy)phenyl)chromane,
(−)-cis-3-(3,4-Dimethoxyphenyl)-6-hydroxy-4-(4-(2-pyrrolidinoethoxy)phenyl)chromane,
(−)-cis-6-Hydroxy-3-(pentafluorophenyl)-4-(4-(2-pyrrolidinoethoxy)phenyl)chromane,
(+)-cis-4-(4-(Carboxymethoxy)phenyl)-7-hydroxy-3-phenylchromane,
(+)-cis-7-Hydroxy-4-(4-(methoxycarbonylmethoxy) phenyl)-3-phenylchromane,
(+)-cis-4-(4-(Ethoxycarbonylmethoxy)phenyl)-7-hydroxy-3-phenylchromane,
(+)-cis-4-(4-(Benzyloxycarbonylmethoxy)phenyl)-7-hydroxy-3-phenylchromane,
(+)-cis-7-Hydroxy-3-phenyl-4-(4-(2-pyrrolidinoethoxy) phenyl)chromane,
(+)-cis-7-Hydroxy-3-phenyl-4-(4-(3-pyrrolidinopropoxy) phenyl)chromane,
(+)-cis-7-Hydroxy-3-phenyl-4-(4-(4-pyrrolidinobutoxy) phenyl)chromane,
(+)-cis-7-Hydroxy-3-phenyl-4-(4-(5-pyrrolidinopentoxy) phenyl)chromane,
(+)-cis-7-Hydroxy-3-phenyl-4-(4-(6-pyrrolidinohexyloxy) phenyl)chromane,
(+)-cis-7-Hydroxy-3-phenyl-4-(4-(7-pyrrolidinoheptyloxy) phenyl)chromane,
(+)-cis-7-Hydroxy-3-phenyl-4-(4-(8-pyrrolidinooctyloxy) phenyl)chromane,
(+)-cis-7-Hydroxy-3-phenyl-4-(4-(9-pyrrolidinononyloxy) phenyl)chromane,
(+)-cis-7-Hydroxy-3-phenyl-4-(4-(10-pyrrolidinodecyloxy) phenyl)chromane,
(+)-cis-7-Hydroxy-3-phenyl-4-(4-(11-pyrrolidinoundecyloxy)phenyl)chromane,
(+)-cis-7-Hydroxy-3-phenyl-4-(4-(12-pyrrolidinododecyloxy)phenyl)chromane,
(+)-cis-7-Hydroxy-3-phenyl-4-(4-(2-piperidinoethoxy) phenyl)chromane,
(+)-cis-7-Hydroxy-3-phenyl-4-(4-(3-piperidinopropoxy) phenyl)chromane,
(+)-cis-7-Hydroxy-3-phenyl-4-(4-(4-piperidinobutoxy) phenyl)chromane,
(+)-cis-7-Hydroxy-4-(4-(2-perhydroazepinoethoxy) phenyl)-3-phenylchromane,
(+)-cis-7-Hydroxy-4-(4-(3-perhydroazepinopropoxy) phenyl)-3-phenylchromane,
(+)-cis-7-Hydroxy-4-(4-(4-perhydroazepinobutoxy) phenyl)-3-phenylchromane,
(+)-cis-4-(2,3-Dihydro-1,4-benzoxazin-6-yl)-7-hydroxy-3-phenylchromane,
(+)-cis-7-Hydroxy-4-(4-methyl-2,3-dihydro-1,4-benzoxazin-6-yl)-3-phenylchromane, (+)-cis-4-(4-Ethyl-2,3-dihydro-1,4-benzoxazin-6-yl)-7-hydroxy-3-phenylchromane,
(+)-cis-7-Hydroxy-3-(4-hydroxyphenyl)-4-(4-(2-pyrrolidinoethoxy)phenyl)chromane,
(+)-cis-7-Hydroxy-3-(4-trifluoromethylphenyl)-4-(4-(2-pyrrolidinoethoxy)phenyl)chromane,
(+)-cis-7-Hydroxy-3-(4-fluorophenyl)-4-(4-(2-pyrrolidinoethoxy)phenyl)chromane,
(+)-cis-3-(4-Chlorophenyl)-7-hydroxy-4-(4-(2-pyrrolidinoethoxy)phenyl)chromane,
(+)-cis-3-(3,4-Dimethoxyphenyl)-7-hydroxy-4-(4-(2-pyrrolidinoethoxy)phenyl)chromane,
(+)-cis-7-Hydroxy-3-(pentafluorophenyl)-4-(4-(2-pyrrolidinoethoxy)phenyl)chromane,
(+)-cis-4-(4-(Carboxymethoxy)phenyl)-6-hydroxy-3-phenylchromane,
(+)-cis-6-Hydroxy-4-(4-(methoxycarbonylmethoxy)phenyl)-3-phenylchromane,
(+)-cis-4-(4-(Ethoxycarbonylmethoxy)phenyl)-6-hydroxy-3-phenylchromane,
(+)-cis-4-(4-(Benzyloxycarbonylmethoxy)phenyl)-6-hydroxy-3-phenylchromane,
(+)-cis-6-Hydroxy-3-phenyl-4-(4-(2-pyrrolidinoethoxy)phenyl)chromane,
(+)-cis-6-Hydroxy-3-phenyl-4-(4-(3-pyrrolidinopropoxy)phenyl)chromane,
(+)-cis-6-Hydroxy-3-phenyl-4-(4-(4-pyrrolidinobutoxy)phenyl)chromane,
(+)-cis-6-Hydroxy-3-phenyl-4-(4-(5-pyrrolidinopentoxy)phenyl)chromane,
(+)-cis-6-Hydroxy-3-phenyl-4-(4-(6-pyrrolidinohexyloxy)phenyl)chromane,
(+)-cis-6-Hydroxy-3-phenyl-4-(4-(7-pyrrolidinoheptyloxy)phenyl)chromane,
(+)-cis-6-Hydroxy-3-phenyl-4-(4-(8-pyrrolidinooctyloxy)phenyl)chromane,
(+)-cis-6-Hydroxy-3-phenyl-4-(4-(9-pyrrolidinononyloxy)phenyl)chromane,
(+)-cis-6-Hydroxy-3-phenyl-4-(4-(10-pyrrolidinodecyloxy)phenyl)chromane,
(+)-cis-6-Hydroxy-3-phenyl-4-(4-(11-pyrrolidinoundecyloxy)phenyl)chromane,
(+)-cis-6-Hydroxy-3-phenyl-4-(4-(12-pyrrolidinododecyloxy)phenyl)chromane,
(+)-cis-6-Hydroxy-3-phenyl-4-(4-(2-piperidinoethoxy)phenyl)chromane,
(+)-cis-6-Hydroxy-3-phenyl-4-(4-(3-piperidinopropoxy)phenyl)chromane,
(+)-cis-6-Hydroxy-3-phenyl-4-(4-(4-piperidiobutoxy)phenyl)chromane,
(+)-cis-6-Hydroxy-4-(4-(2-perhydroazepinoethoxy)phenyl)-3-phenylchromane,
(+)-cis-6-Hydroxy-4-(4-(3-perhydroazepinopropoxy)phenyl)-3-phenylchromane,
(+)-cis-6-Hydroxy-4-(4-(4-perhydroazepinabutoxy)phenyl)-3-phenylchromane,
(+)-cis-4-(2,3-Dihydro-1,4-benzoxazin-6-yl)-6-hydroxy-3-phenylchromane,
(+)-cis-6-Hydroxy-4-(4-methyl-2,3-dihydro-1,4-benzoxazin-6-yl)-3-phenylchromane,
(+)-cis-4-(4-Ethyl-2,3-dihydro-1,4-benzoxazin-6-yl)-6-hydroxy-3-phenylchromane,
(+)-cis-6(Hydroxy-23-(4hydroxyheyl 4-(2-pyrrolidinoethoxyphenyl)chromane,
(+)-cis-6-Hydroxy-3-(4-triluromethylphenyl)-4-(4-(2-pyrrolidinoethoxy)phenyl)chromane,
(+)-cis-6-Hydroxy-3-(4-fluoroyphenyl)-4-(4-(2-pyrrolidinoethoxy)phenyl)chromane,
(+)-cis-3-(4-Chlorophenyl)-6-hydyroxy-4-(4-(2-pyrrolidinnethoxy)phenyl)chromane,
(+)-cis-3-(3,4-Dimethoxyphenyl)-6-hydroxy-4-(4-(2-pyrrolidinoethoxy)phenyl)chromane,
(+)-cis-6-Hydroxy-3-(pentafluorophenyl)-4-(4-(2-pyrrolidinoethoxy)phenyl)chromane,
(+)-cis-7-Hydroxy-3-phenyl-4-{4-{2-(pyrrolidin-1-yl)ethoxy}phenyl}chromane,
(−)-cis-7-Hydroxy-3-phenyl-4-{4-[2-(pyrrolidin-1-yl)ethoxy]phenyl}chromane,
(+)-cis-7-Hydroxy-4(4-(2-pyrrolidinoethoxy)phenyl)-3-(4-(trifluoromethyl)phenyl)-chromane
(+)-cis-7-Hydroxy-3-(4-methylphenyl)-4-(4-(2-pyrrolidinoethoxy)phenyl)chromane,
(+)-cis-7-Hydroxy-3-(3-hydroxyphenyl)-4-(4-(2pyrrolidinoethy)phenyl)chromane,
(−)-cis-7-Hydroxy-4-(4-(2-pyrrolidinoethoxy)phenyl)-3-(4-(trifluoromethyl)phenyl)-chromane,
(−)-cis-7-Hydroxy-3-(4-methylphenyl)-4-(4-(2-pyrrolidinoethoxy)phenyl)chromane, and
(−)-cis-7-Hydroxy-3-(3-hydroxyphenyl)-4-(4-(2-pyrrolidinoethoxy)phenyl)chromnane,
or any mixture thereof.

17. A compound according to claim 1 selected from the following:
(±)-cis-7-Hydroxy-3-phenyl-4-{4-{2-(pyrrolidin-1-yl)ethoxy}phenyl}chromane,
(±)-cis-7-Hydroxy-3-(4-fluorophenyl)-4-(4-(2-pyrrolidinoethoxy)phenyl)chromane,
(±)-cis-7-Hydroxy-3-(4-fluorophenyl)-4-(4-(2-piperidinoethoxy)phenyl)-chromane,
(±)-cis-7-Hydroxy-3-(4-fluorophenyl)-4-(4-(3-piperidinopropoxy)phenyl)chromane,
(±)-cis-7-Hydroxy-3-phenyl-4-(4-(2-piperidinoethoxy)phenyl)chromane,
(±)-cis-7-Hydroxy-3-phenyl-4-(4-(2-piperidinoethoxy)phenyl)chromane,
(±)-cis-7-Hydroxy-3-(4-hydroxyphenyi)-4-(4-(2-pyrrolidinoethoxy)phenyl)chromane,
(±)-cis-7-Hydroxy-3-(4-phenyl-phenyl)-4-(4-(2-pyrrolidinoethoxy)phenyl)chromane,
(±)-cis-7-Hydroxy-3-(4-methylphenyl)-4-(4-(2-pyrrolidinoethoxy)phenyl)chromane,
(±)-cis-7-Hydroxy-3-(4-methylphenyl)-4-(4-(2-piperidinoethoxy)phenyl)chromane,
(±)-cis-7-Hydroxy-4-(4-(2-piperidinoethoxy)phenyl)-3-(4-(trifluoromethyl)phenyl)-chromane,
(±)-cis-7-Hydroxy-4-(4-(2-pyrrolidinoethoxy)phenyl)-3-(4-(trifluoromethyl)phenyl)-chromane,
(±)-cis-7-Hydroxy-3-(3-methylphenyl)-4-(4-(2-pyrrolidinoethoxy)phenyl)chromane,
(±)-cis-3-(3-Fluorophenyl)-7-hydroxy-4-(4-(2-pyrrolidinoethoxy)phenyl)chromane,
(±)-cis-7-Hydroxy-3-(3-hydroxyphenyl)-4-(4-(2-pyrrolidinoethoxy)phenyl)chromane,
(±)-cis-7-Hydroxy-3-(3-hydroxyphenyl)-4-(4-(2-piperidinoethoxy)phenyl)chromane,
(±)-cis-7-Hydroxy-3-(3-hydroxyphenyl)-4-(4-(3-piperidinopropoxy)phenyl)chromane,
(±)-cis-7-Hydroxy-4-(4-(2-pyrrolidinoethoxy)phenyl)-3-(3-(trifluoromethyl)phenyl)-chromane,
(±)-cis-7-Hydroxy-4-(4-(2-piperidinoethoxy)phenyl)-3-(3-(trifluoromethyl)phenyl)-chromane,
(±)-cis-3-(2-Fluorophenyl)-7-hydroxy-4-(4-(2-pyrrolidinoethoxy)phenyl)chromane,
(±)-cis-7-Hydroxy-3-(2,3,4,5,6-pentafluorophenyl)-4-(4-(2-pyrrolidinoethoxy)phenyl)-chromane,
(±)-cis-7-Hydroxy-3-(2,3,4,5,6-pentafluorophenyl)-4-(4-(2-piperidinoethoxy)phenyl)-chromane, (±)-cis-6-Hydroxy-3-phenyl-4-(4-(2-pyrrolidinoethoxy) phenyl)-chromane, (±)-cis-6-Hydroxy-3-(3-hydroxyphenyl)-4-(4-(2-pyrrolidinoethoxy)phenyl)chromane, (±)-cis-4-(4-Hexylphenyl)-7-hydroxy-3-phenylchromane, (+,−) cis[4-(7-Hydroxy-3-phenyl-chroman-4-yl)-phenoxy]-acetic acid, (+,−) cis 4-[4-(7-Hydroxy-3-phenyl-chroman-4-yl)-phenoxy]-butyric acid, (+,−) cis 7-hydroxy-4-[4-(6-morpholinohexyloxy)-phenyl]-3-phenyl-chroman, (+,−) cis 7-Hydroxy 4-[4-(morpholinoethyloxy)-phenyl]-3-phenyl-chroman, (+,−) cis 7-Hydroxy 4-[4-(N-methylpiperazinoethyloxy)-phenyl]-3-phenyl-chroman, (+,−) cis 7-Hydroxy 4-[4-(morpholinobutyloxy)-phenyl]-3-phenyl-chroman, (+,−) cis 7-Hydroxy-4[4-(morpholinodecyloxy)-phenyl]-3-phenylchroman, and (+,−) cis 7-Hydroxy 4-[4-(morpholinobutyloxy)-phenyl]-3-phenyl-chroman.

18. A pharmaceutical composition comprising an effective amount of a compound according to claims 1 to 17 or a pharmaceutical acceptable salt thereof and a pharmaceutical carrier or diluent.

19. A pharmaceutical composition according to claim 18 in the form of an oral dosage unit or parenteral dosage unit.

20. A method for treating estrogen-dependent cancers, senile dementia-Alzheimer's type and prostatic carcinoma comprising administering to a mammal in need thereof an effective amount of a compound of claim 1.

21. A method of contraception comprising administering to a male or female mammal an effective amount of a compound according to claim 1.

22. A method for treating estrogen related diseases or syndromes caused by an estrogen-deficient state in a mammal, comprising administering to a subject in need thereof an effective amount of a compound according to claim 1.

23. A method for treating bone loss, osteoporosis, cardiovascular diseases, cognitive disorders, menopausal symptoms, incontinence, obesity, dysmenorrhea, dysfunctional uterine bleeding, acne, hirsutism, post-partum lactation, threatened or habitual abortion, for regulating glucose metabolism, and for aiding ovarian development, said method comprising administering to a mammal in need thereof an effective amount of a compound of claim 1.

24. The method according to claim 23, wherein the menopausal symptoms are flushing, urogenital atrophy, depression, mania, or schizophrenia.

25. A method for preventing estrogen related diseases or syndromes caused by an estrogen-deficient state in a mammal, comprising administering to a subject in need thereof an effective amount of a compound according to claim 1.

26. A method for preventing bone loss, osteoporosis, cardiovascular diseases, cognitive disorders, menopausal symptoms, incontinence, obesity, dysmenorrhea, dysfunctional uterine bleeding, acne, hirsutism, post-partum lactation, threatened or habitual abortion, for regulating glucose metabolism, and for aiding ovarian development, said method comprising administering to a mammal in need thereof an effective amount of a compound of claim 1.

27. The method according to claim 25, wherein the menopausal symptoms are flushing, urogenital atrophy, depression, mania, or schizophrenia.

* * * * *